United States Patent
Van Wyk

(10) Patent No.: US 11,957,370 B2
(45) Date of Patent: *Apr. 16, 2024

(54) SIMPLIFIED VASECTOMY METHODS

(71) Applicant: Signati Medical Inc., Providence, RI (US)

(72) Inventor: Robert A. Van Wyk, St. Pete Beach, FL (US)

(73) Assignee: Signati Medical Inc., Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/503,857

(22) Filed: Nov. 7, 2023

(65) Prior Publication Data

US 2024/0065714 A1  Feb. 29, 2024

Related U.S. Application Data

(63) Continuation of application No. 18/341,375, filed on Jun. 26, 2023, now Pat. No. 11,844,540, which is a continuation of application No. 17/709,675, filed on Mar. 31, 2022, now Pat. No. 11,723,680, which is a continuation-in-part of application No. 16/700,393, filed on Dec. 2, 2019, now Pat. No. 11,291,581, and a continuation-in-part of application No. 17/338,115,
(Continued)

(51) Int. Cl.
*A61B 17/28* (2006.01)
*A61F 6/20* (2006.01)

(52) U.S. Cl.
CPC ............ *A61B 17/282* (2013.01); *A61F 6/20* (2013.01); *A61B 2017/2808* (2013.01)

(58) Field of Classification Search
CPC .. A61F 6/20; A61F 6/202; A61F 6/204; A61F 6/206; A61F 6/208; A61B 17/282; A61B 17/30; A61B 17/2812; A61B 2017/2808; A61B 2017/00349; A61B 2017/2837; A61B 2017/305; A61B 18/1442; A61B 2018/00547; A61B 2018/126
See application file for complete search history.

(56) References Cited

U.S. PATENT DOCUMENTS 3,762,417 A  10/1973  Textor
4,803,983 A   2/1989  Siegel
(Continued)

*Primary Examiner* — Ronald Hupczey, Jr.
(74) *Attorney, Agent, or Firm* — Smith Patent, LLC; Chalin A. Smith

(57) ABSTRACT

Conventional vasectomy techniques suffer from a number of disadvantages and potential complications, including, for example, a substantial risk for the development of hematomas, swelling, and post-surgical pain, a potential for spontaneous regeneration and undesired resumption of fertility, a need for a highly skilled surgical professional, as well as a long recovery period, accompanied by severe limitations on post-surgical activity. The present invention overcomes the disadvantages and deficiencies of the prior art by providing vasectomy instruments, kits, and methods that allow for a rapid, reliable, less invasive male sterilization procedure that may be readily, reliably and successfully performed by minimally skilled personnel around the world in a variety of medical settings.

9 Claims, 72 Drawing Sheets

Related U.S. Application Data filed on Jun. 3, 2021, now Pat. No. 11,291,493, which is a continuation-in-part of application No. 17/150,313, filed on Jan. 15, 2021, now abandoned, which is a continuation-in-part of application No. 16/700,393, filed on Dec. 2, 2019, now Pat. No. 11,291,581.

(60) Provisional application No. 62/917,325, filed on Dec. 3, 2018, provisional application No. 62/995,188, filed on Jan. 16, 2020.

(56) References Cited

U.S. PATENT DOCUMENTS

| | | | |
|---|---|---|---|
| 4,920,982 | A | 5/1990 | Goldstein |
| 5,026,379 | A | 6/1991 | Yoon |
| 5,203,785 | A | 4/1993 | Slater |
| 5,445,638 | A | 8/1995 | Rydell et al. |
| 5,667,518 | A | 9/1997 | Pannell |
| 5,702,390 | A | 12/1997 | Austin et al. |
| 5,797,958 | A | 8/1998 | Yoon |
| 5,827,279 | A | 10/1998 | Hughett et al. |
| 5,865,835 | A | 2/1999 | Lolagne |
| 5,891,141 | A | 4/1999 | Rydell |
| 5,972,002 | A | 10/1999 | Bark |
| 6,610,060 | B2 | 8/2003 | Mulier et al. |
| 6,843,789 | B2 | 1/2005 | Goble |
| 8,220,464 | B2 | 7/2012 | Pannell et al. |
| 8,561,615 | B2 | 10/2013 | Pannell et al. |
| D886,297 | S | 6/2020 | Van Wyk |
| D903,867 | S | 12/2020 | Van Wyk |
| 11,291,493 | B2 * | 4/2022 | Van Wyk ............ A61B 17/2812 |
| 11,291,581 | B2 | 4/2022 | Van Wyk |
| 11,844,540 | B2 * | 12/2023 | Van Wyk ............. A61B 17/282 |
| 2001/0031961 | A1 | 10/2001 | Hooven et al. |
| 2002/0107517 | A1 | 8/2002 | Witt et al. |
| 2003/0069571 | A1 | 4/2003 | Treat et al. |
| 2003/0078577 | A1 | 4/2003 | Truckai et al. |
| 2004/0158286 | A1 | 8/2004 | Roux et al. |
| 2004/0249368 | A1 | 12/2004 | Hooven |
| 2005/0033353 | A1 | 2/2005 | Jones |
| 2005/0101952 | A1 | 5/2005 | Lands et al. |
| 2006/0069388 | A1 | 3/2006 | Truckai et al. |
| 2008/0077156 | A1 | 3/2008 | Emstad |
| 2008/0105265 | A1 * | 5/2008 | Pannell ................ A61B 17/122 606/45 |
| 2010/0145381 | A1 | 6/2010 | Moon |
| 2010/0288285 | A1 | 11/2010 | Marmar |
| 2020/0170831 | A1 | 1/2020 | Van Wyk |

* cited by examiner

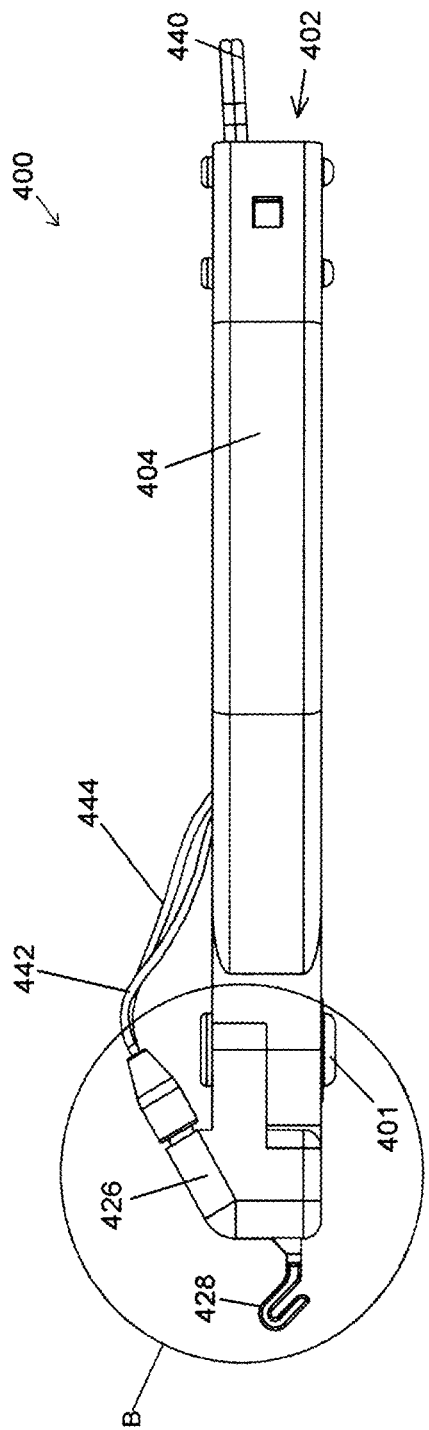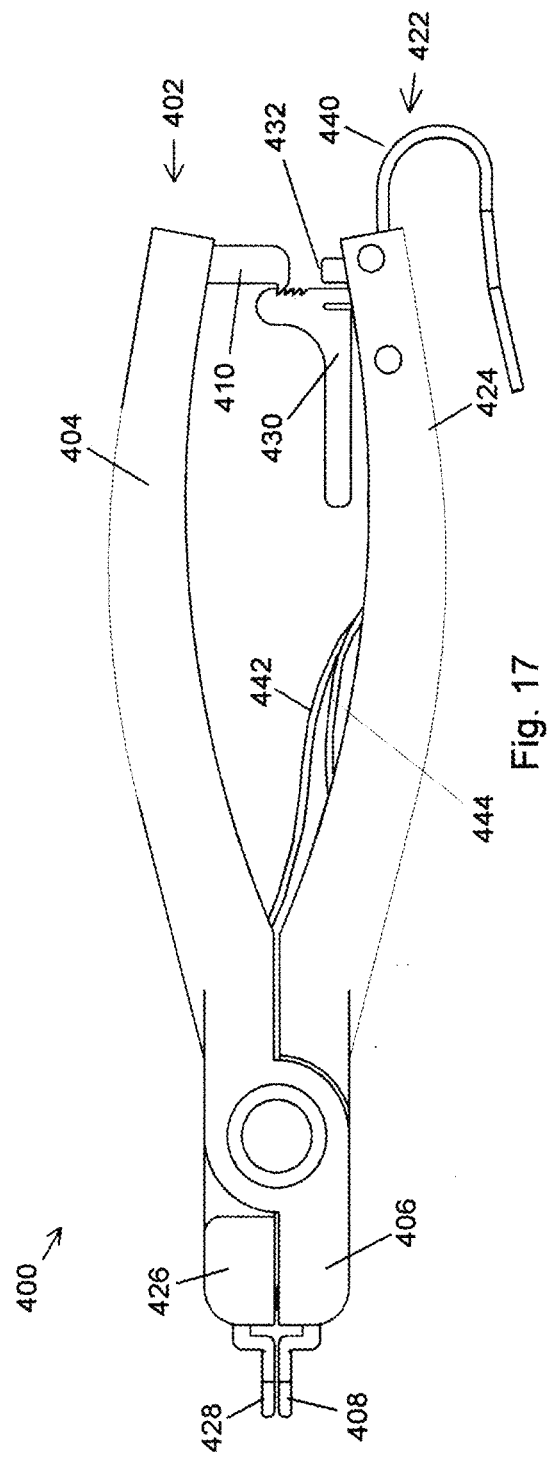
Fig. 16
Fig. 17

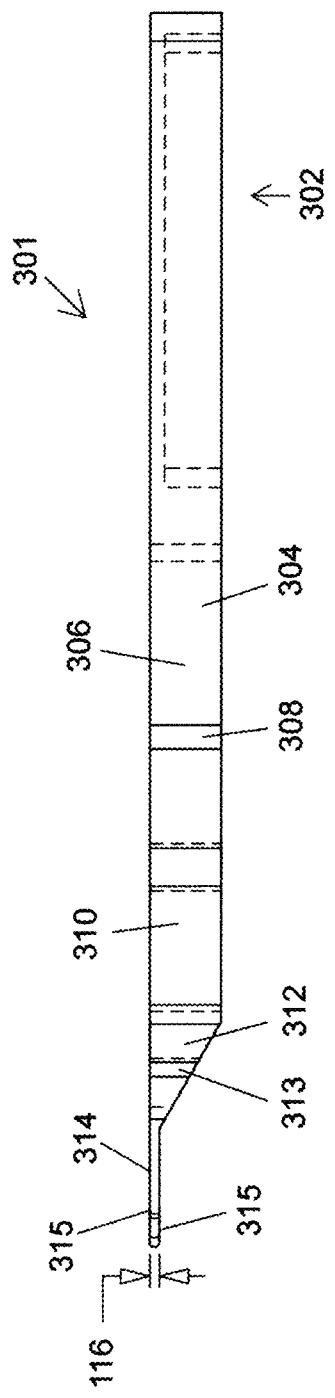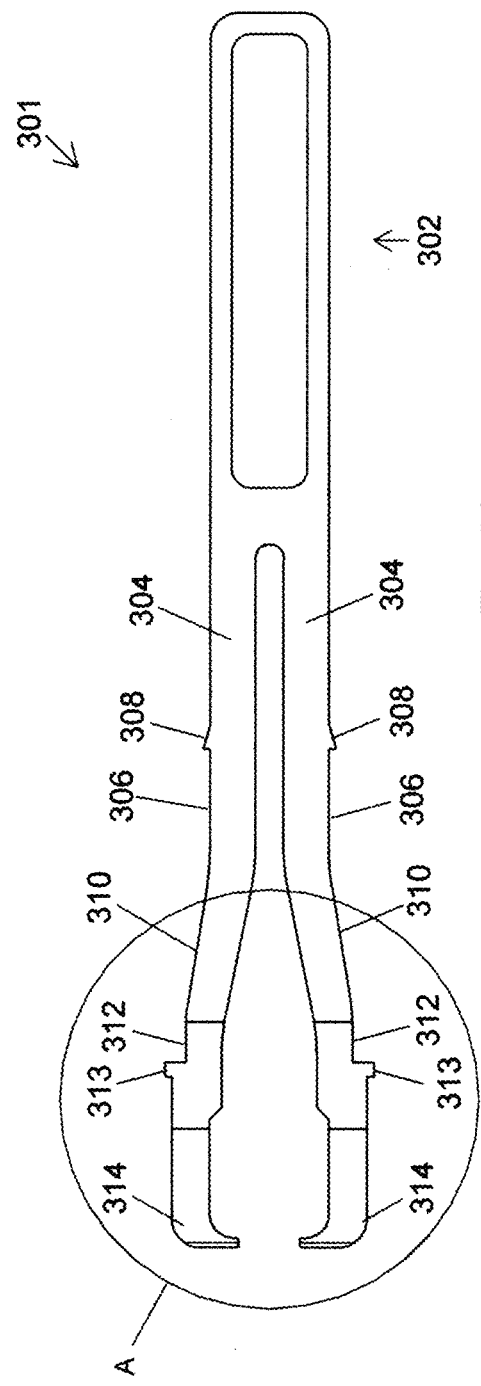

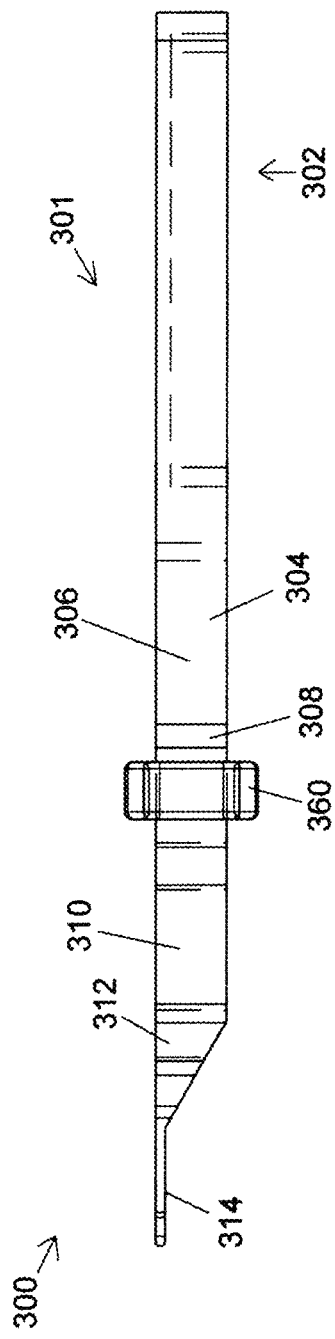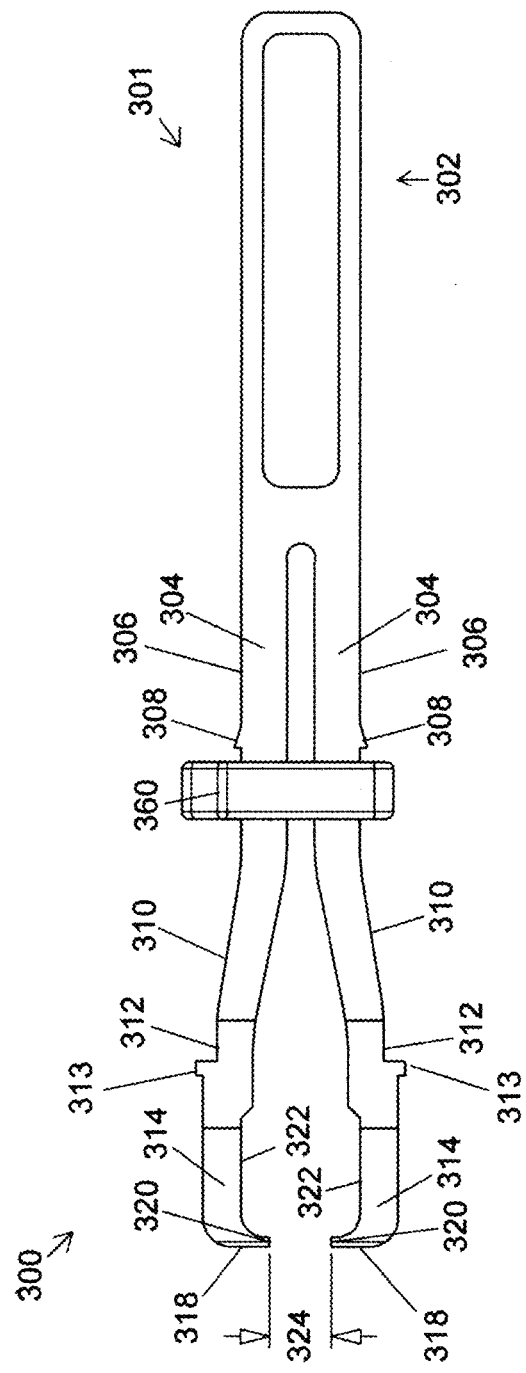
Fig. 65
Fig. 66

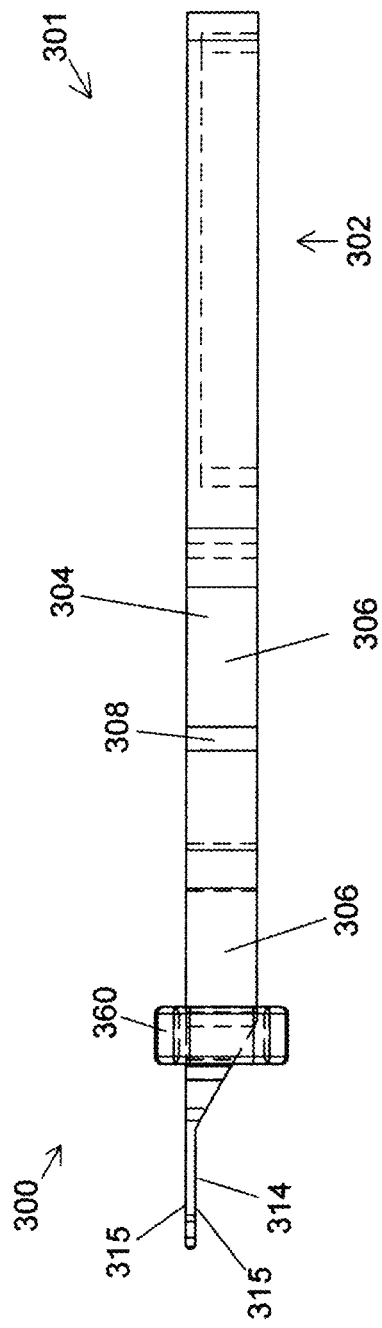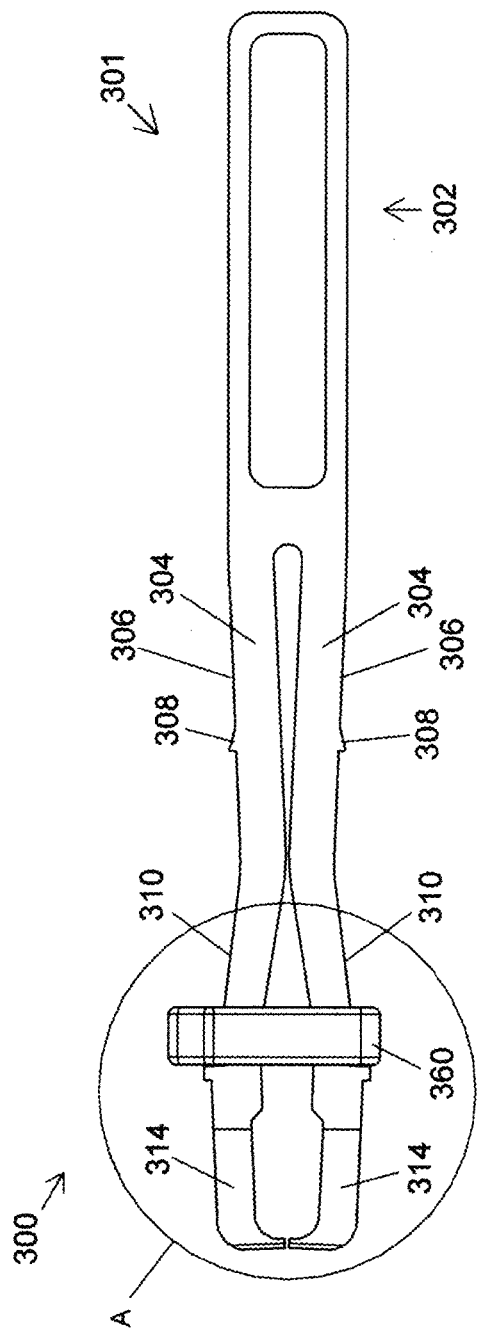
Fig. 68
Fig. 69

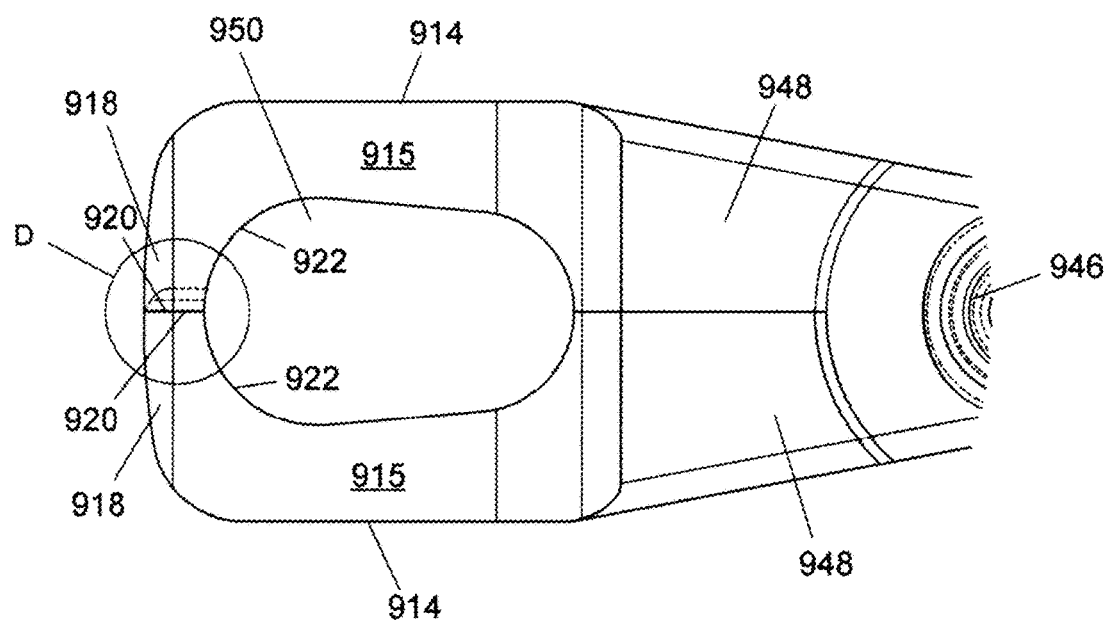
Fig. 102
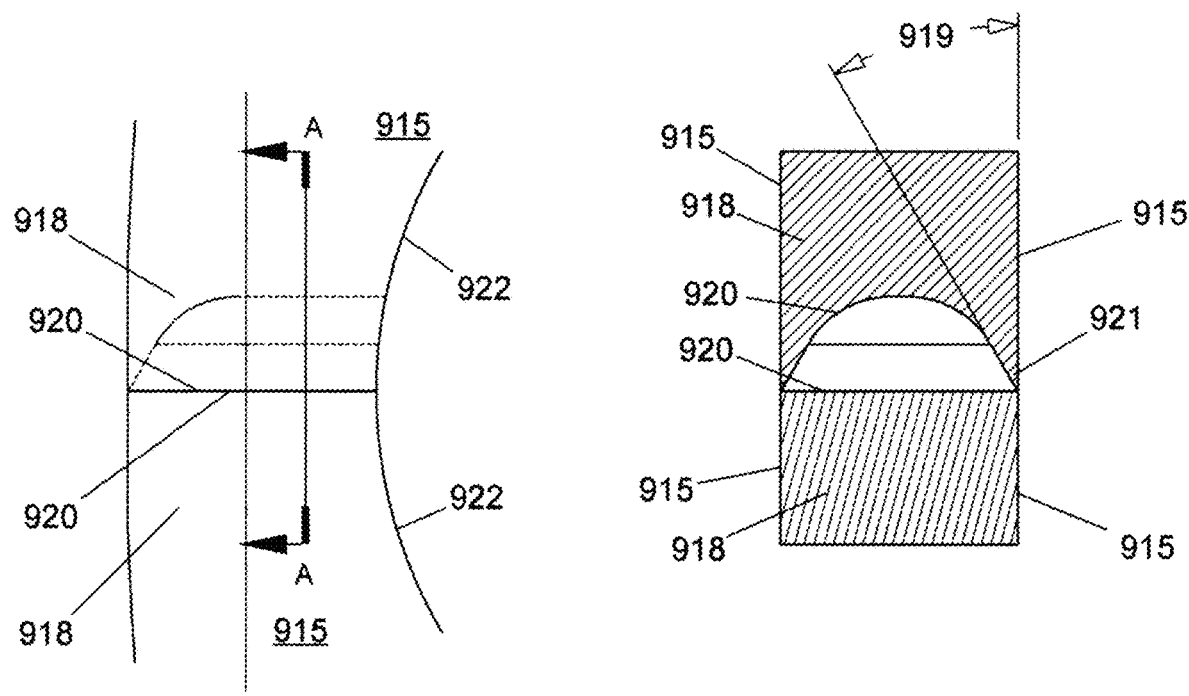
Fig. 103
Fig. 104

SIMPLIFIED VASECTOMY METHODS

PRIORITY

The instant application is a continuation of U.S. patent application Ser. No. 18/341,375 filed Jun. 26, 2023 (now U.S. Pat. No. 11,844,540), which, in turn, is a continuation of U.S. patent application Ser. No. 17/709,675 filed Mar. 31, 2022 (now U.S. Pat. No. 11,723,680), which, in turn, is a continuation-in-part of U.S. patent application Ser. No. 16/700,393 filed Dec. 2, 2019 (now U.S. Pat. No. 11,291,581), which, in turn, claims the benefit of U.S. Provisional Application Ser. No. 62/917,325 filed Dec. 3, 2018.

U.S. patent application Ser. No. 17/709,675 filed Mar. 31, 2022 (now U.S. Pat. No. 11,723,680) is also a continuation-in-part of U.S. patent application Ser. No. 17/338,115 filed Jun. 3, 2021 (now U.S. Pat. No. 11,291,493), which, in turn, is a continuation-in-part of U.S. patent application Ser. No. 17/150,313 filed Jan. 15, 2021 (now abandoned), which, in turn, both claims the benefit of U.S. Provisional Application Ser. No. 62/995,188 filed Jan. 16, 2020 and is a continuation-in-part of U.S. patent application Ser. No. 16/700,393 filed Dec. 2, 2019 (now U.S. Pat. No. 11,291,581), which, as noted above, claims the benefit of U.S. Provisional Application Ser. No. 62/917,325 filed Dec. 3, 2018.

The contents of these prior applications are hereby incorporated by reference in their entirety.

TECHNICAL FIELD OF THE INVENTION

The present invention relates to surgical instruments, and more particularly to bipolar surgical instruments and kits for performing vasectomies and methods for performing vasectomies using the instruments and kits.

BACKGROUND OF THE INVENTION

Vasectomy is a surgical procedure that typically involves the removal of a portion of the ducts that carry sperm out of the testes (i.e., the vas deferens), thereby stopping the flow of sperm from the testicle to the prostate gland; once the vas deferens is interrupted, the sperm cannot be delivered and the man is rendered sterile. Currently used vasectomy methods, such as the No Scalpel Vasectomy ("NSV"), require that each vas deferens be dissected from the scrotum to allow the clinician to occlude and divide the vas duct. Therein, the vas deferens is isolated, extracted, or otherwise delivered from the scrotum via one or two openings formed by puncturing the scrotum and then expanding the opening(s). The vas sheath is then retracted from a portion of the vas duct, which is then hemi-dissected and occluded, preferably by means of mucosal cautery in which the distal end of the filament of a battery powered cautery unit is inserted into each duct lumen and energized so as to create a luminal plug of scar tissue. Alternatively, vas occlusion may involve ligation with a suture or surgical clip. In either case, after the vas is divided, a portion of the duct is optionally excised and one end is isolated in the vas sheath to create a barrier to reconnection of the duct. For example, a layer of the vas sheath may be placed between the two severed ends of the vas duct in order to cover one end but not the other in a technique referred to as "fascial interpositioning". Once both ends are sufficiently secured, the duct is then returned to the scrotum, and the opening through which the vas was accessed is allowed to close, and the procedure is deemed complete. Optionally, a stitch or skin adhesive is used to aid in closure.

While the procedure appears simple, significant surgical skill is required, and complications may result. Most common of these is the arisal of hematomas caused by slow bleeders at the site of the duct occlusion and division. In non-elastic tissue, a small amount of bleeding is quickly stopped by the tension that develops in the tissue. However, because the scrotum is essentially an elastic balloon-like vessel, the hydrostatic pressure necessary to stop bleeding is not present. Accordingly, even the slightest amount of persistent bleeding can cause a tremendously large hematoma. In a similar manner, rough handling of the tissue can lead to significant swelling. Even the most experienced vasectomy surgeon will occasionally encounter these problems.

Other disadvantages inherent in conventional surgical vasectomy, as exemplified by the NSV, include the prolonged surgical duration, which is generally on the order of twenty minutes or more. In addition, conventional vasectomy procedures fail to adequately account for the natural tendency of the cut ends of the vas deferens to grow back together, thereby allowing the flow of sperm to the prostate and resumption of fertility. Means for avoiding this failure have been the subject of debate among those skilled in the art, the question being whether the vas deferens should be clipped, cut, cauterized, ligated, or all of the above. Finally, because sharp instruments are used, performing a vasectomy on HIV+ patients presents a risk to the surgeon.

U.S. Pat. Nos. 8,220,464 and 8,561,615, both to Pannell et al. represents an attempt to address the afore-noted drawbacks. Therein, Pannell et al. describe an instrument and method that overcomes some of these disadvantages of conventional vasectomy techniques, more particularly a bipolar coagulating device able to occlude a vas duct in situ, without dissecting the duct from the scrotum. In a preferred embodiment, the coagulating device includes an integral cutting element able to excise a portion of scrotal tissue. In the context of the Pannell method, a vas duct is located in a fold of scrotal skin and maintained in that location by a clamp made of a dielectric material. The arcuate jaws of the bipolar coagulating device are positioned around the clamp so as to compress a similarly arcuate region of tissue between the jaws. The arcuate clamped region contains two portions of the vas duct trapped in the fold of scrotal tissue. After coagulating the arcuate clamped region, the clamp is removed so as to allow an integral cutting element pivotably mounted to the bipolar device to excise the uncoagulated tissue in the center of the arcuate region. Thus, the excised tissue contains the uncoagulated portion of the vas duct between the two coagulated regions sealed in the coagulated tissue fold.

The method described by Pannell et al. has significant advantages over other vasectomy methods. For example, because there is no dissection, there can be no bleeders and therefore no hematomas. Additionally, as the procedure has fewer steps, it can be completed in much less time. Finally, extensive surgical skills are not required. However, due to the inclusion of an integral excision element, the Pannell device tends to be complex, particularly if excision of the tissue is to be accomplished electrosurgically, as is the preferred embodiment. Also, when occluding a vas duct by the Pannell method, the clamp that maintains the position of the duct in the fold and locates the fold in the jaws of the coagulating device must be removed before excising the tissue portion. Removal of the clamp may allow the coagulated tissue to be displaced in the jaws before or during excision of the tissue. Accordingly, it may be necessary for the clinician to exercise extreme care since displacement of the tissue may result in incomplete excision of the uncoagulated central tissue portion. Given that tissue shrinks and forms a smooth lubricious surface when coagulated, such displacement may readily occur.

The present invention builds and improves upon the teachings of Pannell et al. described in U.S. Pat. Nos. 8,220,464 and 8,561,615, the contents of which are incorporated by reference herein. In particular, the present invention is intended to simplify the vasectomy process so as to allow those less skilled to perform the procedure, as well as to overcome existing disadvantages and deficiencies in the prior art including, but not limited to, a substantial risk for the development of hematomas and swelling, and a need for a highly skilled surgical professional, as well as a long recovery period, accompanied by severe limitations on post-surgical activity.

Accordingly, the present invention addresses an ongoing need in the art for vasectomy methods that utilize simplified instruments to occlude and divide a vas duct simply and quickly and with fewer steps and fewer post-surgical complications. To that end, the present invention further addresses the need in the art for expeditious vasectomy methods that prevent hematomas and swelling, that minimize the potential for spontaneous regeneration and undesired resumption of fertility, that negate the need for a highly skilled surgical professional, an extended procedure duration, and a prolonged recovery time. Finally, the present invention addresses the desire in the art for such new methods to avoid the need for sharp instruments so that clinicians may limit their exposure to a patient's body fluids and thus operate on patients with infectious diseases such as HIV without risk of infection.

SUMMARY OF THE INVENTION

The present invention addresses the afore-noted needs in the art by providing both novel vasectomy devices and instruments and novel methods for their use. For example, through the use of the excising instruments of the present invention, together with a bipolar coagulating device in methods of the present invention, a vas duct may be quickly and simply occluded, divided, and separated by fascial interposition. For example, in a first embodiment, the present invention provides a novel vasectomy method in which the requisite operations are accomplished in a single step, after the duct is dissected from the scrotum. In a second, alternative embodiment, the present invention allows for these operations to be accomplished in a single step without removing the duct from the scrotum. Further illustrative aspects and embodiments of the present invention in accordance with the foregoing objectives are as follows:

It is an objective of the present invention to provide a bipolar vasectomy device and surgical method for vasectomy in which the vas is located in a conventional manner and anesthetized using a local anesthetic. Thereafter, the scrotum is punctured in accordance with standard procedures, for example, using a dissecting forceps, and expanded to allow insertion of either an "excising clamp" or "excising hook" of the present invention, i.e., instruments used to position a vas duct within the coagulating jaws of a bipolar electrosurgical device of the present invention, to maintain that position during coagulation, and thereafter to optionally divide the vas by excision.

In the context of a first embodiment, the bipolar vasectomy device and vasectomy method of the present invention involves the capture of the vas using one of the novel excising clamps or hooks of the present invention and the subsequent delivery of the vas out of the scrotum a sufficient distance to allow the arcuate jaws of an improved bipolar coagulating device described in detail herein to be positioned around the hook or clamp. In the context of the present invention, the tissue is secured between the angularly offset, U-shaped cutting jaws of a coagulating device such as exemplified in FIG. 25 and radio frequency (RF) energy is supplied for a brief period, on the order of 10 to 20 seconds, so as to thermally coagulate portions of the vas between the arcuate jaw portions. When coagulation is complete, the excising clamp or hook is moved downward, upward, or at an angle relative to the U-shaped jaws of the coagulating device so that the portion of the vas captured within an interior surface of the clamp or hook is excised. Excision is accomplished by the cooperative action of the cutting edges on the jaws of the improved coagulating device and the sharp edges on the excising clamp or hook. Sealing of the duct, sealing of the sheath, and dividing of the vas are all accomplished in two simple steps that do not require surgical skill. Thus, the opportunity for hematoma creation is dramatically reduced.

In certain optional embodiments, the vas may be delivered from the scrotum by a conventional surgical instrument such as, for instance, a ring clamp or dissecting clamp, and subsequently transferred to a dissecting clamp of the present invention for positioning in the jaws of the bipolar vasectomy device.

In other optional embodiments, the portion of the vas captured within the interior region of the clamped, U-shaped jaws of the bipolar vasectomy device may be excised after coagulation by means of an alternative cutting instrument conventional in the surgical arts, examples of which include, but are not limited to, a scalpel, dissecting forceps, scissors or other surgical device.

In the context of an alternative embodiment, the bipolar vasectomy device and vasectomy method of the present invention avoids the need for dissecting the vas from the scrotum. In this alternative scenario, after the duct is isolated in a fold of scrotal tissue, an excising clamp of the present invention is applied to the fold medial to the duct so as to maintain the position of the duct. Once again, the arcuate jaws of a bipolar coagulating device in accordance with the present invention are then positioned around the clamp so as to compress an arcuate region of tissue between the jaws. This arcuate region contains a portion of the duct positioned within a portion of the fold of scrotal tissue by the excising clamp. This arcuate region is then coagulated by means of the RF energy supplied to the jaws by an electrosurgical generator. When coagulation is complete, the excising clamp is displaced upward, downward, or angularly relative to the jaws so as to excise the central uncoagulated tissue portion bound by the arcuate coagulated region clamped between the jaws of the coagulating device. Excision is accomplished by interaction between cutting edges formed on the jaws of the coagulating device and cutting edges formed on the jaws of the clamp. Further exemplary details and illustrations of this alternative intra-scrotal procedure may be found in co-pending U.S. patent application Ser. No. 17/338,115 referenced above, the contents of which are incorporated by reference herein in their entirety.

In certain optional embodiments, the portion of the vas captured within the interior region of the clamped, U-shaped jaws of the bipolar vasectomy device may excised after coagulation using an alternative conventional cutting instrument conventional in the surgical arts such as mentioned above, examples of which include a scalpel, dissecting forceps, scissors, biopsy punch, or other surgical device. As noted above, the present invention is one aspect relates to the provision of a variety of novel surgical instruments suitable for use in connection with the above-mentioned vasectomy methods and improved bipolar coagulating device, more particularly in the form of novel excising hooks and clamps adapted and suitable for isolating and excising a portion of the vas deferens targeted for removal.

In one aspect, the surgical instrument provided by the present invention is an excising hook that resembles a shepherd's crook, as exemplified in FIG. 37. In a preferred embodiment, the excising hook is composed of an elongate shaft having a thickened proximal portion and a narrowed distal end that curves back on itself to form a circular hook. In a preferred embodiment, the circular hook is formed of suitable dielectric material and is sized to slidably fit within the U-shaped jaws of the bipolar coagulating device of the present invention. Likewise, the interior surfaces of the hook are suitably sharpened so as to cooperate with the cutting jaws of the bipolar coagulating device to thereby enable removal of a portion of uncoagulated tissue containing an excised length of the vas duct.

In another aspect, the surgical instrument provided by the present invention is an excising clamp in the form of a pair of eyelet forceps, such as exemplified in FIG. 11, that includes a proximal handle portion provided with a pair of "finger grips" or "finger holes" that drive a pair of hinged arms that, in turn, define the longitudinal axis of the device, and a ratchet mechanism that enables the hands-free maintenance of the arms, and their respective distal tissue-gripping portions, in a locked configuration. Disposed distally along the respective arms, past a pivoting hinge, the tissue-gripping portions of this novel, excising clamp comprise a pair of mating semi-circles that together circumscribe a small hole or eyelet that, in operation, becomes disposed about the portion of the vas duct being excised. As noted above, the distal end tissue-gripping portions are provided with sharpened interior edges that enable removal of an uncoagulated vas tissue through cooperative action with the cutting jaws of the bipolar coagulating device as described above.

In yet a further aspect, the surgical instrument provided by the present invention is an excising clamp in the form of a slidable assembly as illustrated in FIG. 57. In a preferred embodiment, the slidable clamp assembly is composed of two pieces, namely an elongate generally U-shaped clamp body and a slidable control ring, assembled into a single unit that is suitable for isolating and excising an uncoagulated portion of a vas duct. In the context of the present invention, the elongate clamp body is made up of a proximal handle portion that, proceeding distally, splits for form a pair of elongate movable pincer arms that take the form of two relatively parallel intermediate portions (upper and lower) that, in turn, terminate in opposed distal portions (upper and lower), each of which is provided a distal-most portion that takes the form of a symmetrically opposed jaw. Each opposed jaw is a mirror image of the other, or has an otherwise form complementary to the other, and includes a sharp distal tip projecting towards an interior surface of the assembly.

In a particularly preferred embodiment, the elongate clamp body further includes a pair of proximal stops, a first positioned along the exterior surface of the upper intermediate portion and a second positioned at an equivalent point along the exterior surface of the lower intermediate portion, and a pair of distal stops, a first positioned along the exterior surface of the upper distal portion and a second positioned at an equivalent point along the exterior surface of the lower distal portion, such that the spacing between the upper proximal and distal stops is identical to the spacing between the lower proximal and distal stops.

The afore-mentioned slidable control ring is provided with a central opening that allows it to be disposed about the periphery of the elongate body and slide along the spacing between respective proximal and distal stops. When the slidable control ring is positioned adjacent the proximal stops, in a proximal-most position, the opposed upper and lower distal jaws remain in the "open" (unclamped) configuration. However, distal movement of the slidable control ring forces the upper and lower distal portions to deflect inward, moving the respective sharp distal tips toward contact. When the slidable control ring encounters the distal stops, it arrives at a distal-most position in which the distal portions of the opposed distal jaws meet, i.e., are moved into close proximity, or optionally in contact close form a "closed" (clamped) configuration.

In a preferred embodiment, both the excising clamp body and slidable control ring are formed of a suitable dielectric material, preferably from a polymeric material by injection molding or other suitable process.

In yet another aspect, the surgical instrument provided by the present invention is forceps-like clamp as exemplified in FIG. 86. Similar to the eyelet clamp described above, this excising clamp resembles a pair of scissors or forceps, including a proximal handle portion provided with a pair of "finger grips" or "finger holes" that drive a pair of hinged blades that define the longitudinal axis of the device and a ratchet mechanism that enables the hands-free maintenance of the blades, and their respective distal jaw portions, in a locked configuration. Disposed distally along the respective blades, past a pivoting hinge, the jaws of this alternate excising clamp are preferably defined by two relatively parallel, planar, and laterally opposed portions (upper and lower), each of which is provided with a distal-most vertically opposed portion (upper and lower) that is relatively perpendicular to the longitudinal axis of the device. Upper and lower laterally opposed portions comprise symmetrical mirror images; likewise, upper and lower vertically opposed portions are also symmetrically disposed. In the context of the present invention, pivoting the hinged blades brings the upper and lower vertically opposed portions into contact, such that their respective terminal surfaces come into contact to form a sharp cutting edge. In the context of the present invention, the respective terminal surfaces (and corresponding cutting edges) may be planar, mirror-image serrated or complementary serrated. As in previously described embodiments, the sharpened surfaces of the excising clamp cooperate with the cutting jaws of the bipolar coagulating device to thereby enable removal of a portion of uncoagulated tissue containing an excised length of the vas duct.

As noted above, the present invention is characterized by substantial advantages not found in conventional methods and devices. For example, by avoiding direct dissection and resulting bleeding, the present invention is able to minimize or preferably eliminate the risk for the development of massive hematomas and swelling. In addition, the present invention allows for the separation of the vas deferens in such a manner that it is virtually impossible for the ends of the vas deferens to contact each other and rejoin. Also, as compared to vasectomy methods currently available, the inventive procedure utilizes significantly fewer surgical steps and thereby reduces the opportunity for complications. The inherent simplicity of the disclosed procedures and associated instruments simplifies training and allows clinicians with limited experience to master their use. Moreover, the procedures of the present invention minimize or even avoid exposure to bodily fluids, which, in turn, significantly reduces risks of transmission of blood-born diseases, such a HIV and Hepatitis, to performing clinicians.

These and other objectives can be accomplished by the invention herein disclosed. Further objects and features of the invention will become more fully apparent when the following detailed description is read in conjunction with the accompanying figures and examples. To that end, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. In addition, regarding the specific objectives recited above, it will be understood by those skilled in the art that one or more aspects of this invention can meet certain objectives, while one or more other aspects can meet certain other objectives. Each objective may not apply equally, in all its respects, to every aspect of this invention. As such, the objectives herein can be viewed in the alternative with respect to any one aspect of this invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 16 is a plan view of a bipolar electrosurgical device of a vasectomy system of the present invention.

FIG. 17 is a side elevational view of the objects of FIG. 16.

FIG. 57 is a plan view of an alternate embodiment for an excising clamp body in accordance with the present invention.

FIG. 58 is a side elevational view of the objects of FIG. 57.

FIG. 65 is a plan view of an excising clamp in accordance with the present invention, formed of the clamp body of FIG. 57 and the clamp ring of FIG. 62 with the clamp in a first, open/unclamped condition.

FIG. 66 is a side elevational view of the objects of FIG. 65.

FIG. 68 is a plan view of the alternate excising clamp of FIG. 65 in a second closed/clamped condition.

FIG. 69 is a side elevational view of the objects of FIG. 68.

FIG. 99 is a perspective view of the alternate excising clamp of FIG. 98 in which the modified jaws are depicted in the open (unclamped) condition.

FIG. 100 is a side elevational view of the distal portion of yet another excising clamp of the present invention analogous to that depicted in FIG. 86 in which the jaws of the distal clamping portion (depicted in the closed (clamped) condition) are modified to include complementary cylindrical surfaces.

FIG. 101 is a perspective view of the alternate excising clamp of FIG. 100 in which the modified jaws are depicted in the open (unclamped) condition.

FIG. 102 is a side elevational view of yet another excising clamp of the present invention analogous to that depicted in FIG. 86 in which the jaws of the distal clamping portion (depicted in the closed (clamped) condition) are modified to include complementary beveled surfaces.

FIG. 103 is an expanded view of the objects of FIG. 102 at location D.

FIG. 104 is a sectional view of the objects of FIG. 103 at location A-A.

FIG. 105 is a perspective view of the objects of FIG. 102 with the modified jaws of the clamp in an open (unclamped) condition.

FIG. 106 is an expanded view of the objects of FIG. 105 at location E.

FIG. 107 is a perspective view of the clamp of FIG. 2 positioned on a scrotum when coagulation of the site is completed according to the principles of the present invention.

FIG. 108 is an expanded view of the objects of FIG. 107 at location A.

FIG. 109 is a perspective view of yet another excising clamp of the present invention analogous to that depicted in FIG. 86 in which the distal clamping portion (with jaws depicted in the open (unclamped) condition) is modified to include low included angle edges.

FIG. 110 is an expanded view of the objects of FIG. 107 at location F.

DETAILED DESCRIPTION OF THE PREFERRED EMBODIMENTS

Figure 1:
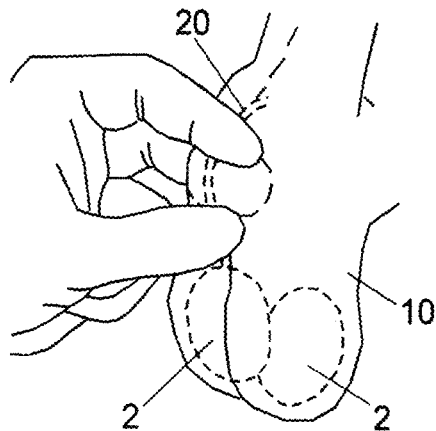
FIG. 1 depicts a first step in a prior art No Scalpel Vasectomy (NSV) procedure in which a vas duct is located in a fold of scrotal tissue.

Before the present materials and methods are described, it is to be understood that this invention is not limited to the specific devices, systems, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

As used herein, the noted directional terms relate to a human body in a standing position. For instance, "up" refers to the direction of the head, "down" refers to the direction of the feet. Likewise, herein, the "vertical" direction is parallel to the axis of the body and the "horizontal" direction is parallel to the floor. In a similar fashion, the term "lateral" refers to the direction extending away from the center of the body whereas "medial" refers to a direction extending toward the center of the body.

In the context of the present invention, the term "proximal" refers to that end or portion of a device or instrument which is situated closest to the body of the subject when the device is in use. Accordingly, the proximal end of an excising clamp or bipolar electrosurgical device of the present invention includes the handle portions.

In the context of the present invention, the term "distal" refers to that end or portion of a device or instrument that is situated farthest away from the body of the subject when the device is in use. Accordingly, the distal end of an excising clamp of the present invention includes the jaw components.

In the context of the present invention, the term "arcuate" is used herein to describe shapes forming or resembling an arch. It is used interchangeably with its synonym, arciform. Reference is made herein to "an arcuate sealed area" that contains one or more portions of the vas duct and a portion of its surrounding sheath. This "arcuate" area is exemplary only and not meant to be limiting. The sealed area may have a variety of regular or irregular shapes. Any sealed area formed by bipolar jaws positioned distal to a clamp located on the vas duct within the sheath falls within the scope of this invention. The sealed region may be arcuate, linear, irregularly shaped, or a combination of linear and curvilinear segments.

In describing some embodiments of methods of the present invention reference is made to the placement of a clamp on the midline of a vas duct within a vas sheath. It will be understood that such placement is imprecise and the midline of the clamping surface need not be on the exact midline of the duct. So long as a portion of the clamping surface of the clamp is closed upon a middle portion of the vas duct while minimizing contact with the distal region of the sheath, the method falls within the scope of this invention. In other embodiments, a clamp is configured such that the distal clamping surfaces may be positioned distal to the vas duct within the vas sheath. In these embodiments the clamp distal portion and bipolar jaws of the sealing device are configured so as to minimize their effect on nerves located in the sheath distal to the vas duct and therefore fall within the scope of this invention.

In the context of present invention reference invention, the terms "coagulated" or "cauterized" are interchangeably used to describe a treated area of tissue. As used herein, coagulated or cauterized tissue is tissue that through the application of RF energy and pressure has been desiccated and fused to eliminate the flow of blood or other fluids.

In the context of the present invention, the term "convex" refers to a surface or boundary that curves outward, as the exterior of a sphere. Conversely, the term "concave" refers to a surface or boundary that curves inward, as to the inner surface of a sphere, or is hollowed or rounded inward like the inside of a bowl. Herein, the area of unclamped vas tissue defined by the U-shaped jaws of the bipolar coagulating device and the arcuate area of clamped vas tissue contained therein is referred to as convex in shape.

In the context of the present invention, the terms "vas" and "vas deferens" are used interchangeably to refer to the coiled biological channel that conveys sperm from the epididymis to the ejaculatory duct and the urethra that is comprised of an inner tubular duct (i.e., the "vas duct") and an outer muscular sheath (i.e., the "vas sheath").

In the context of the present invention, the terms "duct" and "vas duct" are used interchangeably to refer to the interior channel of vas deferens that serves to as a conveyance for sperm. Likewise, the terms "sheath" and "vas sheath" are used interchangeably to refer to the amorphous muscular sheath that surrounds the vas duct and houses the bulk of the sensory nerves.

The instant invention makes reference to certain surgical instruments that are configured for both clamping tissue or capturing a vas duct and for excision as well. Such instruments, often referred to herein as "excising" or "excision" clamps or hooks, are designed for use in conjunction with the bipolar coagulating device of the present invention to facilitate the vasectomy methods of the present invention, namely, to position a vas duct within the jaws of the bipolar coagulating device, to maintain that position during coagulation, and thereafter to optionally divide the vas by excision.

In order to prevent shorting of the jaws of the bipolar coagulating device of the present invention, such clamping devices are formed from a dielectric material, typically a polymer or ceramic, or are formed of a metallic material and are covered with a dielectric coating. While specific embodiments are described herein, it should be understood that clamps having a wide variety of configurations may be used, including, for example, standard metal ring forceps and tenaculum to which a non-conductive coating has been applied.

As noted above, the present invention is characterized by substantial advantages not found in conventional methods and devices. For example, in the context of the present invention, nerves in the sealed region and closely adjacent thereto are destroyed or deadened by a process known as RF neurotomy so as to reduce the probability of post procedure pain. In addition, in those embodiments that avoid direct dissection and resulting bleeding, the present invention is able to eliminate the risk for development of massive hematomas and swelling. In addition, the present invention allows for the separation of the vas deferens in such a manner that it is virtually impossible for the ends of the vas deferens to contact each other and rejoin. Also, the vasectomy procedure of the present invention requires fewer steps than for current vasectomy techniques thereby reducing opportunities for complications and medical errors. Furthermore, the inherent simplicity of the disclosed procedure and associated instruments simplifies training and allows clinicians with limited experience to master their use. Moreover, the procedures of the present invention reduce exposure to bodily fluids, which, in turn, reduces the risks of transmission of blood-borne diseases, such a HIV and Hepatitis, to performing clinicians.

Although methods and materials similar or equivalent to those described herein can be used in the practice or testing of embodiments of the present invention, the preferred methods, devices, and materials are depicted in the accompanying figures and described hereinafter. However, the embodiments described herein are merely intended to illustrate the principles of the invention.

Those skilled in the art will recognize that variations and modifications may be made to the embodiments without changing the principles of the invention herein disclosed. Accordingly, the accompanying figures, described in detail below that depict aspects of the invention are in no way intended to limit the scope of the present invention.

EXAMPLES

Figure 2:
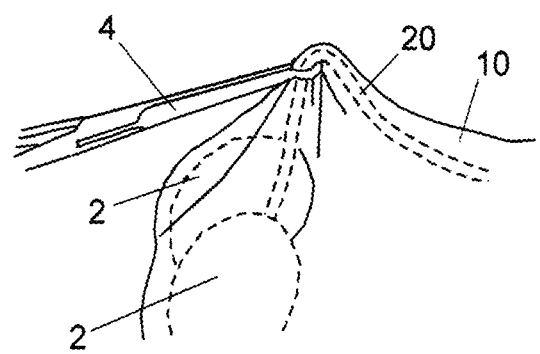
FIG. 2 depicts a subsequent step in the prior art NSV procedure in which the vas duct is isolated in a fold of scrotal tissue using a ringed clamp.
Figure 3:
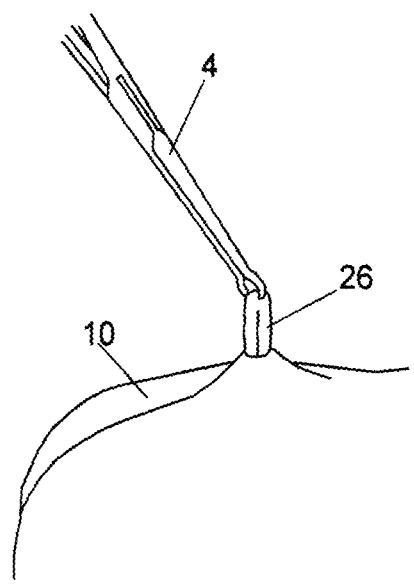
FIG. 3 depicts a subsequent step in the prior art NSV procedure in which an opening is formed in the scrotum and a portion of a vas duct in its surrounding sheath is extracted from the scrotum.
Figure 4:
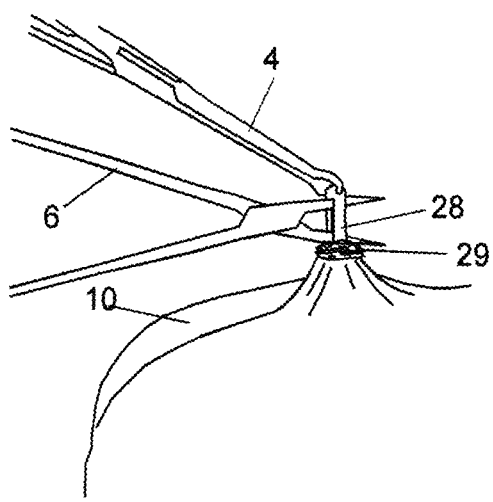
FIG. 4 depicts a subsequent step in the prior art NSV procedure in which the vas sheath is stripped back from the vas duct in preparation for occlusion.
Figure 5:
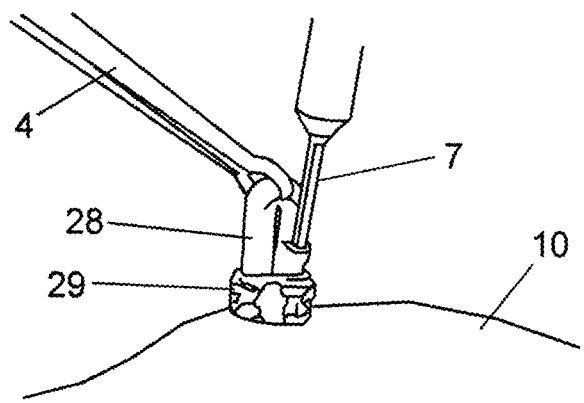
FIG. 5 depicts a subsequent step in the prior art NSV procedure in which a first side of the hemi-dissected vas duct is coagulated using a cautery.
Figure 6:
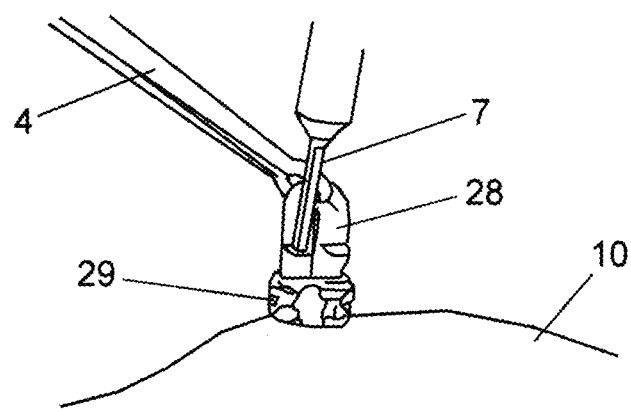
FIG. 6 depicts a subsequent step in the prior art NSV procedure in which a second side of the hemi-dissected vas duct is coagulated using a cautery.
Figure 7:
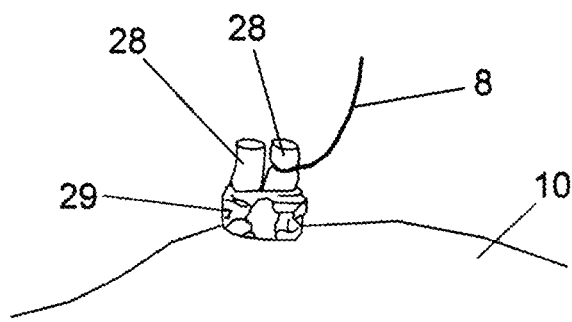
FIG. 7 depicts the vas duct after subsequent removal of the portion medial to the dissections in the prior art NSV procedure, with the end of the prostate leg ligated and the suture left untrimmed.
Figure 8:
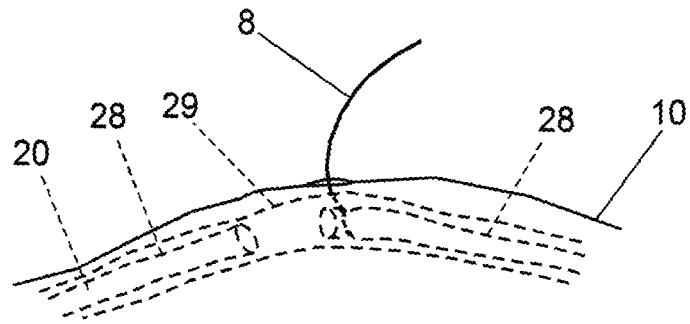
FIG. 8 depicts the site subsequent to FIG. 7, wherein the ends of the vas enclosed in the sheath are returned to the scrotum with the leg of the ligating suture extending from the puncture in the scrotum.
Figure 9:
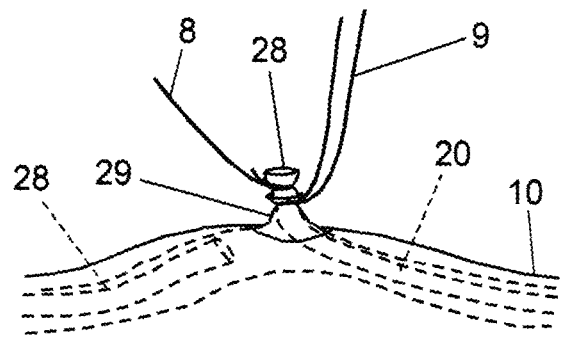
FIG. 9 depicts the site subsequently to FIG. 8, with the end of the prostate leg of the vas duct secured outside of the vas sheath so as to establish fascial interposition.
Figure 10:
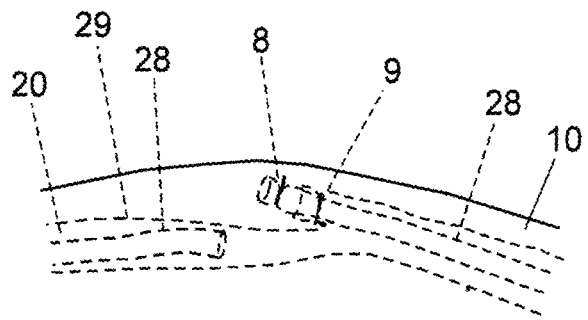
FIG. 10 depicts the site at completion of occlusion of the duct via the prior art NSV procedure in which the ends of the duct returned to the scrotum.
Figure 11:
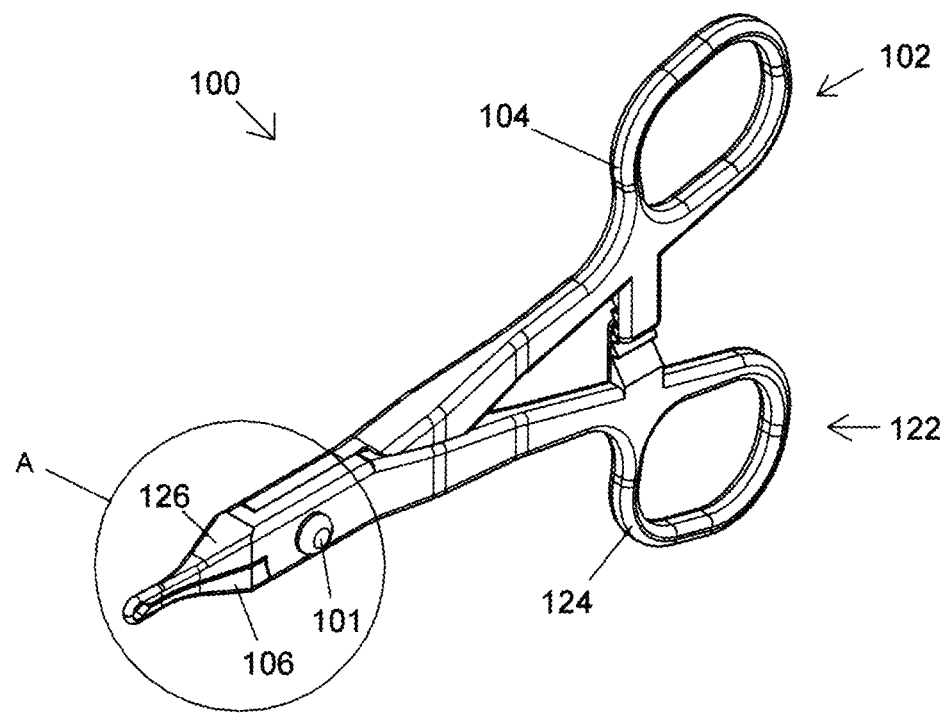
FIG. 11 is a perspective view of an excising clamp of the present invention.
Figure 12:
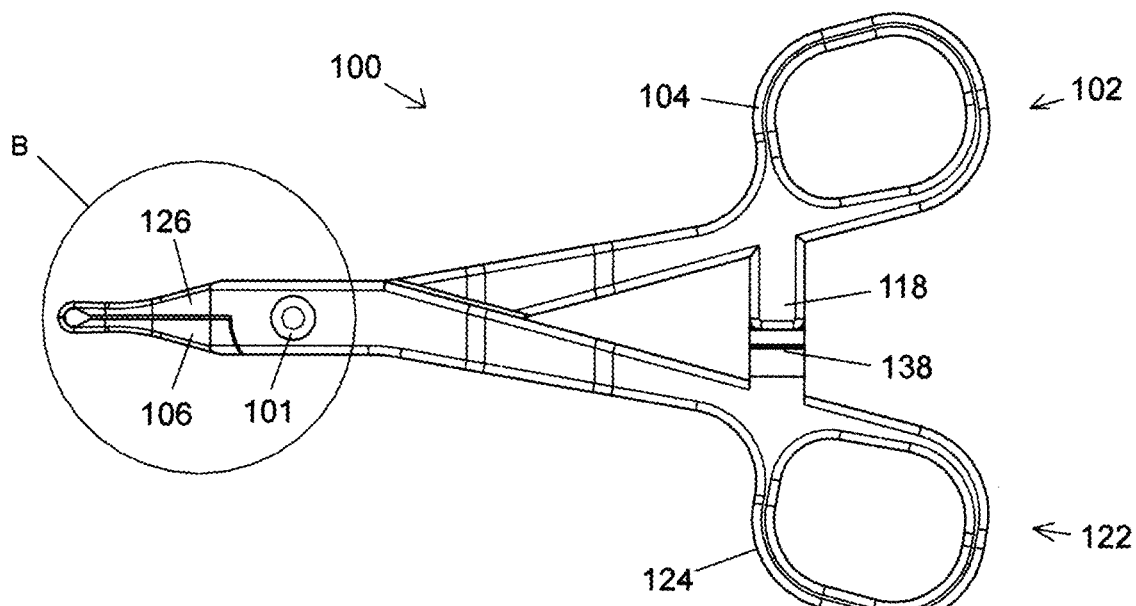
FIG. 12 is a side elevational view of the clamp of FIG. 11.
Figure 13:
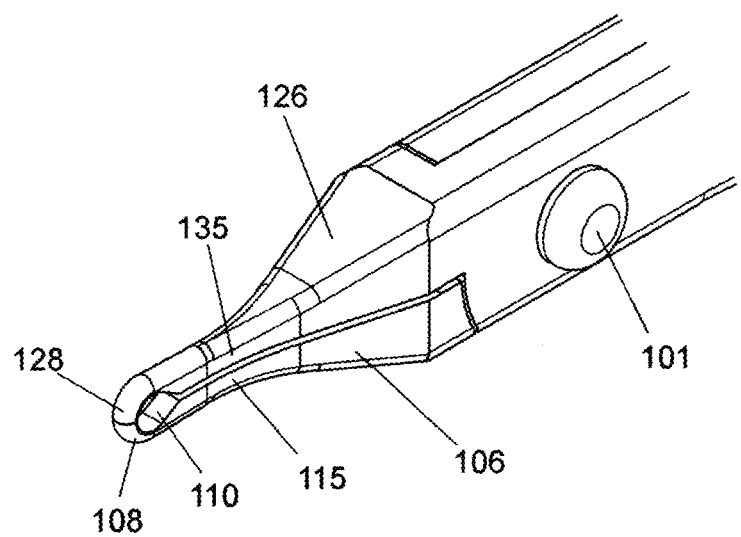
FIG. 13 is an expanded view of the clamp of FIG. 11 at location A.

The most common method of vasectomy currently practiced is the No-Scalpel Vasectomy ("NSV") in which the vas deferens is delivered from the scrotum via one or two openings formed by puncturing the scrotum and then expanding the opening(s). Steps of a typical prior-art NSV wherein a vas duct is occluded are depicted in FIGS. 1 through 10. In FIG. 1, a vas duct 20 is located in scrotum 10 using a standard technique. Thereafter, a local anesthetic is injected at the site. Duct 20 is then located in a fold of scrotum 10 using a ringed forceps 4 as shown in FIG. 2. The scrotum is then punctured using a dissecting forceps and the opening expanded sufficiently to allow the surgeon to deliver a portion 26 of vas duct 20 as depicted in FIG. 3. Dissecting forceps 6 are then used to puncture vas sheath 29 and then strip sheath 29 back to expose duct portion 28 as shown in FIG. 4. In FIGS. 5 and 6, duct portion 28 is hemi-dissected into abdominal and testicular portions, after which the distal element of an electrocautery 7 is inserted into the lumens of the respective portions and activated so as to form scar tissue in the lumens and thereby occlude them. Thereafter, as shown in FIG. 7, a suture 8 is applied to the abdominal leg of the separated duct portion 28. Next, vas sheath 29 with the testicular portion of separated duct 28 are drawn back into scrotum 10 with suture 8 extending through the opening in sheath 29 and the opening in scrotum 10 as shown in FIG. 8. In FIG. 9, suture 8 is used to draw duct 28 and sheath 29 out of scrotum 10, and to draw the abdominal side occluded end of duct 28 out of sheath 29, whereupon suture 10 is tied around a portion of sheath 28 and duct 29 as depicted in FIG. 9. Placing suture 9 in this manner permanently places a wall of sheath 29 between the divided occluded ends of duct 28 so as to provide an additional barrier to reuniting of the divided ends. FIG. 10 depicts the site with occluded, divided vas duct 20 returned to scrotum 10 with the duct ends being separated by fascial interpositioning.

As discussed elsewhere herein, the NSV procedure has multiple steps and requires extensive surgical skills. Completing the procedure generally requires twenty minutes or more. If the surgeon fails to notice and address any bleeders, hematomas may result. Because the scrotum is a flexible expandable vessel, these hematomas may become massive, resulting in pain and anxiety for the patient. In all cases it is necessary for the patient to restrict activities following the procedure, frequently for a week or more.

Devices and methods of the present invention enable a clinician to perform an NSV procedure in less time and with a decreased likelihood of complications. To that end, in the current NSV technique, occluding of the duct, dividing of the duct, and creating the fascial interposition are accomplished in three separate steps. However, using devices and methods of the present invention, these three tasks may be accomplished in a single step. Namely, the vas duct and its surrounding sheath are captured in an excising clamp or excising hook of the present invention and delivered from the scrotum. While remaining contained and isolated in the clamp or hook, the duct and its surrounding sheath are grasped between the jaws of a modified version of a bipolar coagulating device such as described in U.S. Pat. Nos. 8,220,464 and 8,561,615, the contents of which are enumerated and incorporated above, and sealed using RF energy. Thereafter, the duct is divided by excision using one of the novel excising clamps or excising hooks of the present invention or another surgical instrument before releasing the jaws of the coagulating device. In contrast with the conventional art-accepted NSV technique, stripping of the vas sheath, occlusion of the duct by cautery or ligation, and creating fascial interpositioning of the sheath as discrete steps by the surgeon are not required. Thus, as less surgical skill is required, the procedure may be performed by a non-surgeon on the medical staff, for example, a nurse, nurse practitioner, or physician's assistant.

The inventive method and novel excising clamps and hooks are now described. To that end, a first iteration of an excising clamp 100 of the present invention is depicted in FIGS. 11 through 15. Excising clamp 100 has a first element 102 with a proximal handle portion 104 and a distal portion 106, and a second element 122 with a proximal handle portion 124 and a distal portion 126, elements 102 and 122 being rotatably affixed by element 101. First element 102 has formed near its proximal end first ratchet portion 118. Second element 122 has formed near its proximal end second ratchet portion 138. Ratchet elements 118 and 138 cooperatively, when engaged, maintain closure and tension of clamp 100 during use. Distal portion 106 of first element 102 has formed at its distal end arcuate first jaw 108. Distal portion 126 of second element 120 has formed at its distal end arcuate second jaw 128. When in the closed position, inner surfaces 110 and 130 of jaws 108 and 128 respectively circumscribe eyelet 103 proximal to jaws 108 and 128. Laterally opposed planar surfaces 115 of lower jaw 108 and 135 of upper jaw 128 intersect with surfaces 110 and 130 respectively to form sharp edges perimetral to opening 103 (see FIG. 14B). When viewed in plan view, as in FIG. 15, jaws 108 and 128 together with proximally adjacent portions of distal portions 106 and 126 have width 116. Excising clamp 100 is formed of a suitable dielectric material. In a preferred embodiment, clamp 100 is formed of a polymeric material formed by injection molding.

Excising clamp 100 is configured for removal of an uncoagulated tissue portion by cooperative action of clamp 100 and the jaws of a bipolar coagulating device configured for this purpose. The bipolar coagulating device (handpiece) 400 of the present invention depicted in FIGS. 16 through 20 with the jaws in a first, clamped position is substantially similar to the equivalent electrosurgical device described in U.S. Pat. No. 8,561,615 and operates by an analogous procedure. To wit, bipolar handpiece 400 has an upper handle assembly 402 with a proximal handle portion 404 and a distal portion 406 wherein is mounted lower jaw 408. Handpiece 400 has a lower handle assembly 422 with a proximal handle portion 424 and a distal portion 426 wherein is mounted upper jaw 428. Upper handle assembly 402 and lower handle assembly 422 are rotatably joined by element 401. Lower handle assembly 422 has located adjacent to its proximal end ratchet element 430 that, in cooperation with downward extending proximal portion 410 of upper handle assembly 402 maintains the clamping force of jaws 408 and 428, portion 432 of ratchet element 430 limiting the interjaw force that can be applied. Bipolar cable 440 is connected at its proximal end to the bipolar outputs of a suitable electrosurgical generator, and at its distal end, via wires 442 and 444 to upper jaw 428 and lower jaw 408 respectively such that Radio Frequency (RF) energy from the generator is conducted to jaws 408 and 428 so as to coagulate tissue clamped therebetween. In a preferred embodiment, RF energy from the electrosurgical generator is modulated according to an algorithm in the generator for maximal coagulation of tissue between the jaws while minimizing thermal damage to adjacent tissue.

As best seen in the close-up views of FIGS. 18-20 and 22-23, upper 428 and lower 408 jaws are mirror images, each including a proximal portion that attaches to the distal end of the handpiece and a distal portion that is off-set from the longitudinal axis defined by the handpiece, preferably disposed at an angle of about 45 degrees. The angular offset affords the surgeon better visibility and access to the target surgical site. As best seen in FIG. 19A, upper jaw 428 has a "U" shape with a central slot 429 of width 480, with lower jaw 408 having a corresponding shape so that tissue may be clamped between the U-shaped jaw portions of jaws 408 and 428.

Figure 19A:
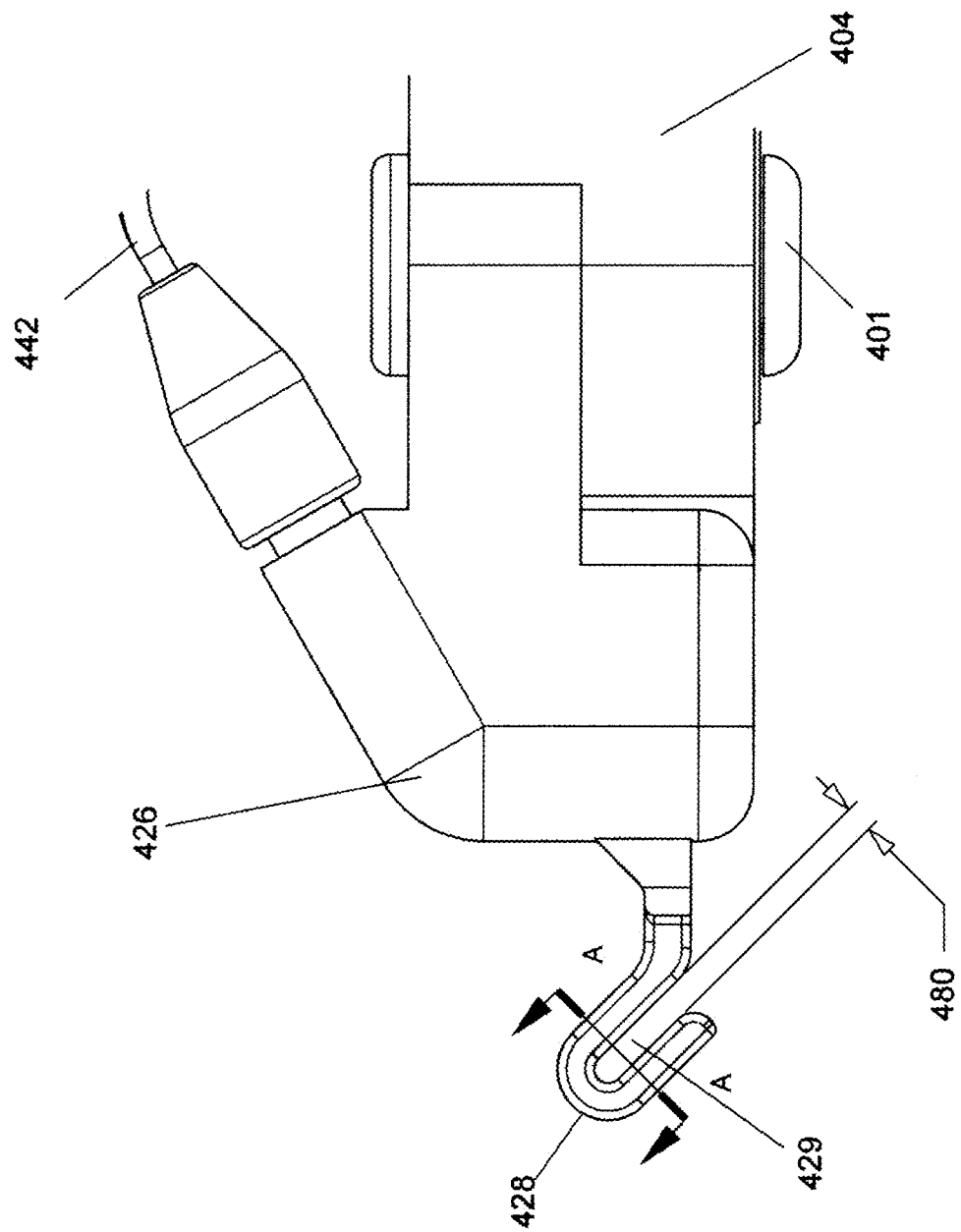
FIG. 19A is an expanded view of the objects of FIG. 16 at location B.
Figure 19B:
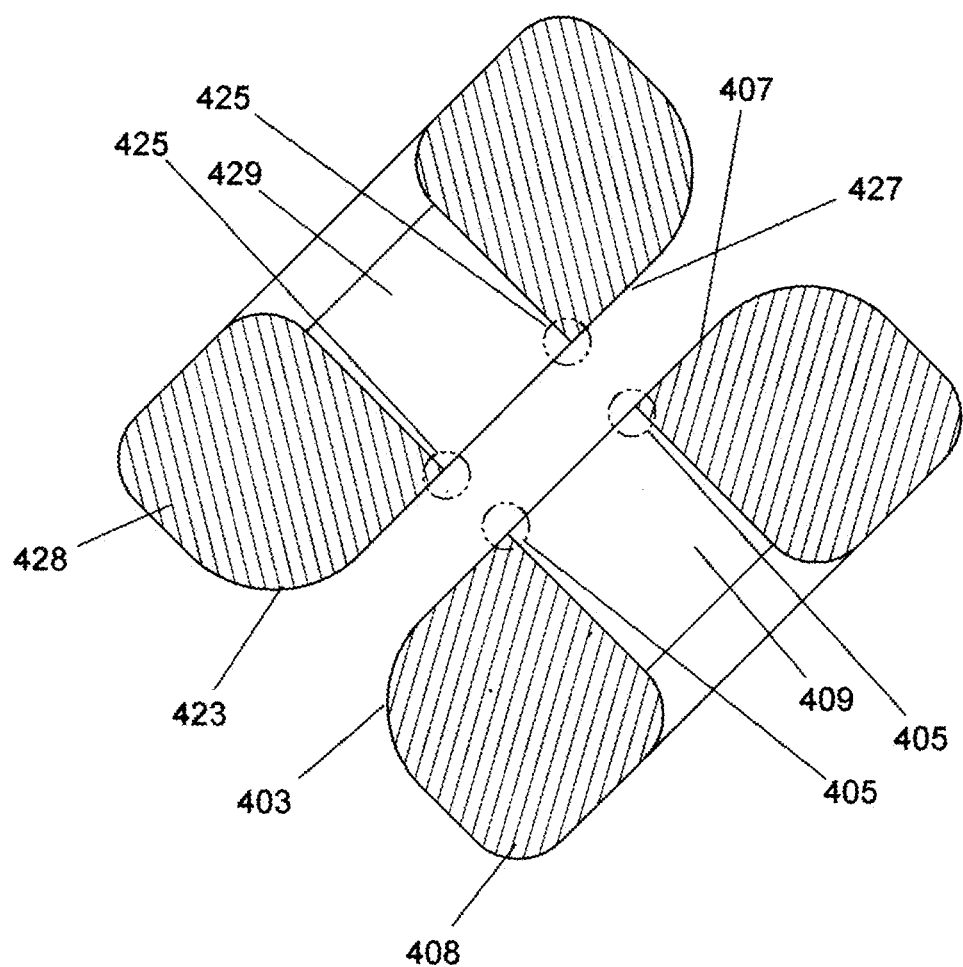
FIG. 19B is an expanded sectional view of the objects of FIG. 19A at location A-A.
Figure 20:
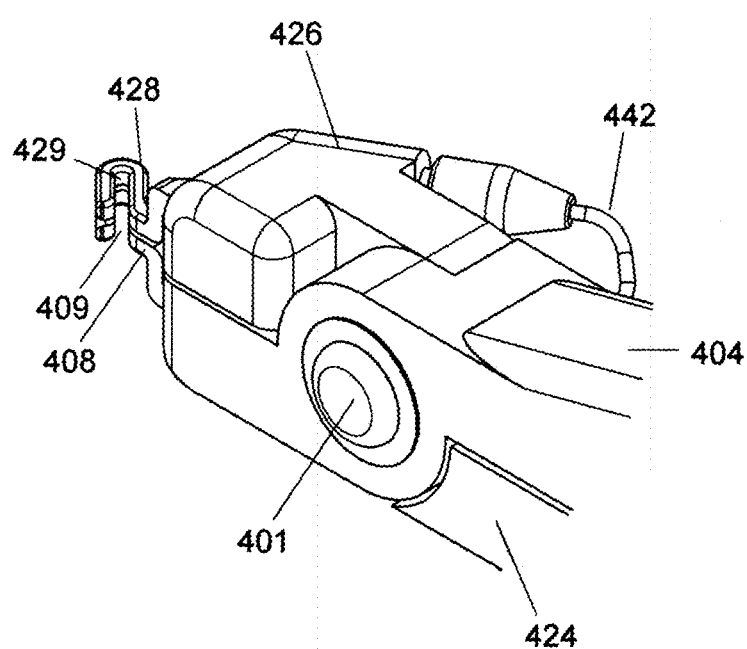
FIG. 20 is an expanded view of the objects of FIG. 18 at location A.
Figure 21:
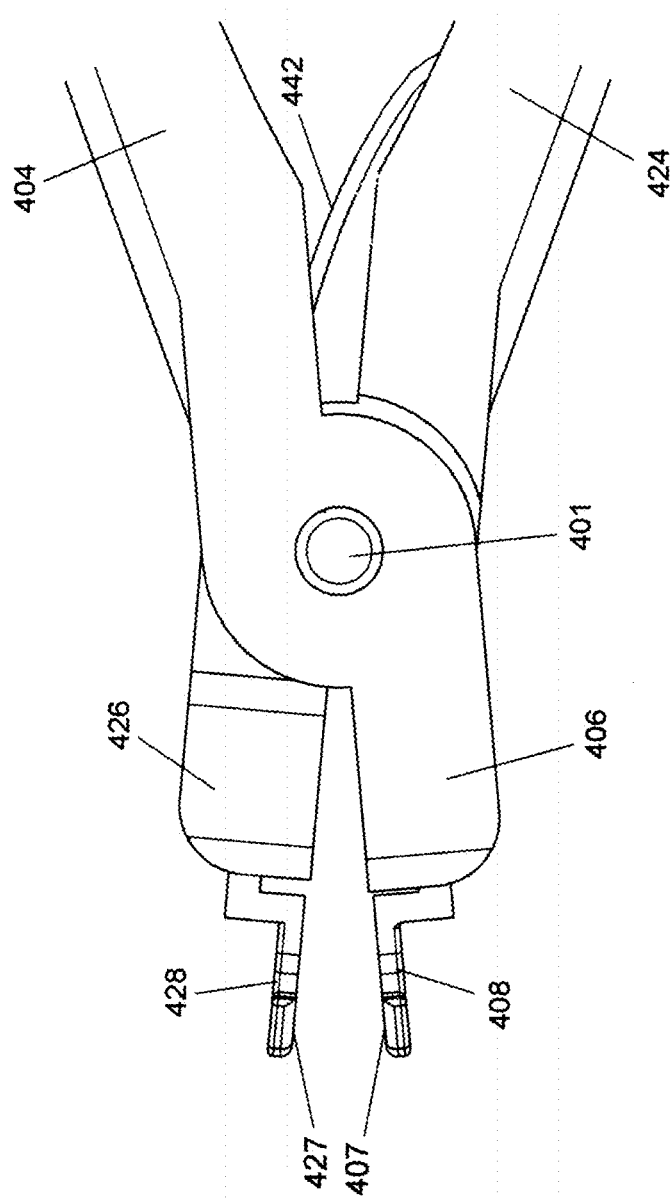
FIG. 21 is an expanded side elevational view of the distal portion of the bipolar electrosurgical device of FIG. 16 with the device in an open, unclamped condition.
Figure 23:
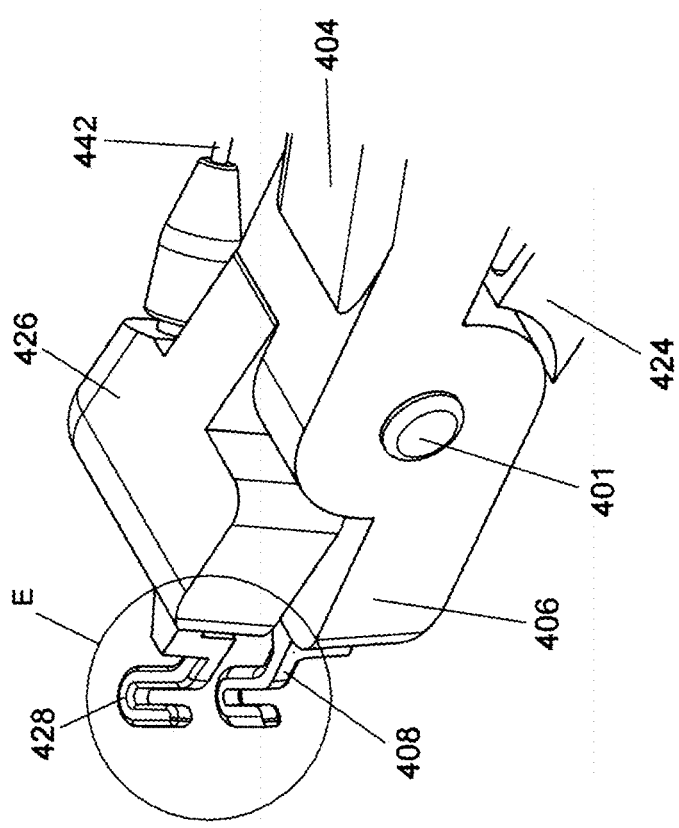
FIG. 23 is a proximal perspective view of the objects of FIG. 21.
Figure 22:
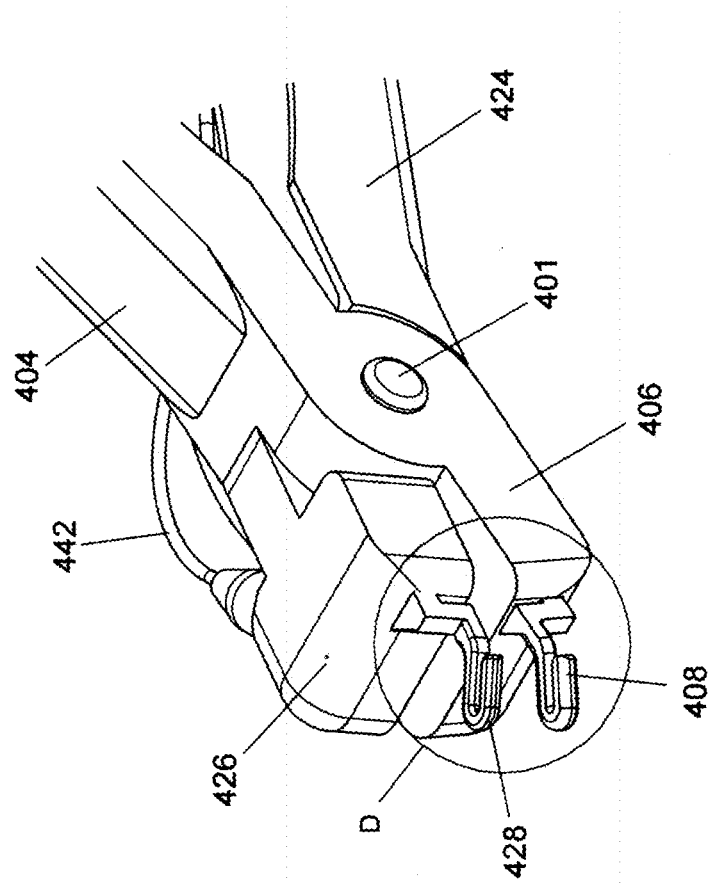
FIG. 22 is a distal perspective view of the objects of FIG. 21.
Figure 25:
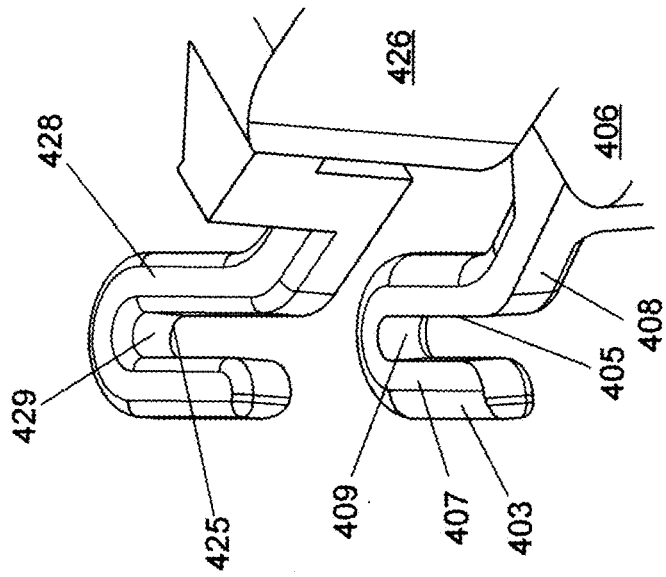
FIG. 25 is an expanded view of the objects of FIG. 23 at location E.
Figure 24:
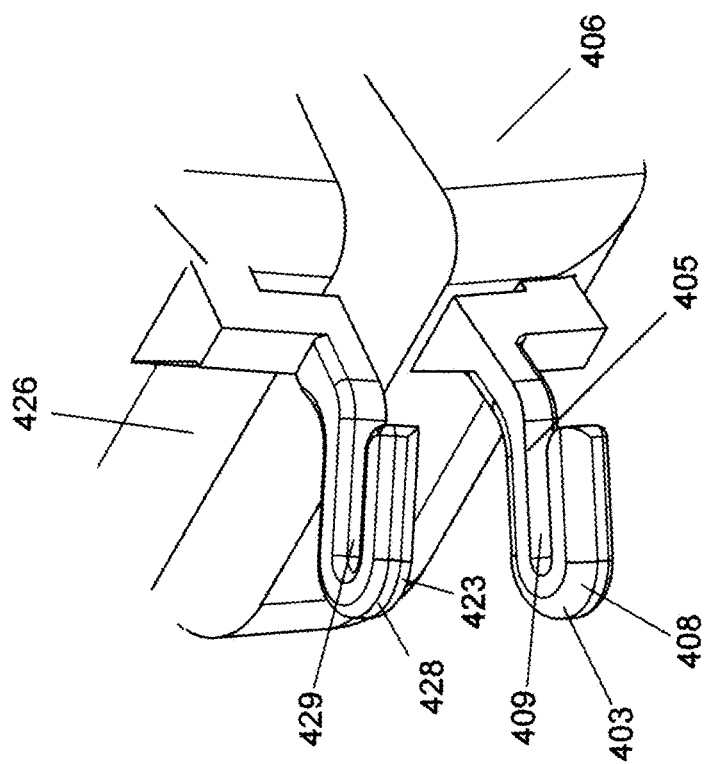
FIG. 24 is an expanded view of the objects of FIG. 22 at location D.

Referring now to FIG. 19B, the U-portions of jaws 408 and 428 have radiused outer circumferential portions 403 and 423 respectively adjacent to their clamping surfaces to prevent cutting of tissue clamped between jaws 408 and 428. Edge 405 formed by the intersection of surface 407 of jaw 408 with the circumferential surface of slot 409 is sharp so as to allow edge 405 to cut tissue. Edge 425 formed by the intersection of surface 427 of jaw 428 with the circumferential surface of slot 429 is also sharp so as to allow edge 425 to cut tissue. Width 480 of slots 409 and 429 is slightly greater than width 116 of distal portions 106 and 126 of excising clamp 100 (see FIG. 15). In a preferred embodiment, each offset central slot defined by each "U-shaped" distal portion is approximately 1-3 mm in width and is further provided with an interior sharp edge, radiused lateral portions, and a relatively planar exterior surface; when brought into contact, in a closed configuration, the respective upper and lower sharp edges together form the cutting surface of the surgical jaws.

The distal portion of handpiece 400 with handpiece 400 in its second (unclamped) position is depicted in FIGS. 21 through 25. Jaws 408 and 428 are formed of a stainless steel or other suitable metallic material.

Figure 26:
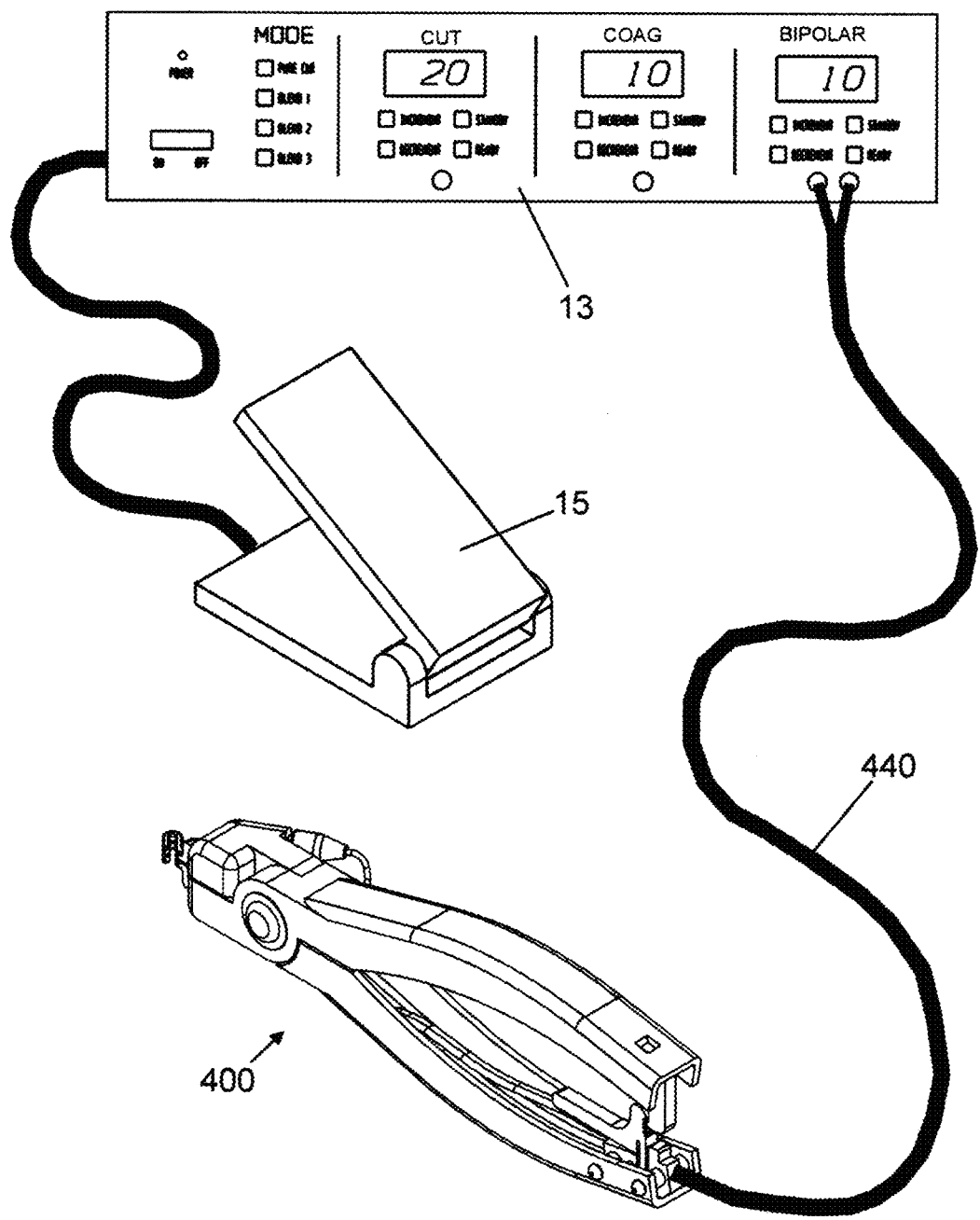
FIG. 26 depicts a surgical system including the bipolar electrosurgical device of FIG. 16 connected to a suitable electrosurgical generator with optional foot pedal connected thereto for activation of the generator.

FIG. 26 depicts bipolar coagulating device 400 connected by cable 440 to the bipolar outputs of electrosurgical generator 13 for use. In the depicted preferred embodiment, generator 13 is activated by foot pedal 15. While not shown, it is understood that electrosurgical generator may be powered by alternating current, for example, via a conventional wall socket, or alternatively may be powered by direct current, for example, by means of an included rechargeable power source.

In a preferred embodiment, generator 13 monitors the impedance of the tissue between jaws 408 and 428 of coagulating device 400 during activation, the impedance increasing as coagulation of the tissue proceeds. When the impedance reaches a preset value indicating that a predetermined level of coagulation has been reached, generator 13 is automatically deactivated or, alternatively, an audible signal is given to indicate to the surgeon that coagulation is complete so that the surgeon may terminate activation. In other embodiments, the surgeon determines when coagulation is complete and physically deactivates the generator by releasing foot pedal 15. In some preferred embodiments, generator 13 has an algorithm that modulates the power output of generator 13 to achieve effective coagulation without charring the tissue. In other embodiments, the power output of generator 13 is determined by the surgeon. In still other embodiments the generator measures the initial impedance of tissue clamped between jaws 408 and 428. If the impedance falls within a predetermined acceptable range, the generator may automatically activate after a predetermined time delay and terminate activation when a predetermined impedance value is reached. In these embodiments foot pedal 15 is eliminated.

Excising clamp 100 and coagulating device 400 work together to occlude a generally tubular tissue structure by means of coagulation and to subsequently excise a portion of the tissue structure. In use, an elongate tissue structure is captured by clamp 100, locally coagulated by coagulating device 400, and thereafter a portion of the tissue is excised by clamp 100. A preferred method of cooperative use of excising clamp 100 and bipolar coagulating device 400 is hereafter described.

Figure 14A:
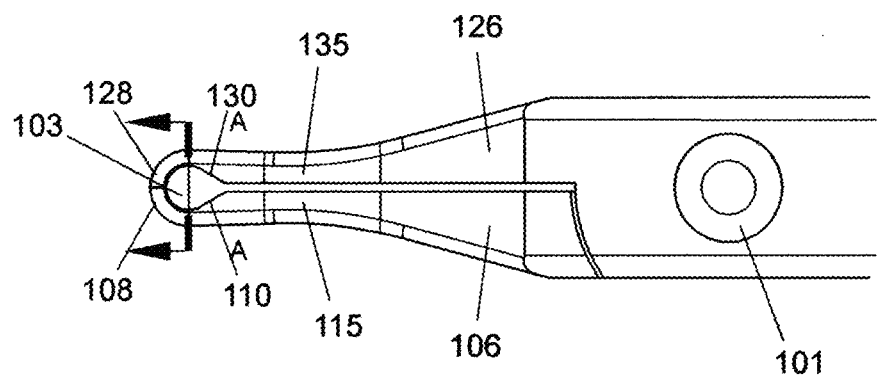
FIG. 14A is an expanded view of the clamp of FIG. 12 at location B.
Figure 14B:
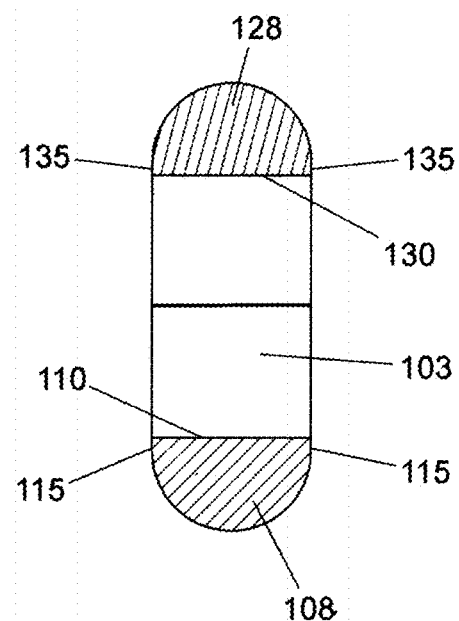
FIG. 14B is an expanded sectional view of the objects of FIG. 14A at location A-A.
Figure 15:
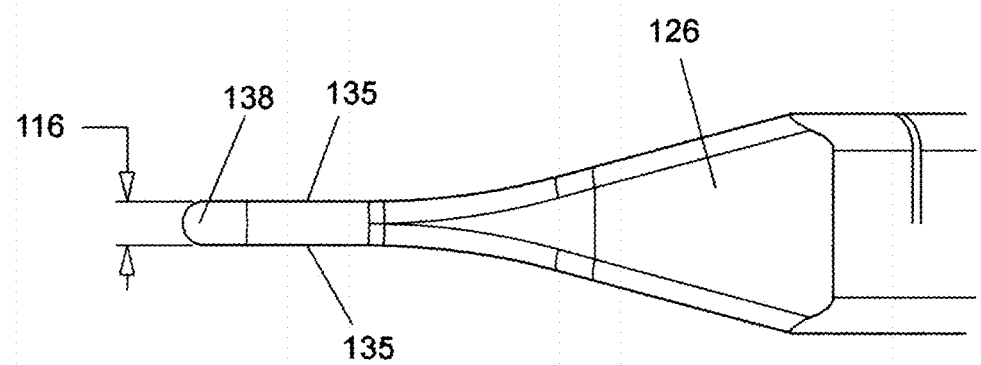
FIG. 15 is an expanded plan view of the distal portion of the clamp of FIG. 11.
Figure 18:
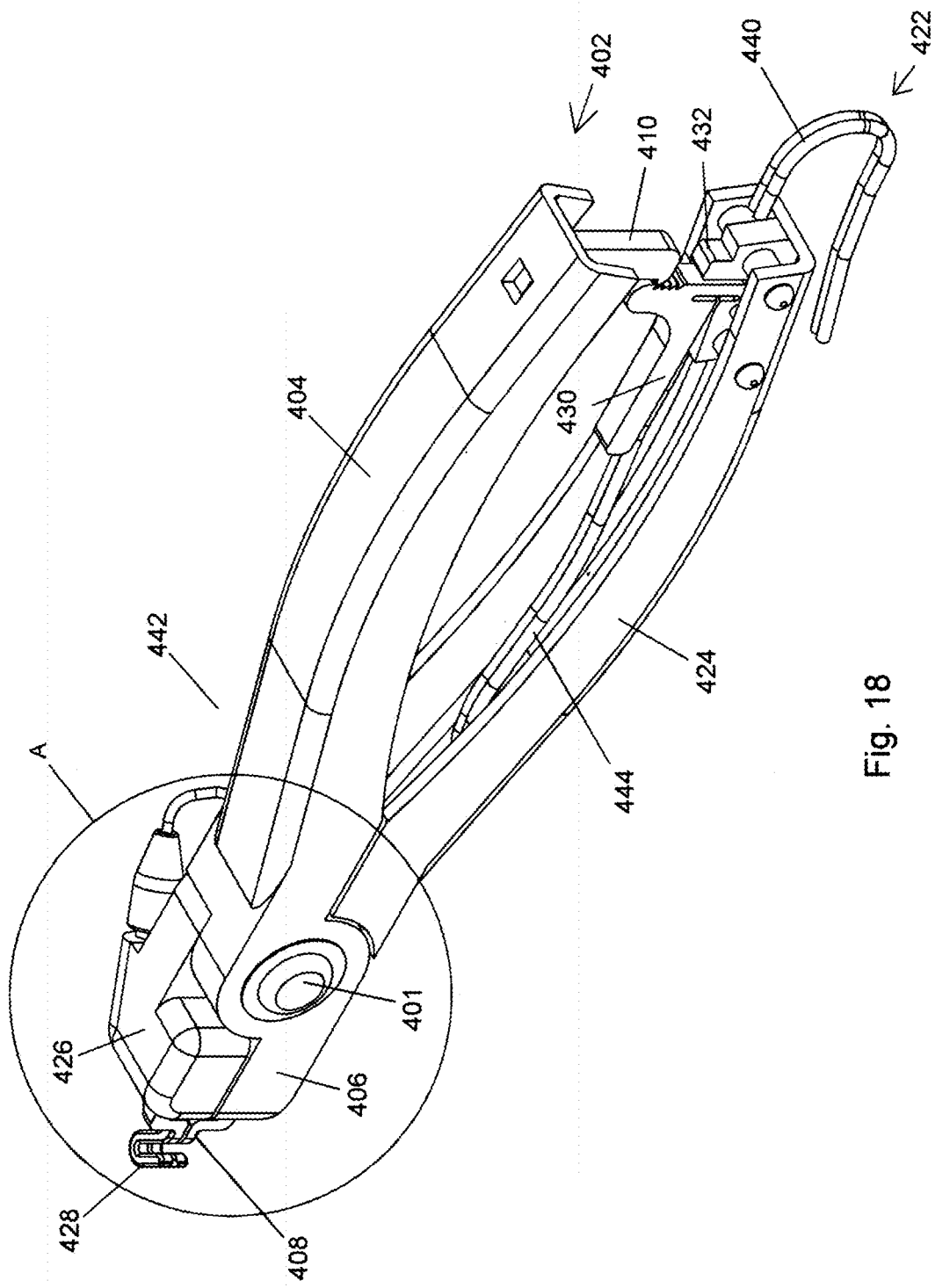
FIG. 18 is a perspective view of the objects of FIG. 16.
Figure 27A:
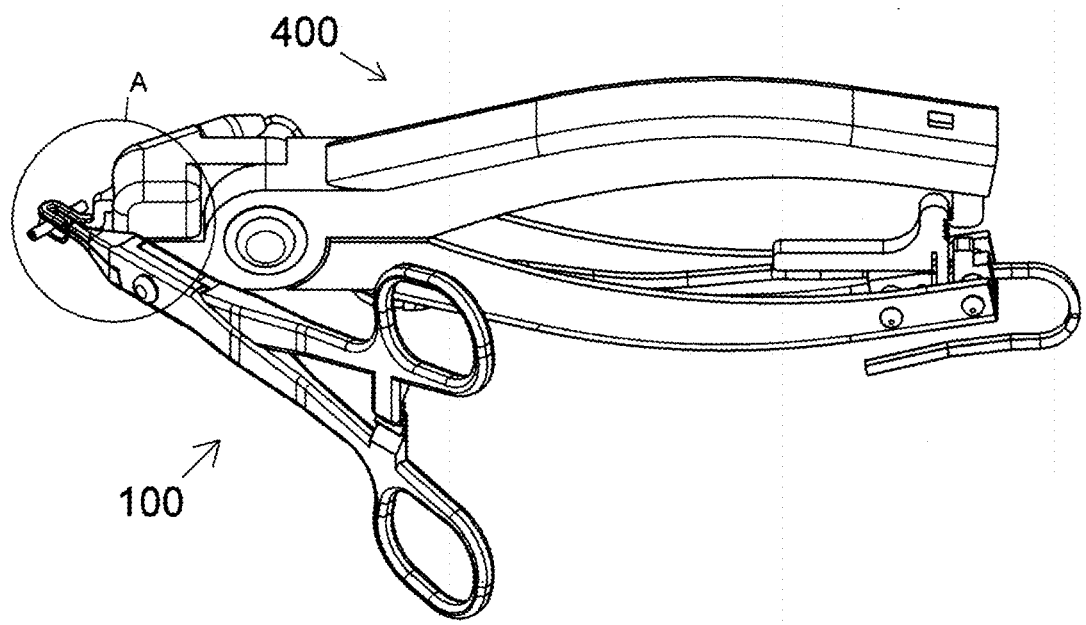
FIG. 27A is a perspective diagrammatic view of an elongate tissue element captured within the excising clamp of FIG. 11, and clamped between the jaws of the bipolar electrosurgical device of FIG. 16 as during use.
Figure 27B:
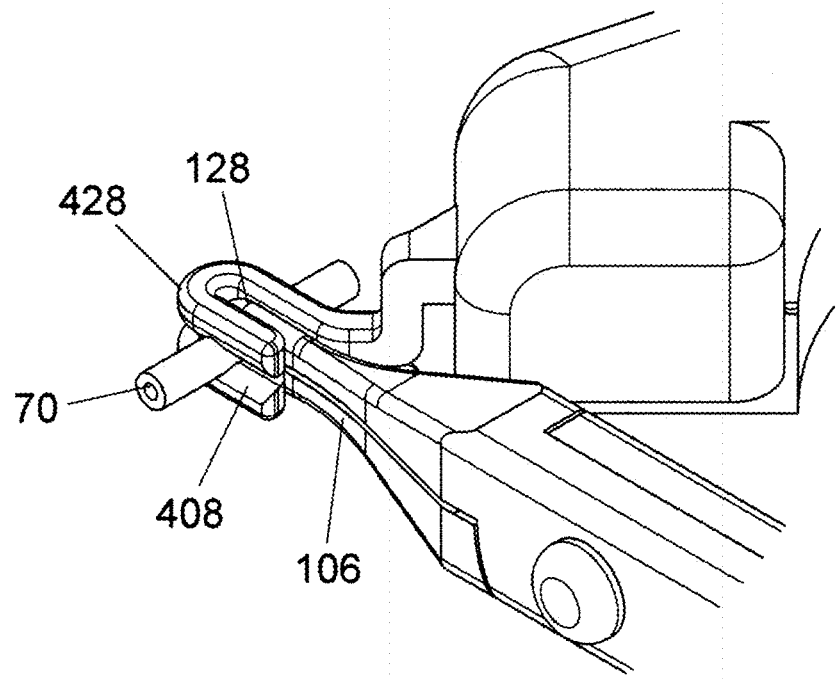
FIG. 27B is an expanded view of the objects of FIG. 27A at location A.
Figure 27C:
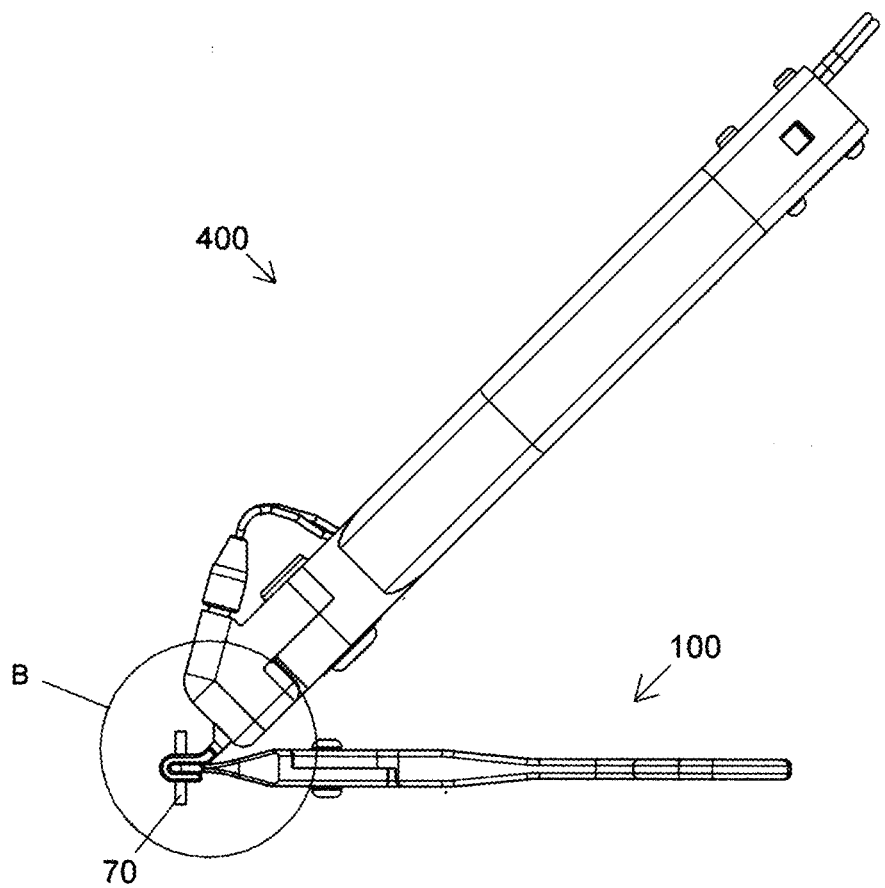
FIG. 27C is a plan view of the objects of FIG. 27A.
Figure 27D:
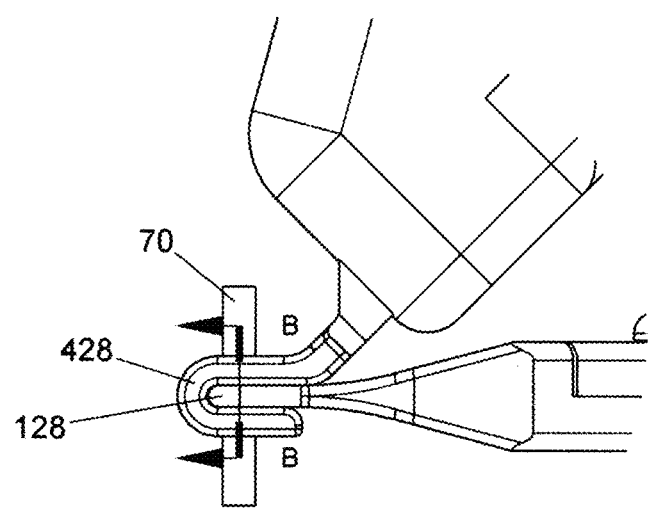
FIG. 27D is an expanded view of the objects of FIG. 27C at location B.
Figure 27E:
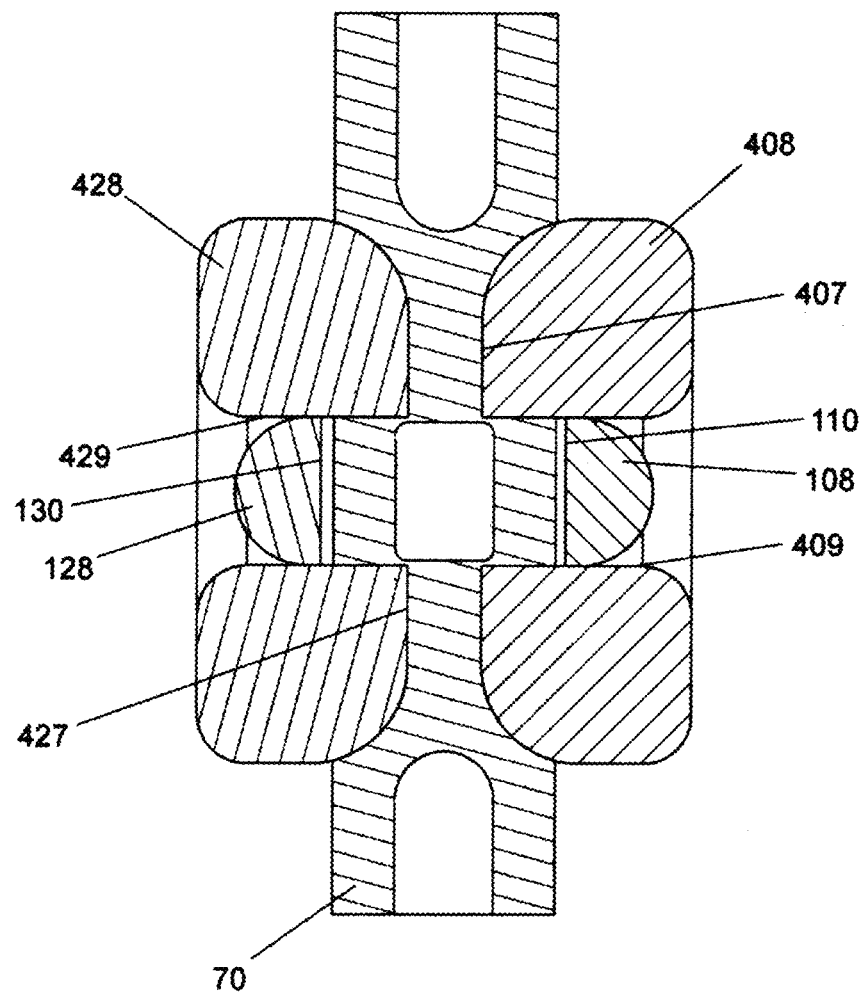
FIG. 27E is an expanded sectional view of the objects of FIG. 27D at location B-B.
Figure 27F:
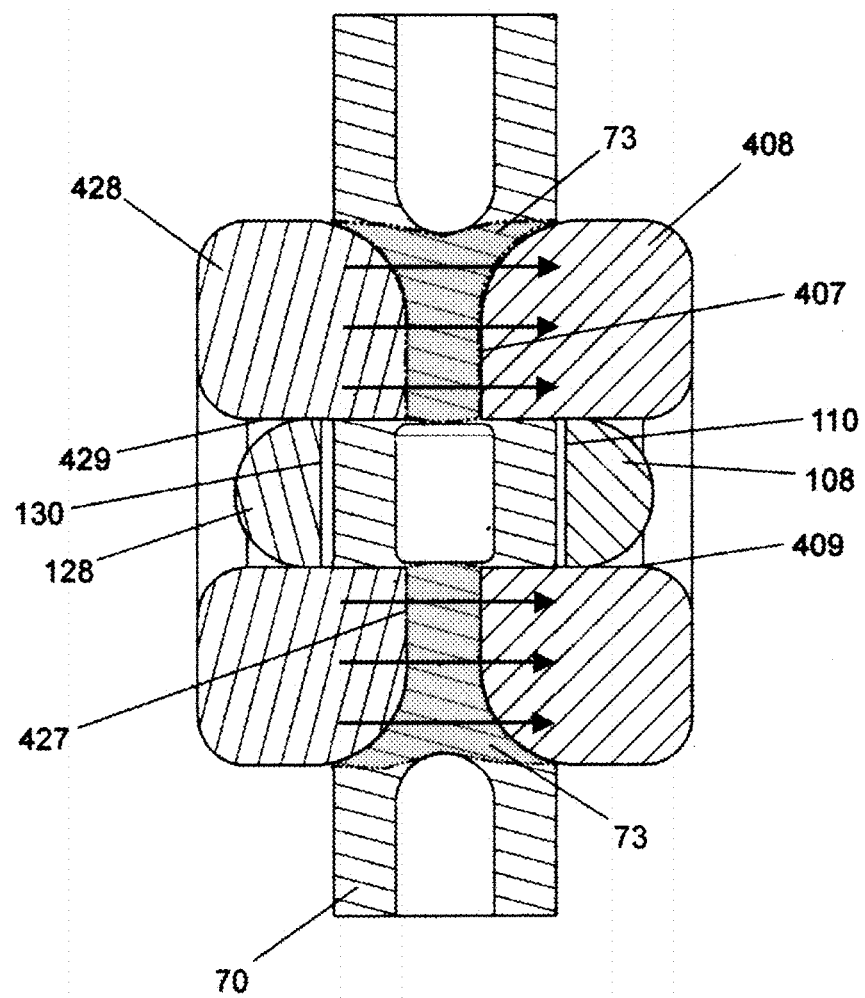
FIG. 27F depicts the objects of FIG. 27E, wherein RF energy is applied so as to coagulate tissue between the jaws of the electrosurgical device.
Figure 27G:
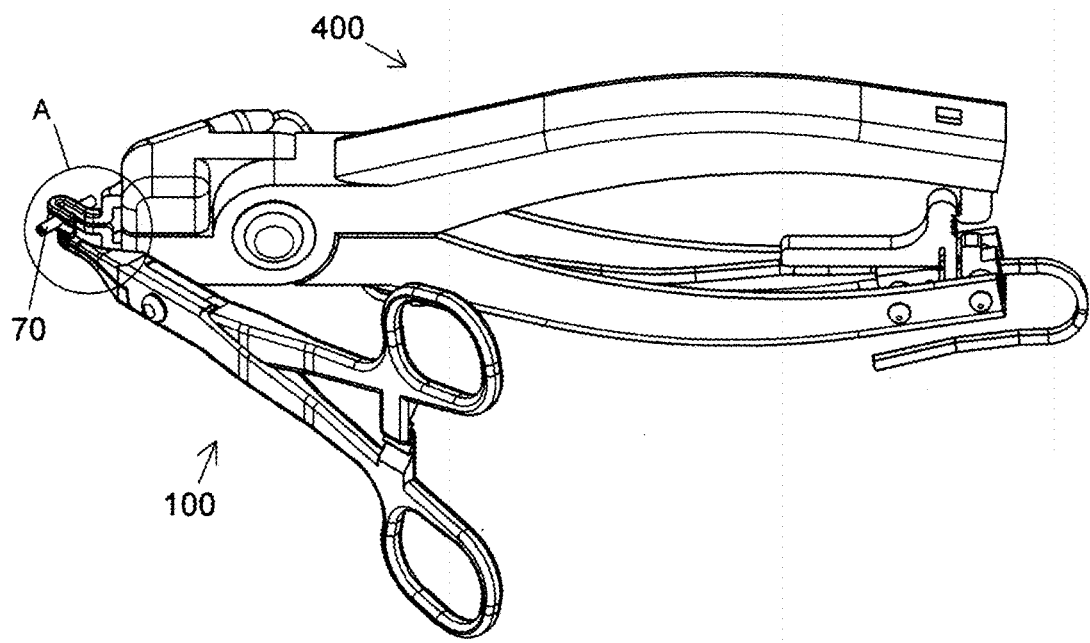
FIG. 27G is a perspective view of the objects of FIG. 27F, wherein the excising clamp has been moved downward so as to remove a portion of the elongate tissue element.
Figure 27H:
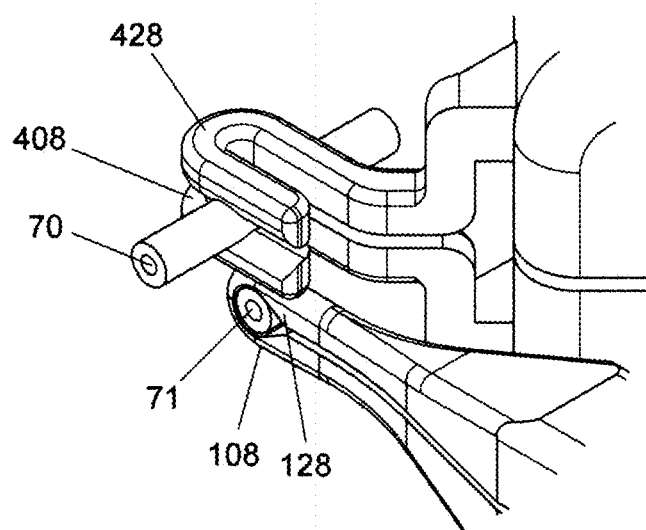
FIG. 27H is an expanded view of the objects of FIG. 27G at location A.
Figure 27I:
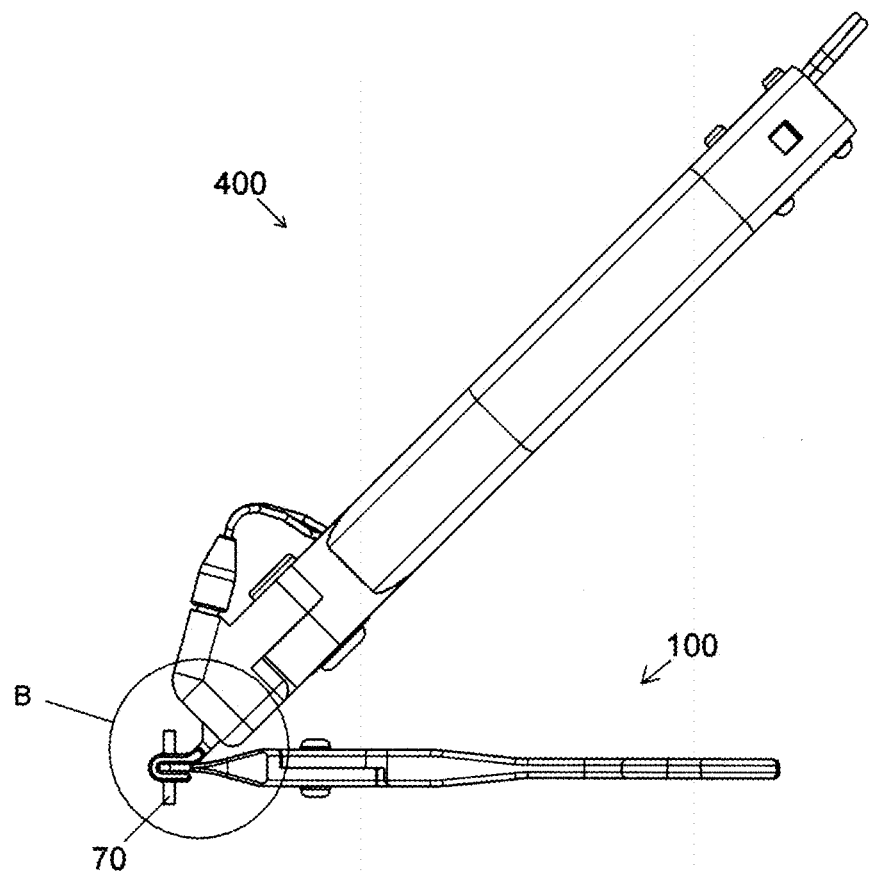
FIG. 27I is a plan view of the objects of FIG. 27G
Figure 27J:
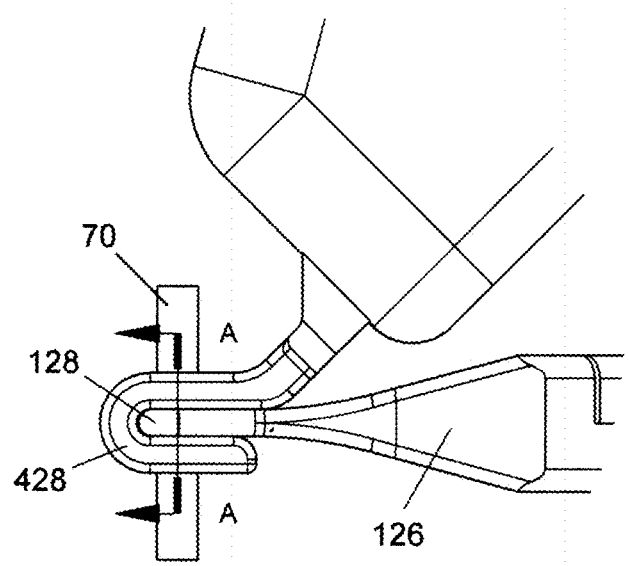
FIG. 27J is an expanded view of the objects of FIG. 27I at location B.

FIGS. 27A through 27E depict an elongate tissue element 70 captured within eyelet 103 of jaws 108 and 128 of clamp 100 (see FIG. 14A). As best seen in FIG. 27E, jaws 108 and 128 with tissue element 70 captured therein are positioned within slots 409 and 429 of jaws 408 and 428 respectively of bipolar coagulating device 400, with jaws 408 and 428 clamped on tissue element 70 lateral to jaws 108 and 128 of clamp 100. In FIG. 27F, generator 13 has been activated causing radio frequency energy indicated by arrows to flow between jaws 408 and 428 of bipolar coagulating device 400. This energy flow and pressure applied by jaws 408 and 428 causes coagulation of portions 73 of elongate tissue element 70 clamped between jaws 408 and 428 of coagulating device 400. When RF energy is applied, the collagen and elastin in the tissues are reformed by heat and pressure to fuse the walls of the tubular tissue element 70, thereby forming a permanent seal.

Figure 27K:
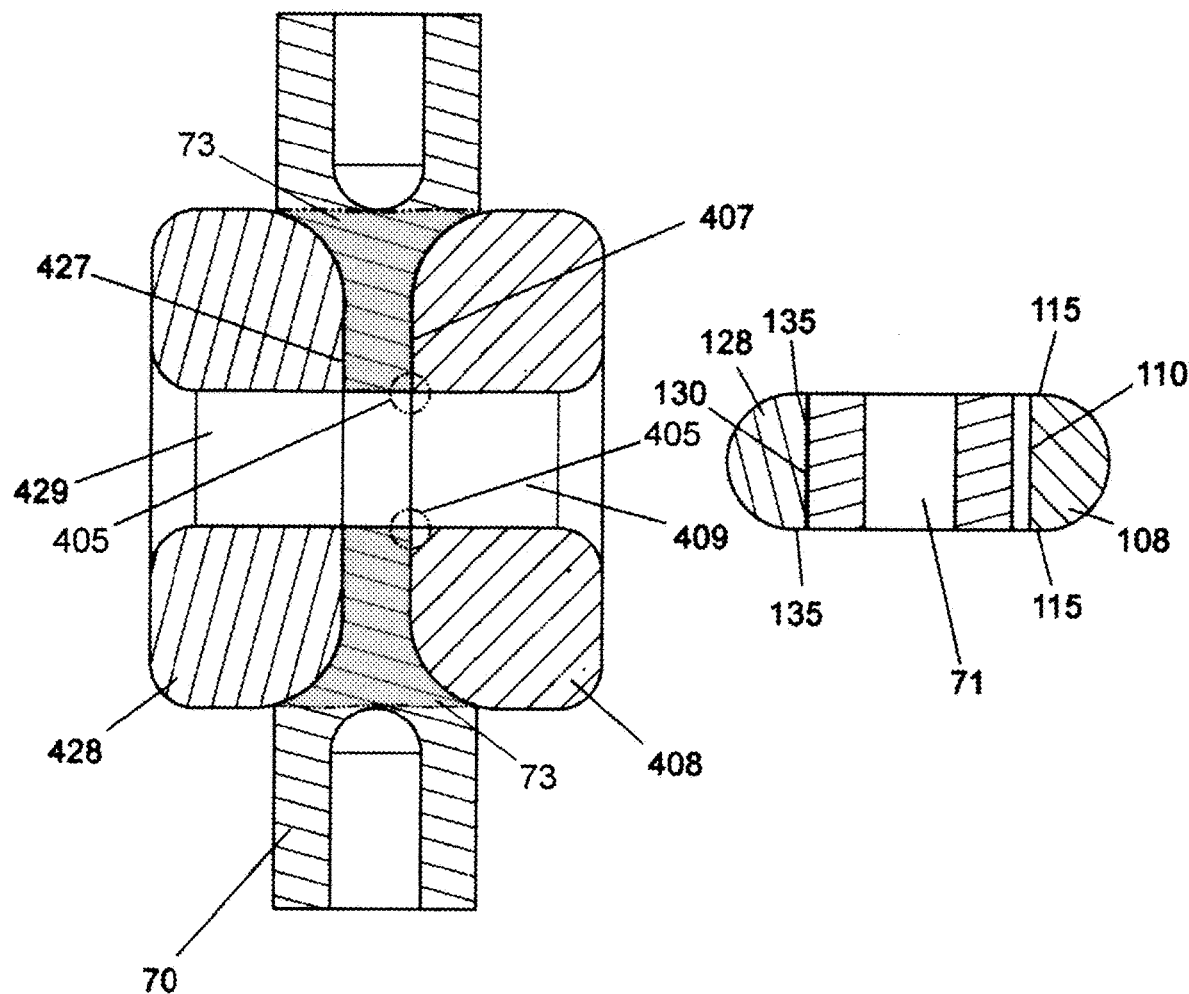
FIG. 27K is an expanded sectional view of the objects of FIG. 27J at location A-A.

In FIGS. 27G through 27K, clamp 100 has been displaced downward relative to jaws 408 and 428 of coagulating device 400 so as to excise portion 71 of tissue element 70. Referring to FIG. 27K, the intersections of surface 130 with lateral surfaces 135 form cutting edges on excising clamp 100 at eyelet 103. Similarly, the intersection of surface 407 with the surface of slot 409 of jaw 408 forms cutting edge 405 that surrounds slot 409 of coagulating device 400. Portion 71 is excised from elongate tissue element 70 by the cooperative cutting action of the previously described cutting edges of clamp 100 and coagulating device 400. Jaw 428 of coagulating device 400 and jaw 108 of clamp 100 each have cutting edges symmetrically opposed to those of the opposing jaw on their particular device so that excision of portion 71 may alternatively be accomplished by upward relative movement of clamp 100 relative to coagulating device 400. Because the cutting edges formed on jaws 408 and 428 of coagulating device 400 are planar, and edges of jaws 108 and 128 of excising clamp 100 have a curvilinear profile, a shearing action occurs as a cutting edge of clamp 100 passes by a cutting edge of coagulating device 400. Portion 71 of elongate tissue element 70 is not coagulated.

Figure 27L:
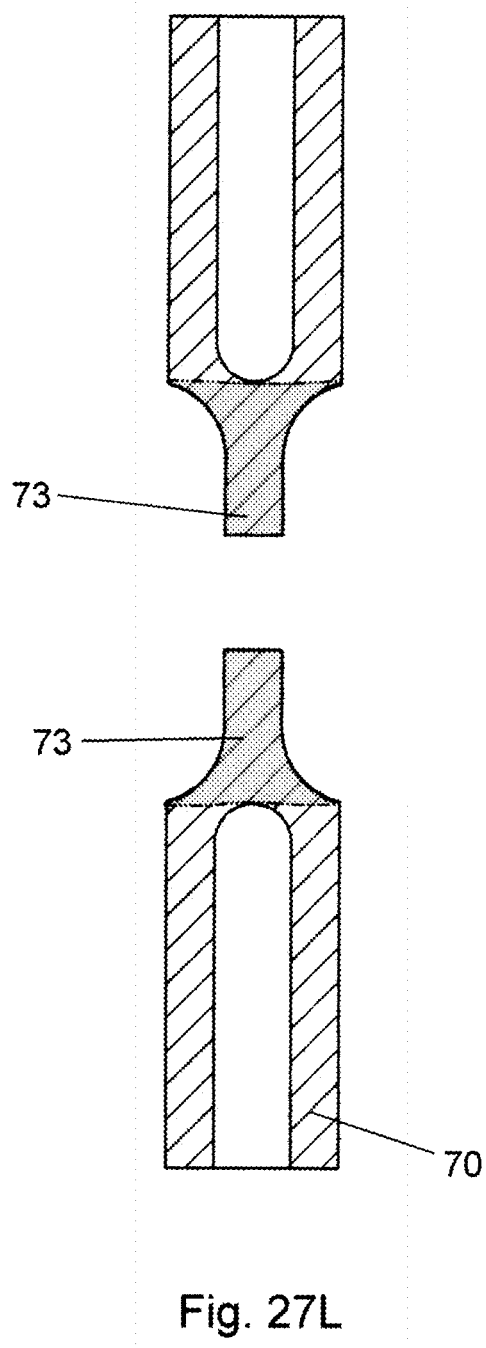
FIG. 27L is a sectional view of the elongate tissue element after coagulation and excision as previously described.
Figure 27M:
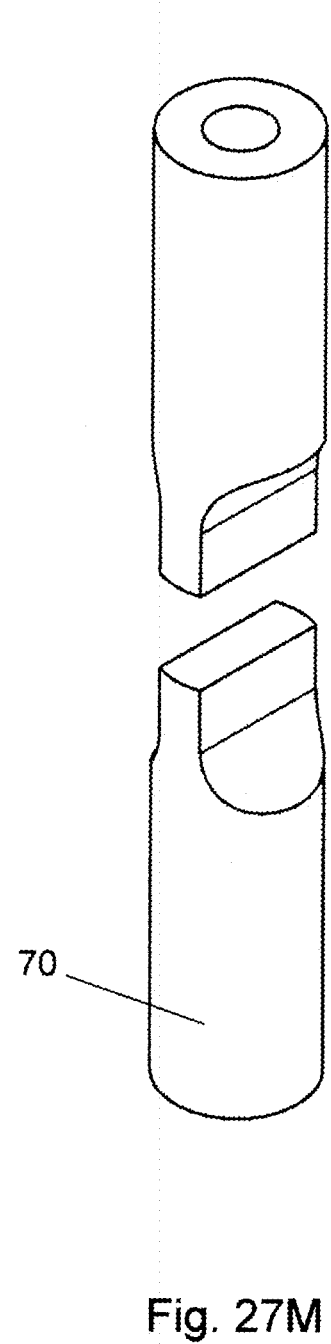
FIG. 27M is a perspective view of the elongate tissue element of FIG. 27L.

FIGS. 27L and 27M depict elongate tissue element 70 at the completion of the procedure previously described. Element 70 has been divided and the ends created sealed by coagulation. Coagulated regions 73 occlude the lumen, and dividing tubular element 70 by excision of portion 71 permanently prevents flow through tubular element 70.

Bipolar tissue sealing and cutting devices are well known in the art. Typical of these is the LigaSure™ Vessel Sealing System by Covidien, Inc (Boulder, CO). Therein, a pair of bipolar jaws is used to coagulate tissue clamped between them. When coagulation is complete, a cutting element is distally extended in a groove formed in the jaws to divide the vessel through the middle of the coagulated region. The sealing and excision method and devices of the present invention differ from those of prior art vessel sealing and cutting systems in that a tissue portion is excised to divide the structure, the excised portion being made up of uncoagulated tissue. Also, excision of the uncoagulated tissue portion is accomplished by a second device, one that is particularly adapted to receive, isolate and excise a tubular tissue as opposed to by the coagulating device per se.

In the novel methods of the present invention, an excising clamp of the present invention excises an uncoagulated tissue portion through a cooperative cutting action between cutting edges formed on the excising clamp and the jaws of the bipolar coagulating device. In further contrast to prior art seal and cut devices, which tend to be poorly suited for vasectomy applications, the novel methods of the present invention enable delivery of the vas duct from the scrotum so that coagulation and separation of the duct can be directly observed and avoid the unnecessarily complex and inconvenient manipulation and exchanging of devices by the surgeon.

Figure 28B:
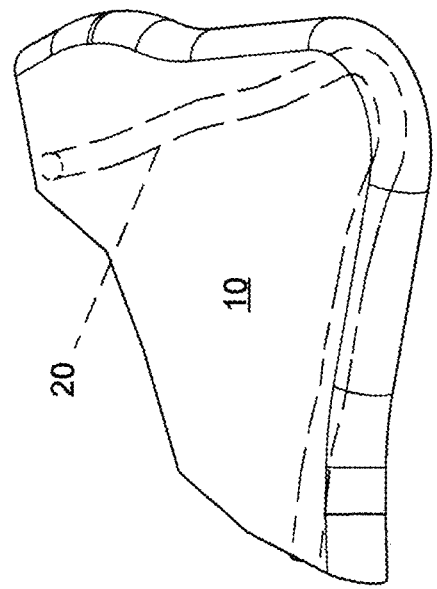
FIG. 28B is a perspective view of the objects of FIG. 28A.
Figure 28A:
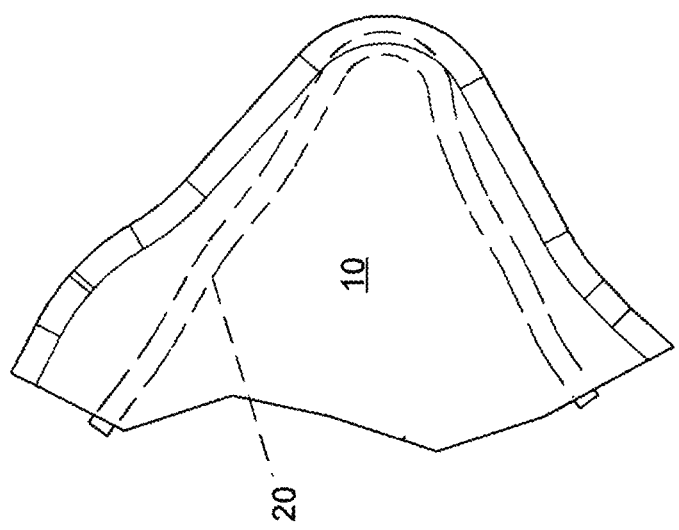
FIG. 28A is a diagrammatic plan view of a portion of a scrotum with a vas deferens contained therein.
Figure 29A:
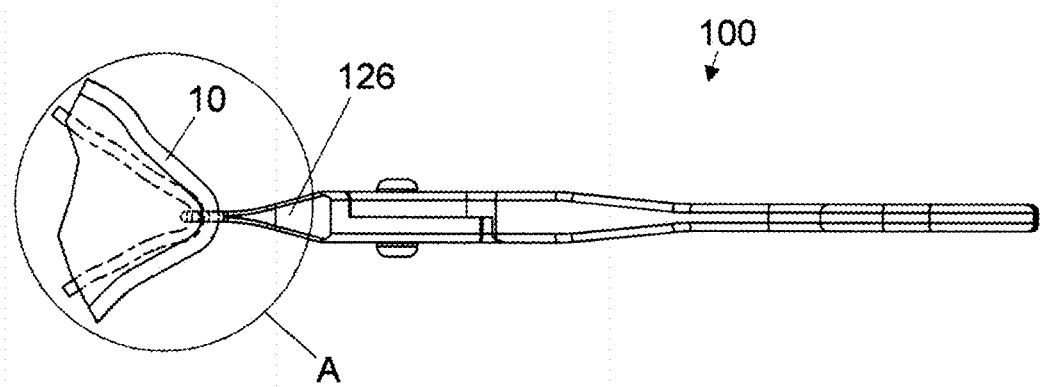
FIG. 29A is a plan view of an excising clamp of the present invention capturing the vas deferens of FIG. 27 inside the scrotum of FIG. 27.
Figure 29B:
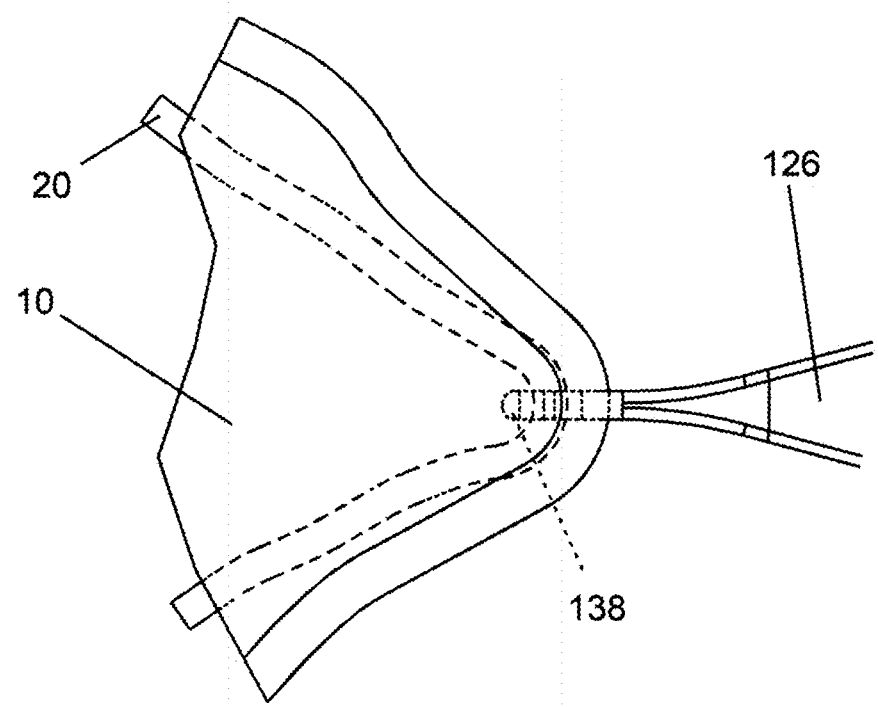
FIG. 29B is an expanded view of the objects of FIG. 29A at location A.
Figure 30A:
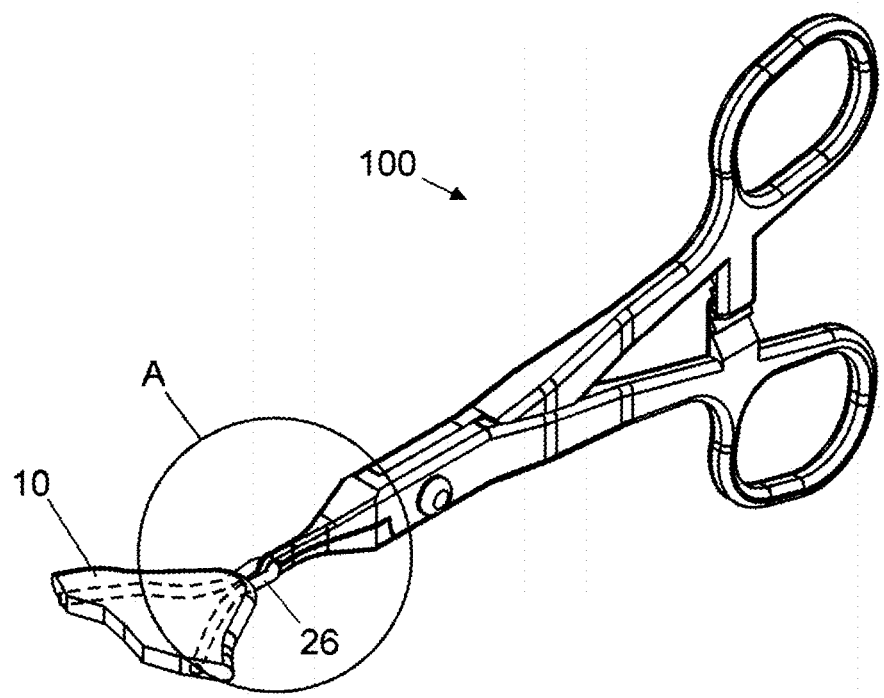
FIG. 30A depicts the objects of FIG. 29A with the vas duct delivered from the scrotum.
Figure 30B:
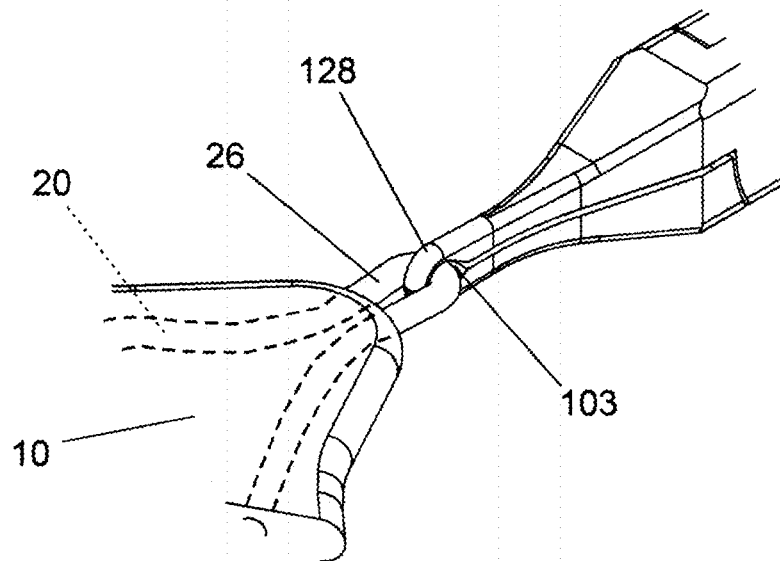
FIG. 30B is an expanded view of the objects of FIG. 30A at location A.
Figure 31A:
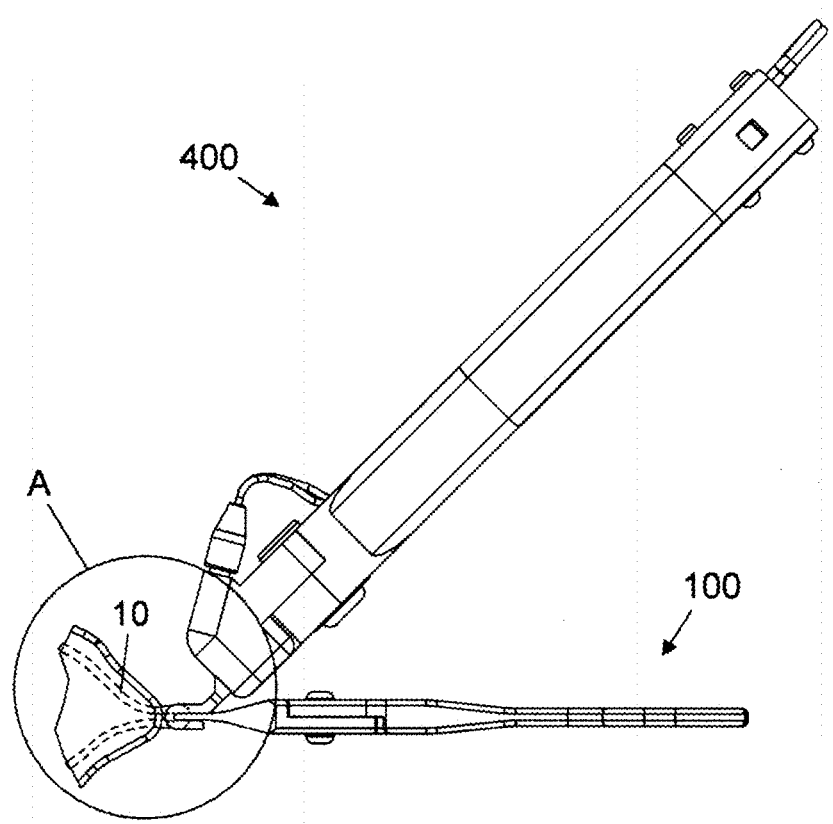
FIG. 31A depicts the objects of FIG. 30A with the captured vas duct clamped between the jaws of the bipolar coagulating device of the vasectomy system of the present invention.
Figure 31B:
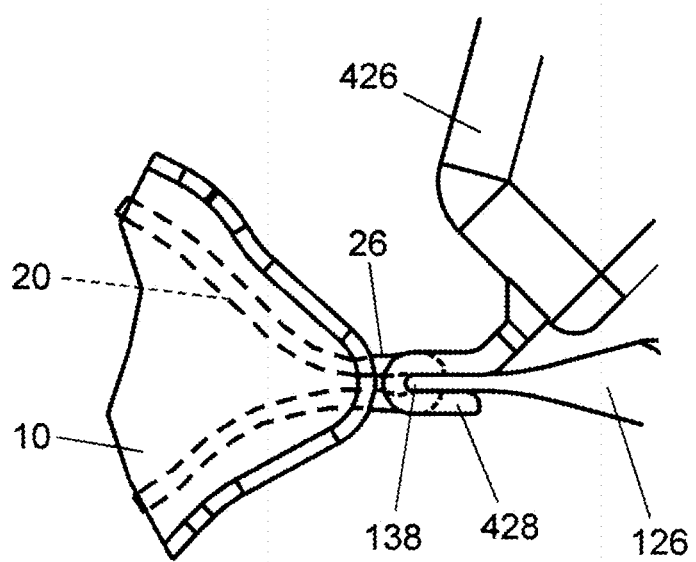
FIG. 31B is an expanded view of the objects of FIG. 31A at location A.
Figure 32A:
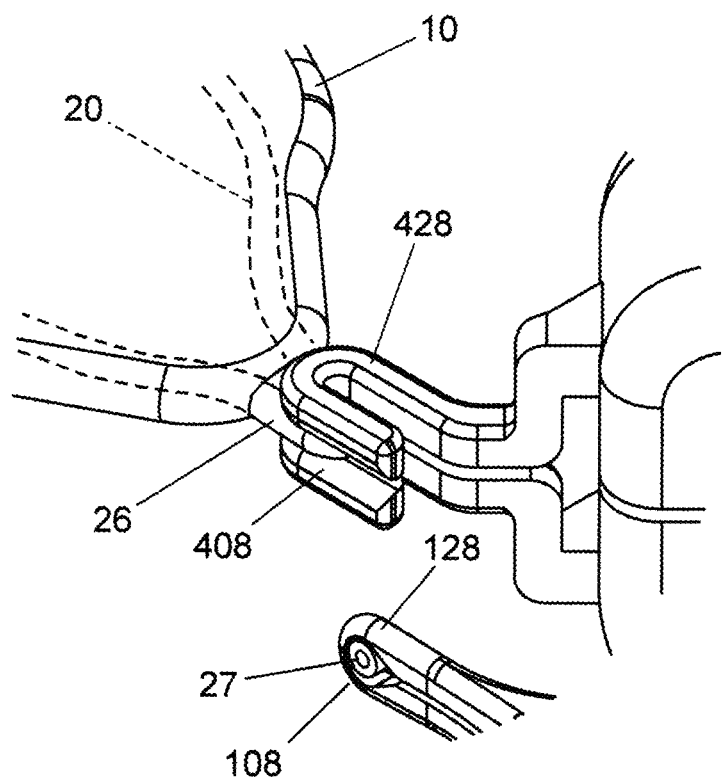
FIG. 32A is a perspective view of the coagulated vas duct clamped between the jaws of the bipolar device with an uncoagulated portion of the duct removed by the excising clamp.
Figure 32B:
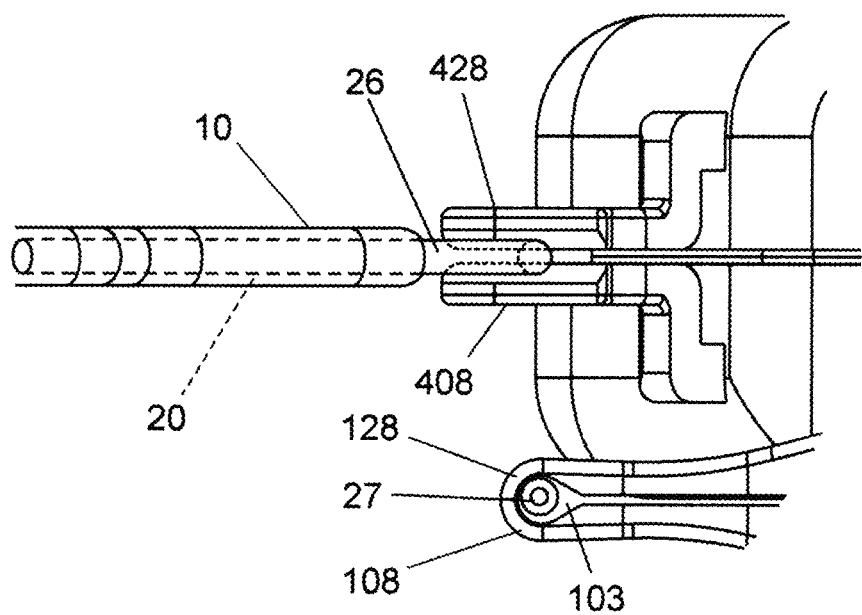
FIG. 32B is a side elevational view of the objects of FIG. 32A.
Figure 33A:
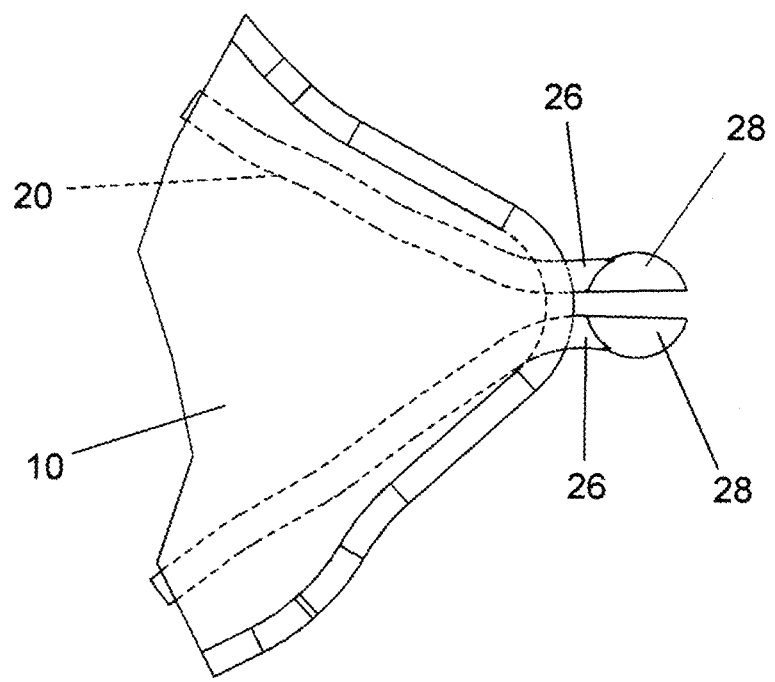
FIG. 33A is a plan view of the scrotum and coagulated vas duct after removal of the bipolar coagulating device.
Figure 33B:
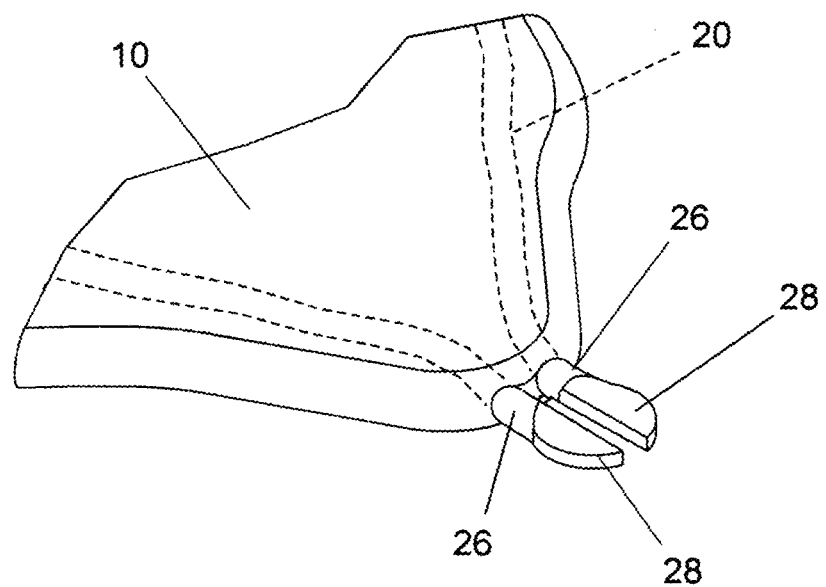
FIG. 33B is a perspective view of the objects of FIG. 33A.
Figure 34:
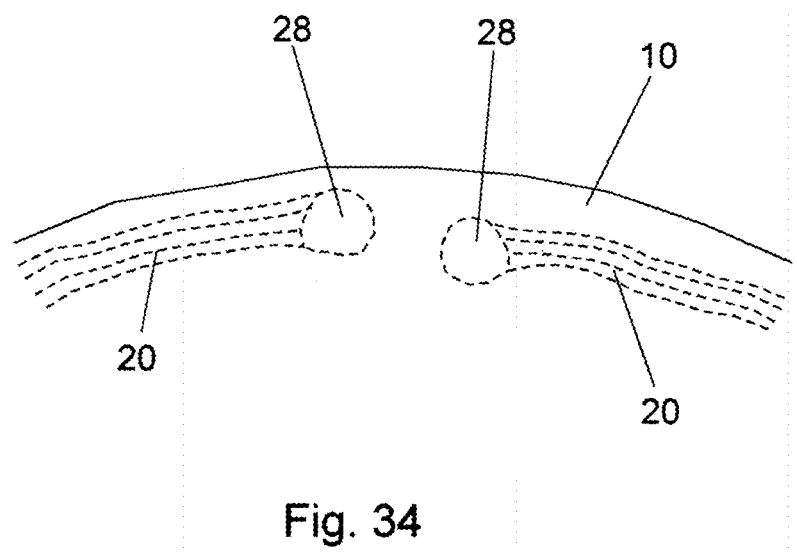
FIG. 34 depicts the site after the vas duct is returned to the scrotum.
Figure 35:
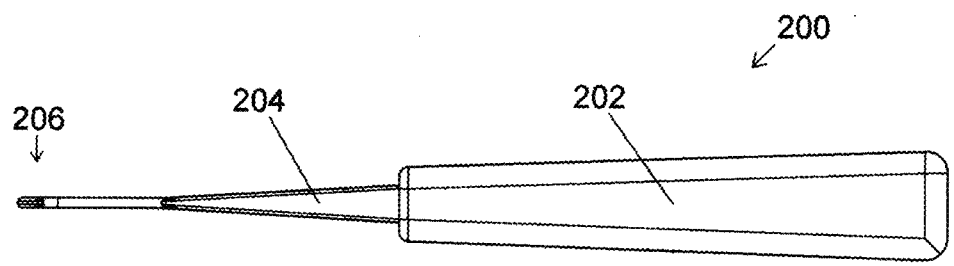
FIG. 35 is a plan view of an excising hook of the present invention.
Figure 36:
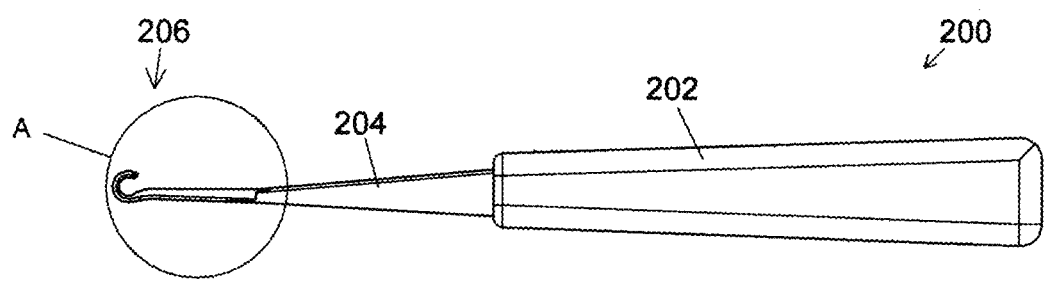
FIG. 36 is a side elevational view of the objects of FIG. 35.
Figure 37:
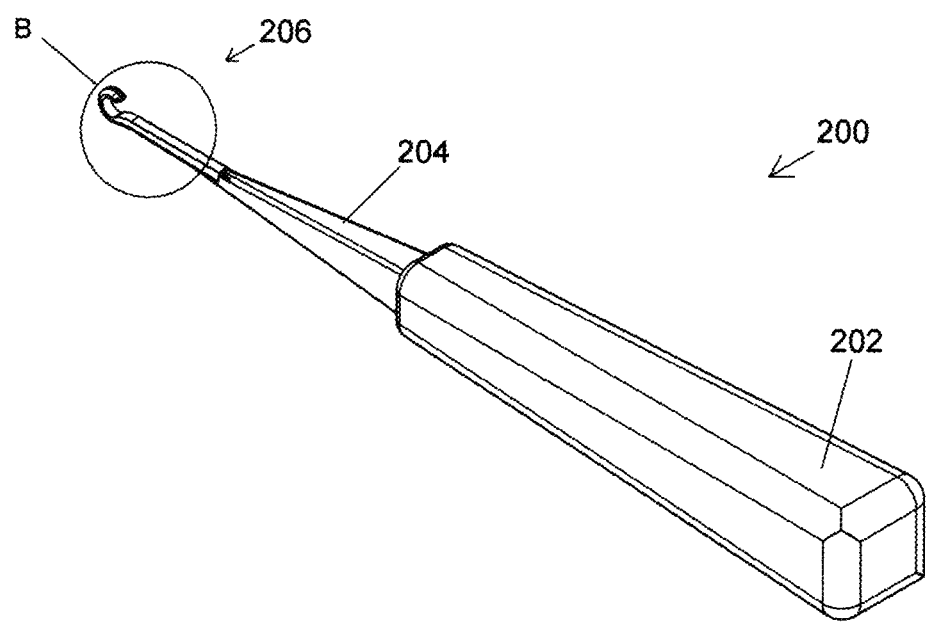
FIG. 37 is a perspective view of the objects of FIG. 35.
Figure 38:
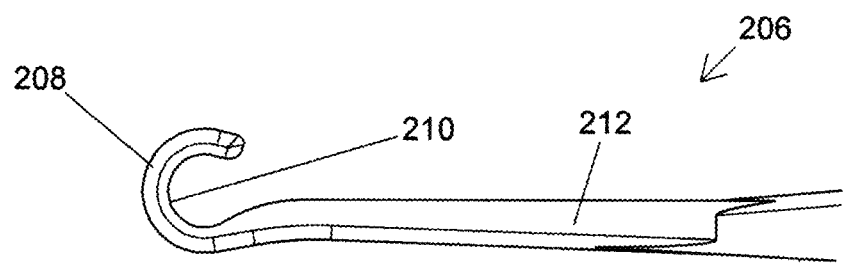
FIG. 38 is an expanded view of the objects of FIG. 36 at location A.
Figure 39:
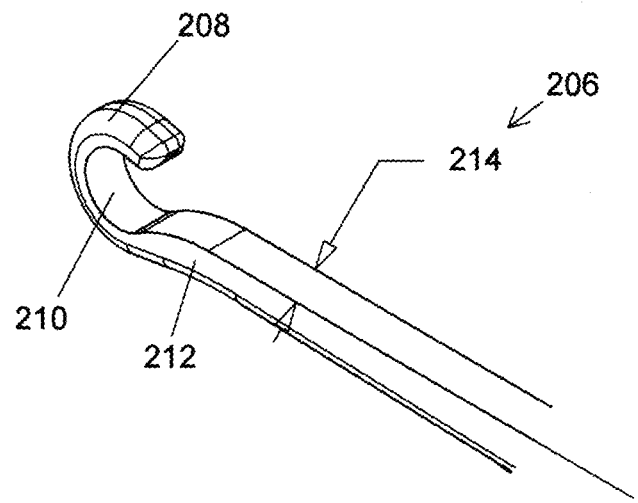
FIG. 39 is an expanded view of the objects of FIG. 37 at location B.

Use of devices and methods of the present invention for occluding and dividing by excision a tubular tissue element are hereinafter described as they relate to performing a vasectomy. FIGS. 28A and 28B diagrammatically depict a vas duct 20 positioned within a fold of scrotum 10. Vas duct 20 is located in scrotum 10 using the standard "three-finger" technique used for no scalpel vasectomy (NSV) procedures. Thereafter, a local anesthetic is introduced and an opening formed in scrotum 10 using a dissecting forceps, both in the same manner as for a standard NSV. Then, as depicted in FIGS. 29A and 29B, distal portion of clamp 100 is inserted into scrotum 10 so as to capture duct 20 in eyelet 103 formed by jaws 108 and 128 of clamp 100 (see FIG. 14A). In FIGS. 30A through 31B, excising clamp 100 has delivered vas 20 from scrotum 10 with portion 26 of duct 20 retained within eyelet 103 of clamp 100 in the manner previously described using tubular tissue element 70. The clinician may, optionally, grasp the vas after forming the opening in the scrotum with the dissecting forceps or another device to position the vas for capture by clamp 100. Thereafter, jaws 408 and 428 are positioned about jaws 108 and 128 of clamp 100 as depicted in FIGS. 31A and 31B, portion 26 of duct 20 being clamped between jaws 408 and 428 as previously described and shown in FIGS. 27A through 27E using tubular tissue element 70. Radio Frequency energy is then supplied by electrosurgical generator 130 via cable 440 to jaws 408 and 428 so as to coagulate portions of portion 26 of vas duct 20 clamped between jaws 408 and 428. When coagulation is complete, clamp 100 is moved downward relative to coagulating device 400 so as to excise duct portion 27 retained within eyelet 103 of clamp 100 as shown in FIGS. 32A and 32B. Jaws 428 and 408 are then unclamped from vas portion 26 and removed. FIGS. 33A and 33B depict scrotum 10 and duct 20 prior to returning the divided duct 20 to scrotum 10. Coagulated end portions 28 of duct portion 26 occlude the vas duct, and also seal the occluded duct ends within the coagulated ends of the vas sheath so as to provide fascial interposition. FIG. 34 depicts vas 20 with occluded coagulated ends 28 returned to scrotum 10. The procedure is repeated on the second vas duct to complete the vasectomy. Occlusion of the two ducts may be accomplished through a single opening or through two openings depending on the surgeon's preference. Optionally the surgeon may excise duct portion 27 after coagulation using a third conventional cutting instrument such as, for instance, a scalpel, dissecting forceps, scissors, biopsy punch, or other surgical device.

In an alternate embodiment, the procedure of the present invention for occluding a vas duct may be modified such that the excising clamp 100 is replaced by an excising hook 200 of the present invention. Referring to FIGS. 35 through 39, excising hook 200 has a proximal handle portion 202 and an elongate distal portion 204 with a distal end portion 206. Distal end portion 206 has parallel planar lateral surfaces 212 spaced distance 214 apart, distance 214 being slightly less than width 480 of slots 409 and 429 of jaws 408 and 428 of bipolar device 400 (see FIG. 19A). Distal hook portion 208 has an inner surface perpendicular to lateral surfaces 212 so as to form a sharp edge. Hook 200 is formed of a suitable dielectric material, either polymeric or ceramic. In a preferred embodiment, distal portion 204 is formed of a ceramic material and handle portion 202 is formed of a polymeric material.

Figure 40:
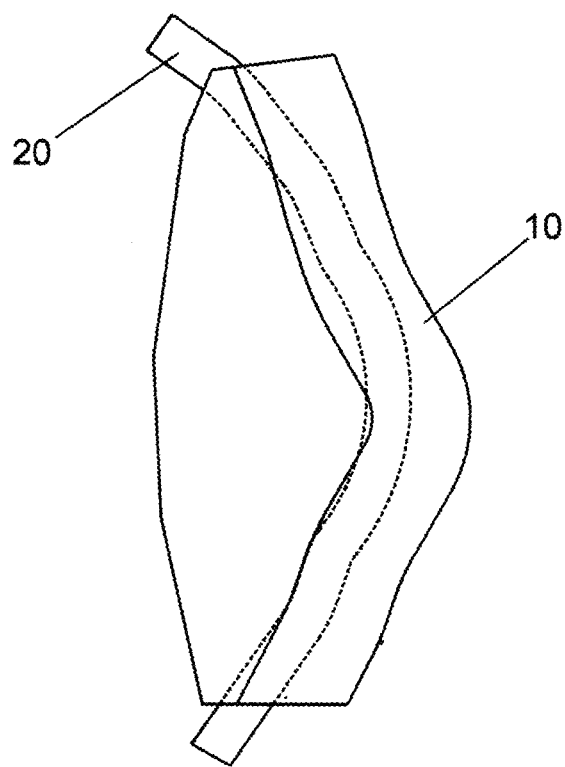
FIG. 40 is a plan view of a vas duct portion within a portion of scrotum.
Figure 41:
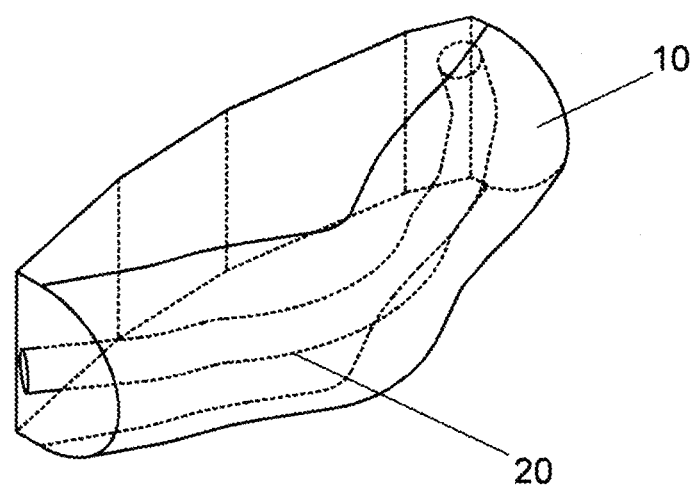
FIG. 41 is a perspective view of the objects of FIG. 40.
Figure 42:
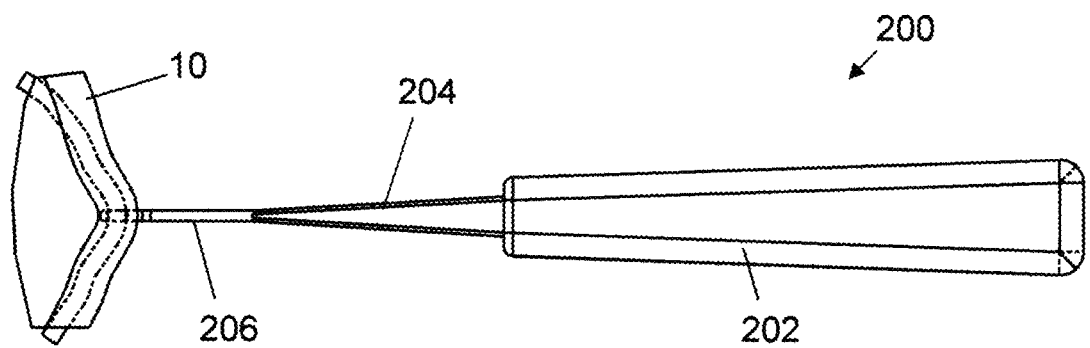
FIG. 42 is a plan view depicting the vas duct and scrotum portion, wherein the duct portion is captured in the excising hook of FIG. 35.
Figure 43:
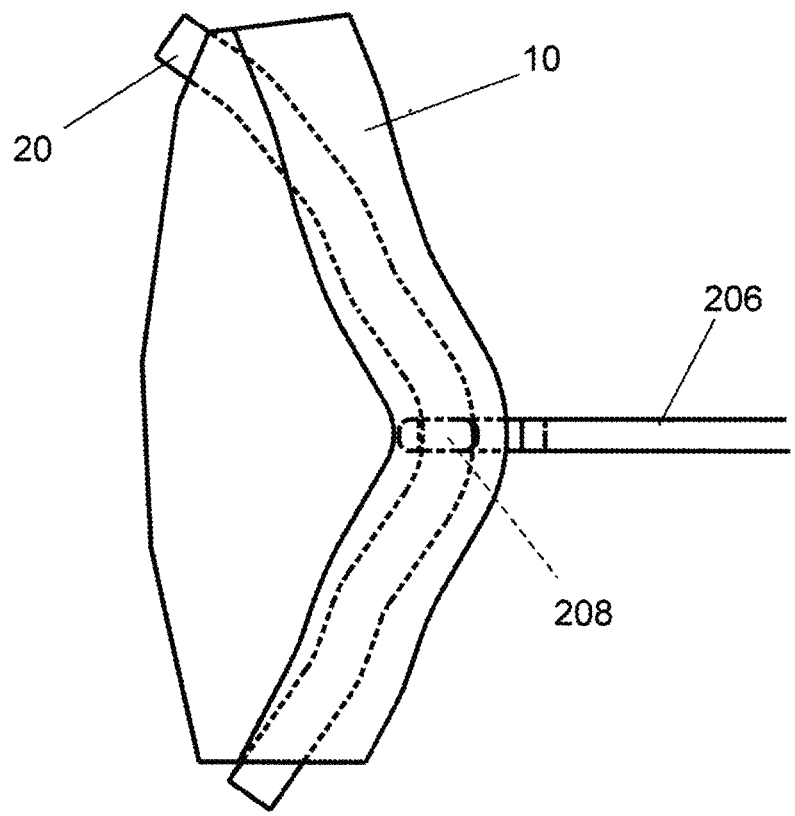
FIG. 43 is an expanded view of the distal portion of the objects of FIG. 42.
Figure 44:
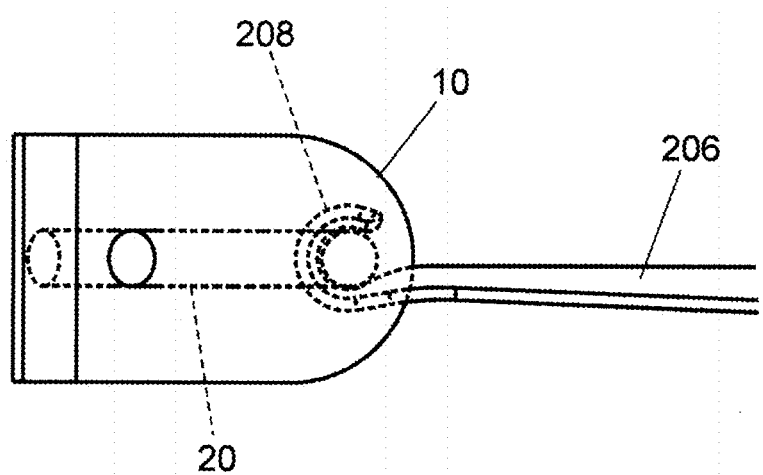
FIG. 44 is a side elevational view of the objects of FIG. 43.
Figure 45:
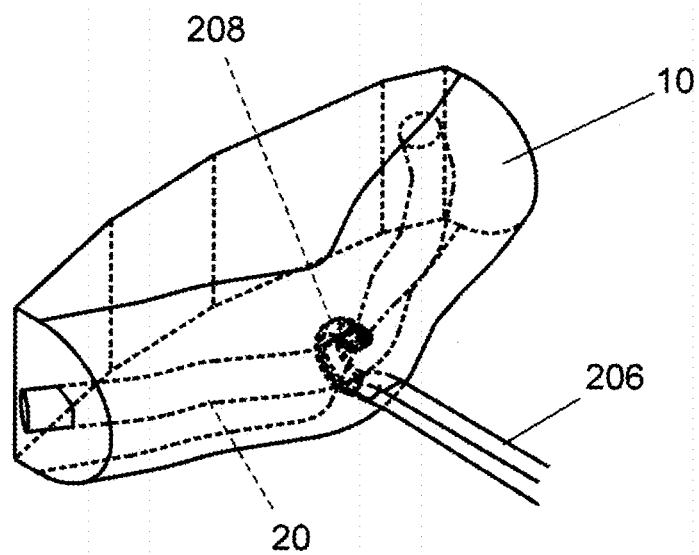
FIG. 45 is a perspective view of the objects of FIG. 43.
Figure 46:
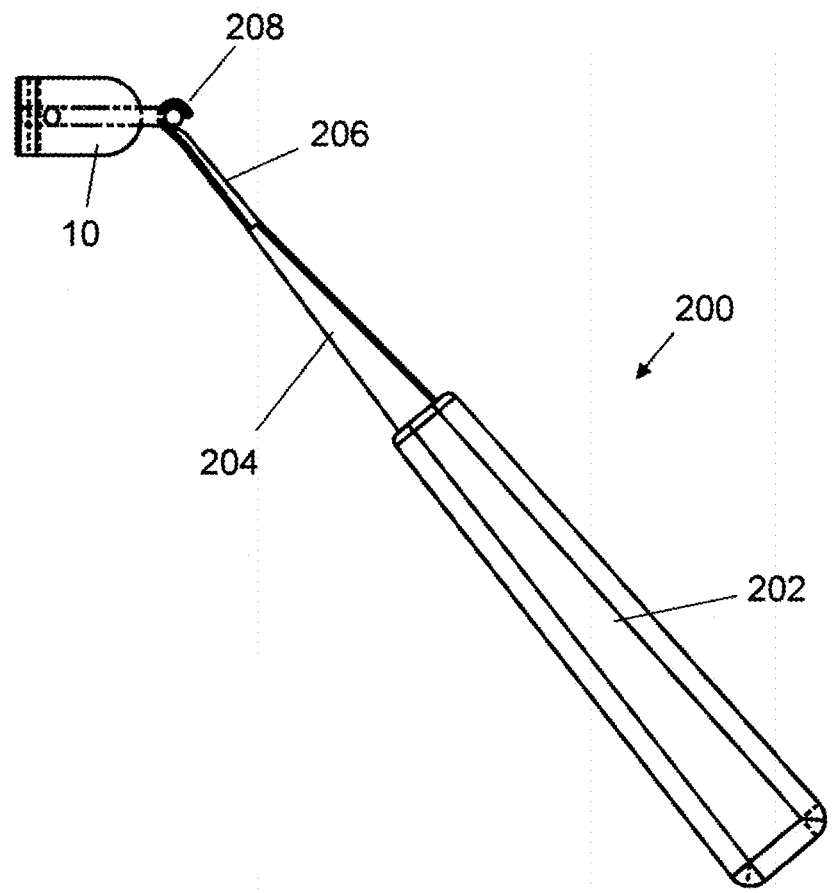
FIG. 46 is a side elevational view of the objects of FIG. 42, wherein a portion of the vas duct has been delivered from the scrotum.
Figure 47:
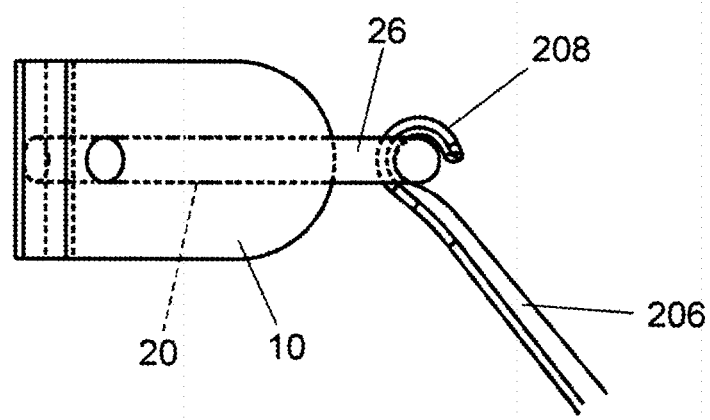
FIG. 47 is an expanded view of the distal portion of the objects of FIG. 46.
Figure 48:
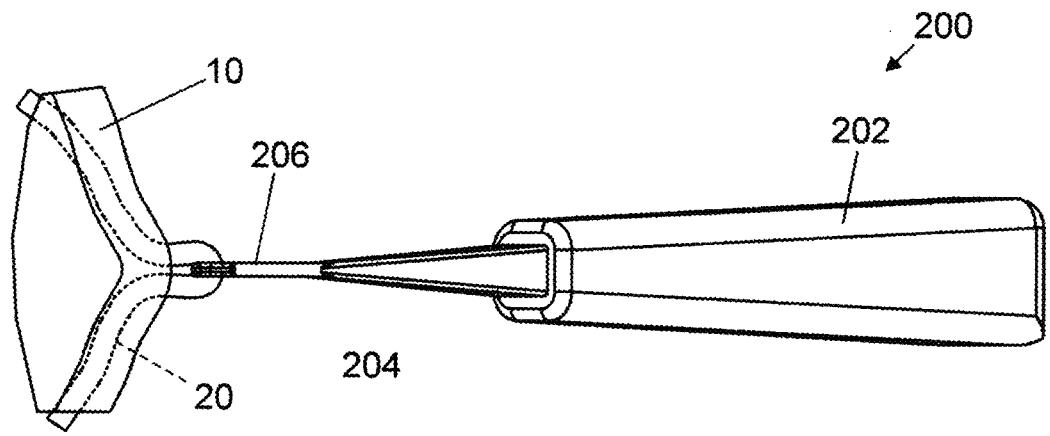
FIG. 48 is a plan view of the objects of FIG. 46.
Figure 49:
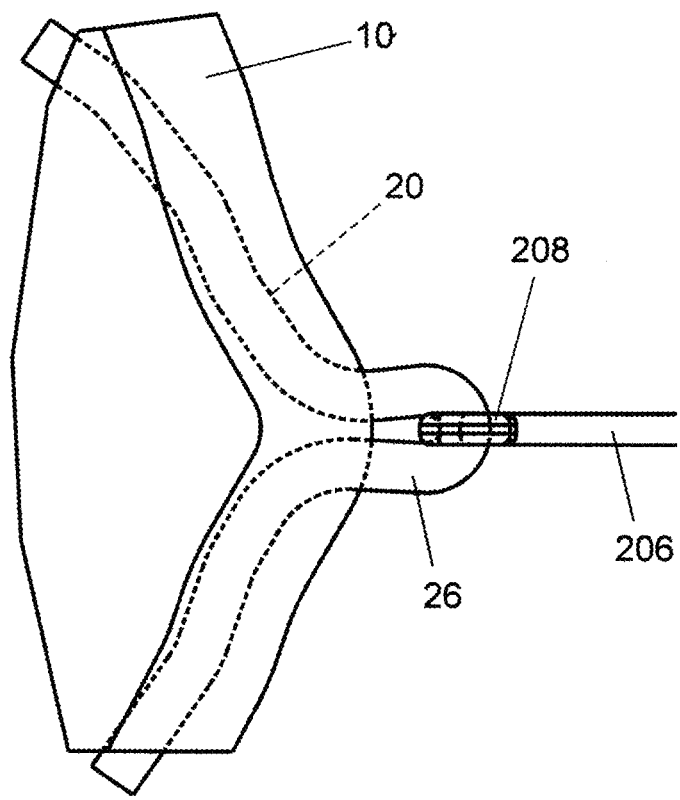
FIG. 49 is an expanded view of the distal portion of the objects of FIG. 48.
Figure 50:
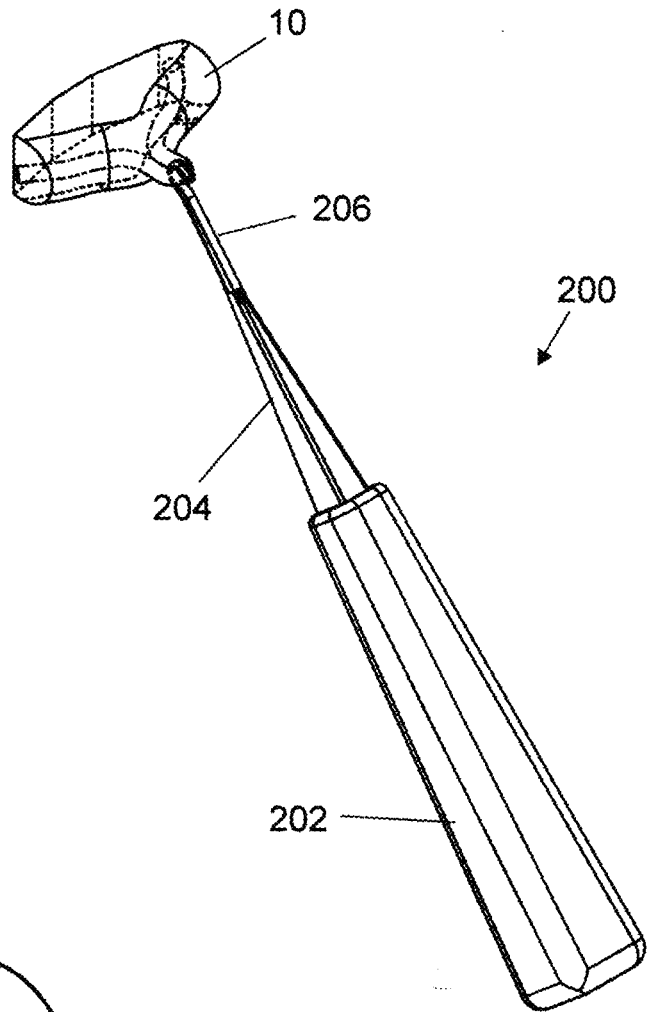
FIG. 50 is a perspective view of the objects of FIG. 46.
Figure 51:
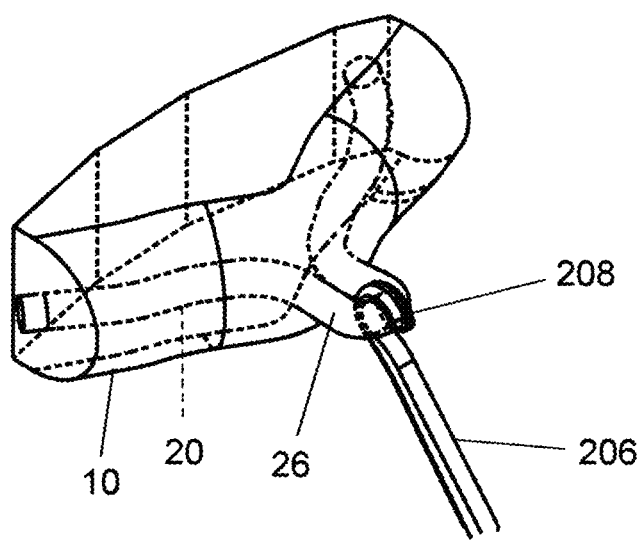
FIG. 51 is an expanded view of the distal portion of the objects of FIG. 50.
Figure 52:
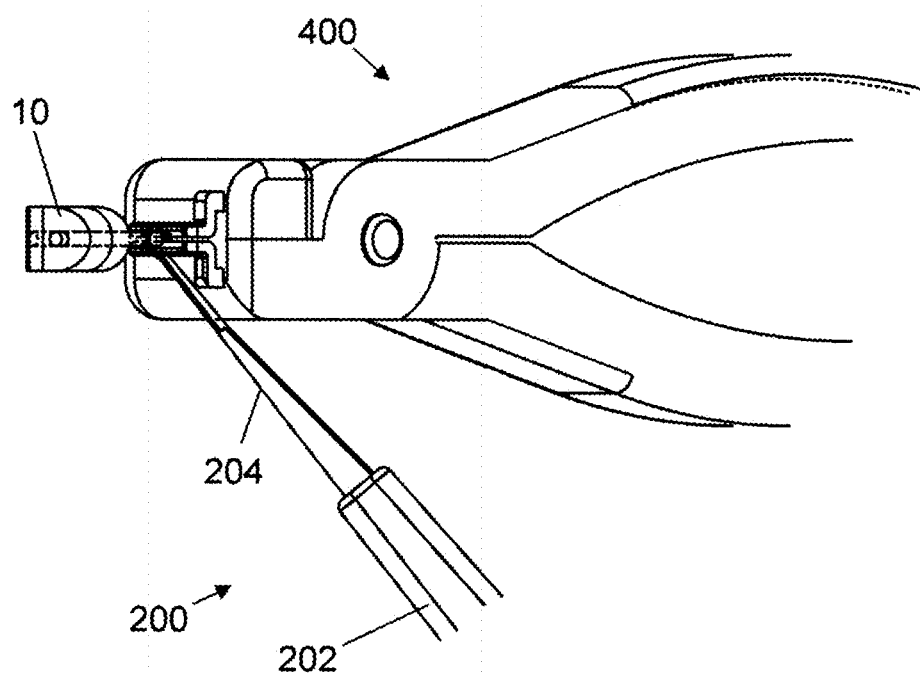
FIG. 52 is a side elevational view of the objects of FIG. 46, further wherein the vas duct portion external to the scrotum is clamped between the jaws of a bipolar coagulating device.
Figure 53:
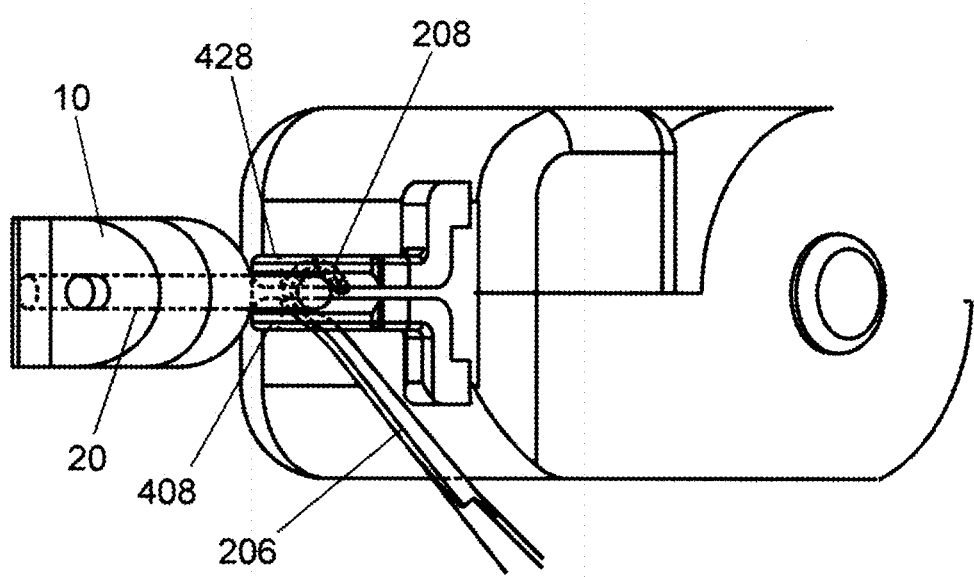
FIG. 53 is an expanded view of the distal portion of the objects of FIG. 52.
Figure 54:
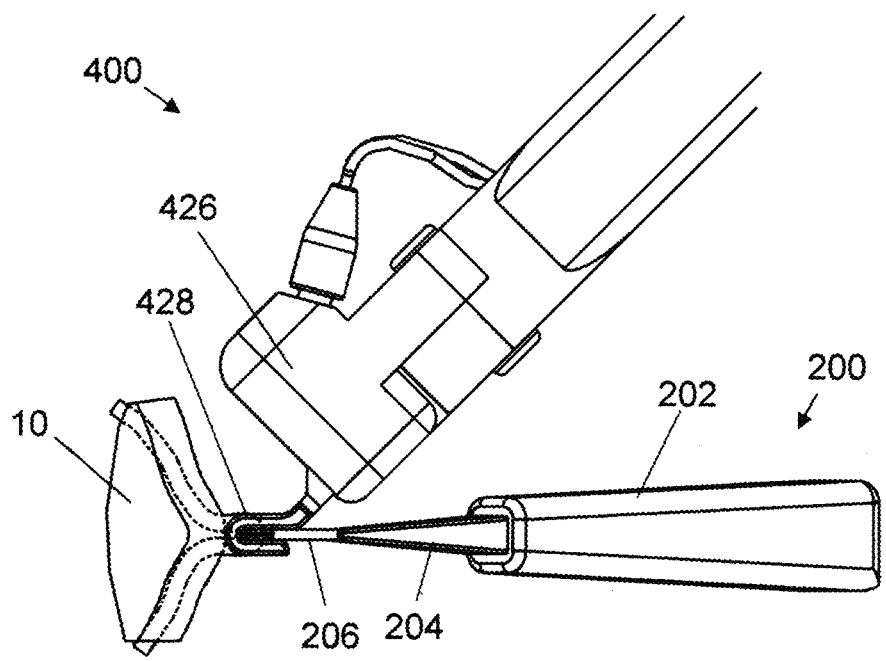
FIG. 54 is a plan view of the objects of FIG. 52.
Figure 55:
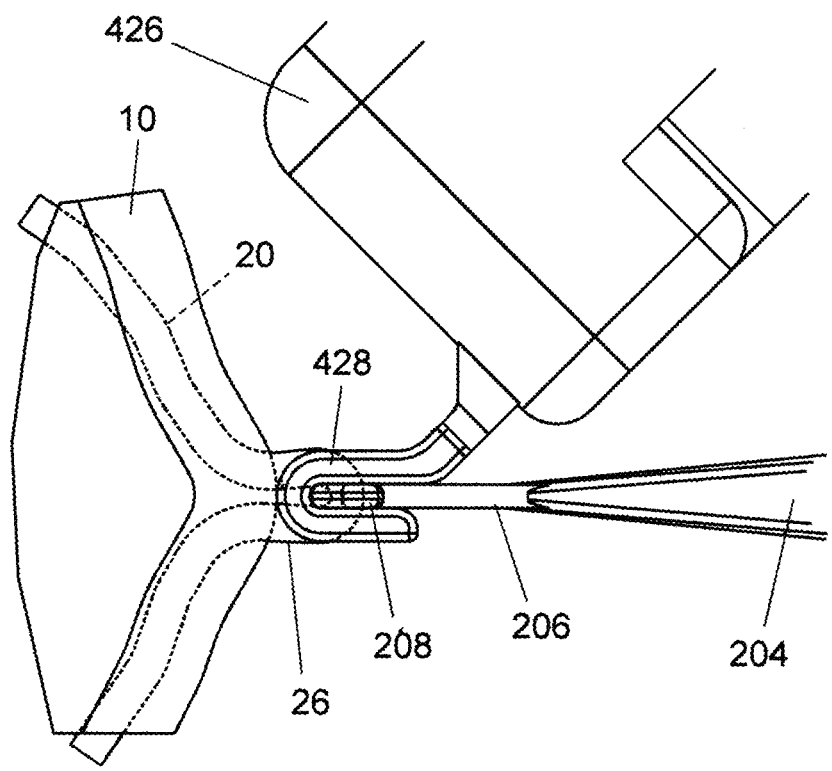
FIG. 55 is an expanded view of the distal portion of the objects of FIG. 54.
Figure 56:
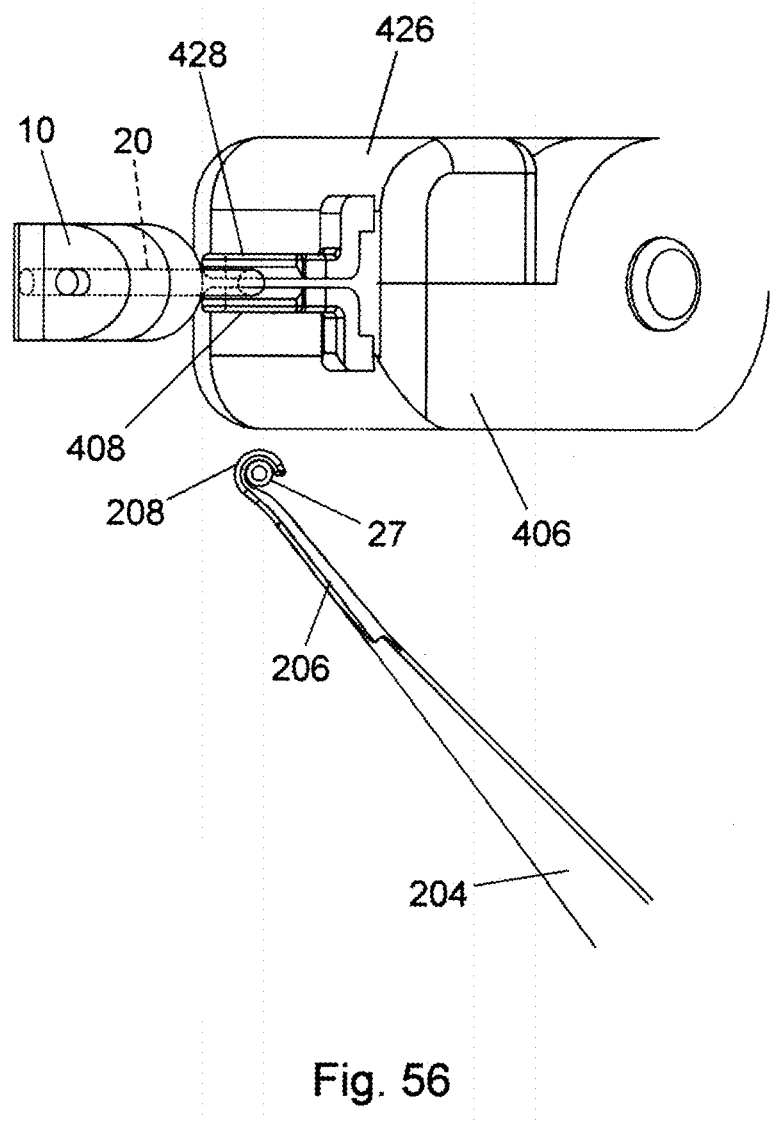
FIG. 56 is a side elevational view of the objects of FIG. 52, further wherein an uncoagulated portion of the vas duct has been removed by the excising hook.
Figure 59:
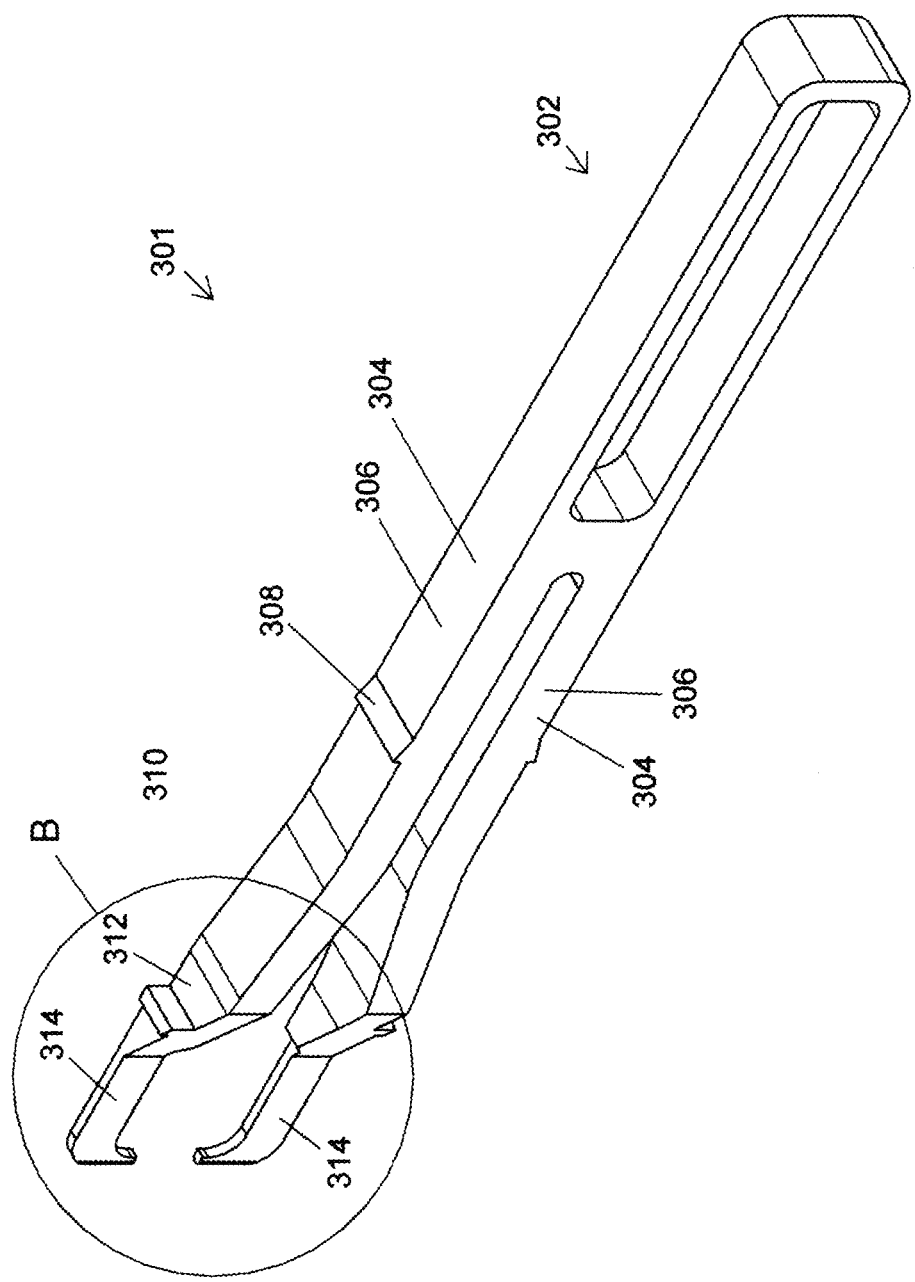
FIG. 59 is a perspective view of the objects of FIG. 57.
Figure 60:
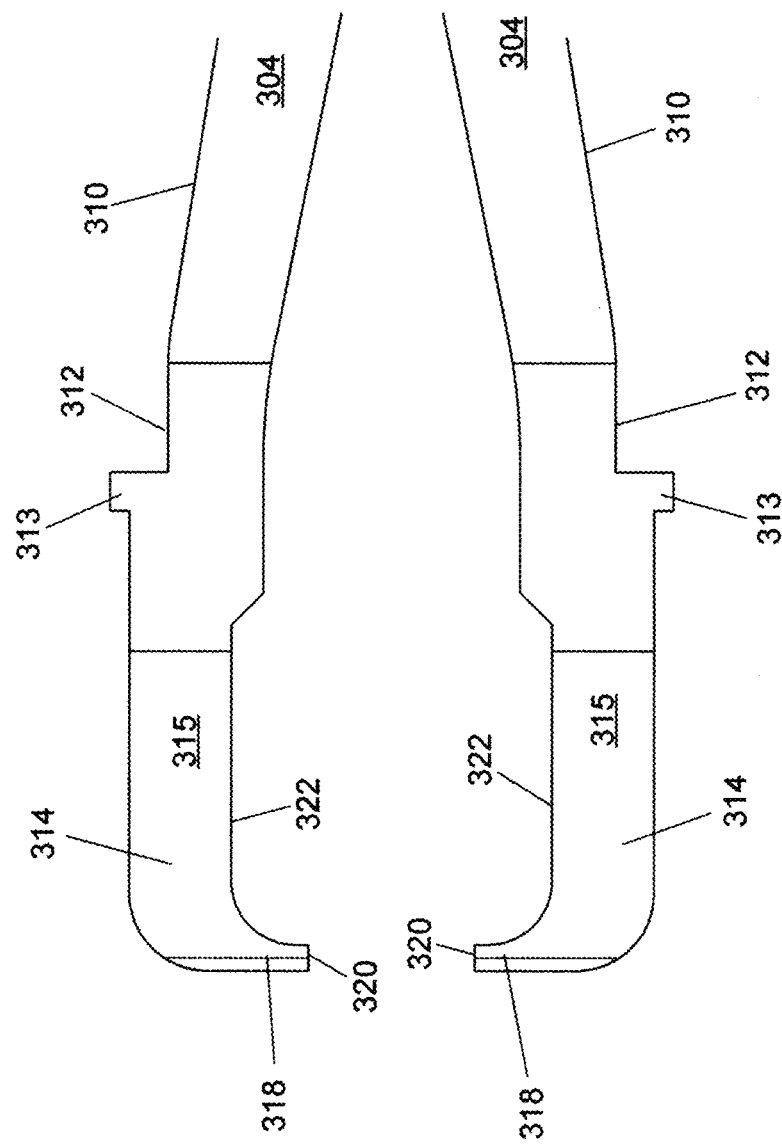
FIG. 60 is an expanded view of the objects of FIG. 58 at location A.
Figure 61:
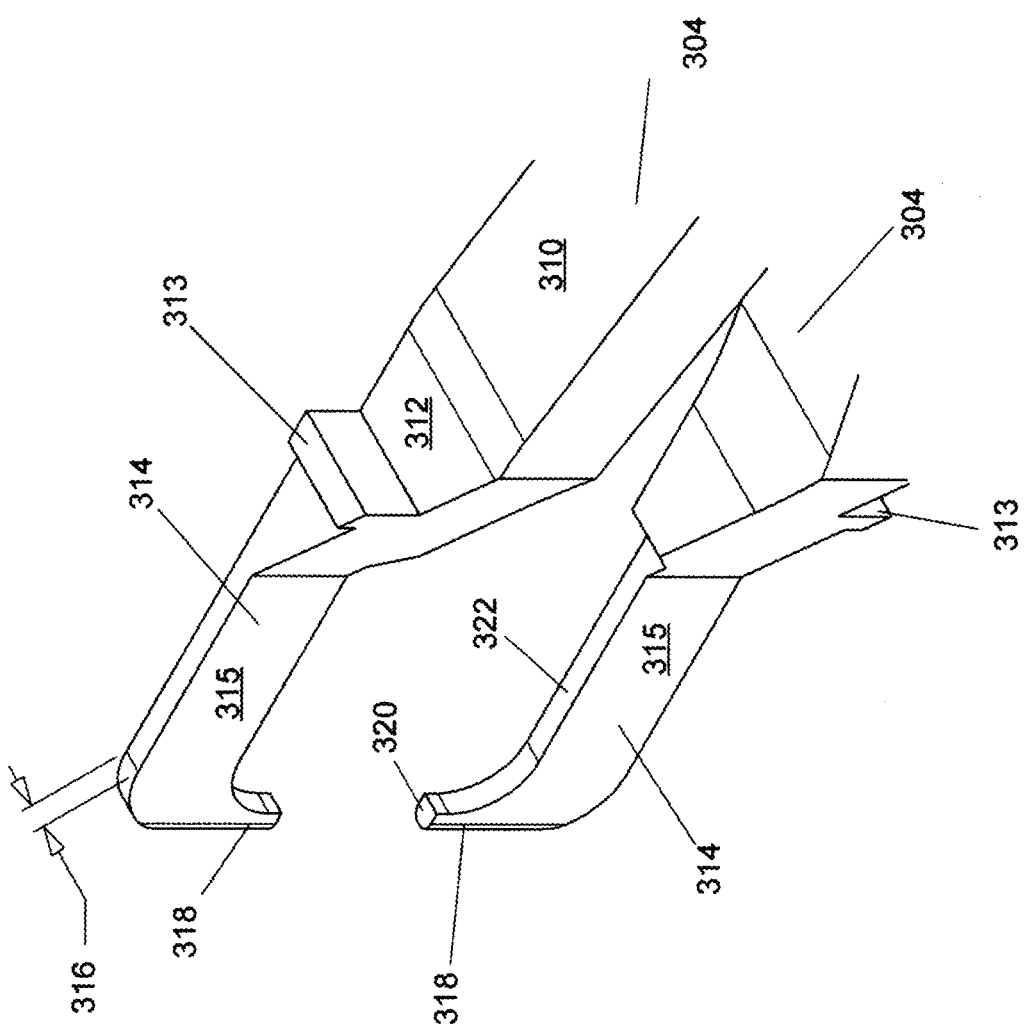
FIG. 61 is an expanded view of the objects of FIG. 59 at location B.

In this alternative method of the present invention for occluding and dividing a vas duct, excising hook 200 and bipolar coagulating device 400 are used in the same manner as previously described with respect to excising clamp 100 and coagulating device 400 except as subsequently specifically described. FIGS. 40 and 41 depict vas duct 20 located within a fold of scrotum 10, duct 20 being positioned therein and the region injected with a local anesthetic using standard NSV methods. An opening is then formed in scrotum 10 proximate to duct 20 using a dissecting forceps in the usual manner. Thereafter, as shown in FIGS. 42 through 45, distal portion 206 of excising hook 200 is inserted into scrotum 10 through the opening formed therein and duct 20 is captured in distal hook portion 208. The clinician may, optionally, grasp the vas after forming the opening in the scrotum with the dissecting forceps or another device to position the vas for capture by hook 200. Handle 202 of excising hook 200 is then pivoted downward and proximal so as to deliver duct 20 from scrotum 10 as depicted in FIGS. 46 to 51. Portion 26 of vas duct 20 remains captured within hook portion 208 of excising hook 200. Jaws 408 and 428 of coagulating device 400 are then positioned about hook portion 208 of excising hook 200 and clamped onto portion 26 of vas duct 200 as depicted in FIGS. 52 through 55. Radio frequency energy supplied to jaws 408 and 428 of coagulating device 400 by electrosurgical generator 13 along with pressure applied by jaws 408 and 428 coagulates portions of duct portion 26 clamped between the jaws in the manner previously described so as to occlude duct portion 26. After coagulation is complete, excising hook 204 is displaced downward relative to jaws 408 and 428 of coagulating device 400 so as to excise an uncoagulated duct portion 27 from the coagulated portions of duct portion 26 clamped between jaws 408 and 428 to divide duct 20. Excision is accomplished through cooperative action of the cutting edges formed between surface 210 and lateral surfaces 212 of excising clamp 200, and the cutting edge 403 of jaw 408 (see FIG. 27K). Thereafter jaws 408 and 428 are unclamped from the coagulated portions of duct portion 26 and the occluded portions of duct 20 are returned to scrotum 10. The second vas duct is then occluded in the same manner to complete the procedure.

In NSV methods, including the inventive versions described herein, vas ducts are delivered from the scrotum for occlusion and division. In an alternate embodiment, the modified vasectomy methods of the present invention that utilize the novel devices of the present invention avoid the need for the vas duct to be delivered from the scrotum, but rather allow it to remain positioned within a fold of scrotal skin and occluded and divided in situ, without dissection from the scrotum. In this manner, no openings are formed in the scrotum. Because there is no dissection, hematomas are wholly prevented. Likewise, as no sharp instruments are used, the risk to the clinician when performing a vasectomy on a HIV+ patient is substantially reduced. As with the previously described embodiments, excision is accomplished by an excising clamp of the present invention in cooperation with the jaws of bipolar coagulating device 400. FIGS. 57 through 61 depict a body 301 for an alternate embodiment excising clamp of the present invention. Body 301 has a proximal handle portion 302 and upper and lower distally extending portions 304. Portions 304 have proximal parallel portions 306 whereon are positioned proximal stops 308, distal parallel portions 312 with distal stop 313 at their distal ends, and angled portions 310 positioned between proximal and distal parallel portions 306 and 312. Distal portions 314 of thickness 316 have distal-most portions forming opposed jaws 318 with symmetrically opposed faces 320, and adjacent symmetrically opposed faces 322. The edges between surfaces 320 and 322 and the laterally opposed faces 315 of distal portions 314 are orthogonal and have minimum edge radii.

Figure 62:
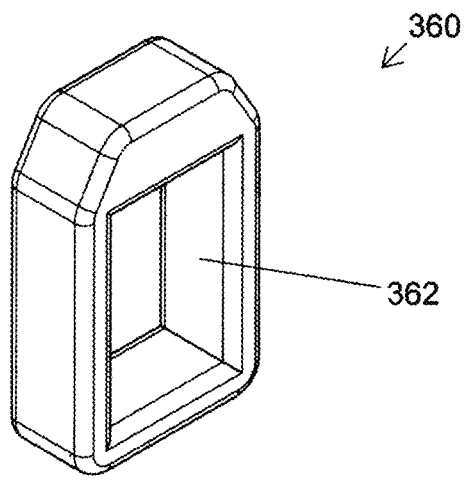
FIG. 62 is a perspective view of an excising clamp ring in accordance with the present invention.
Figure 63:
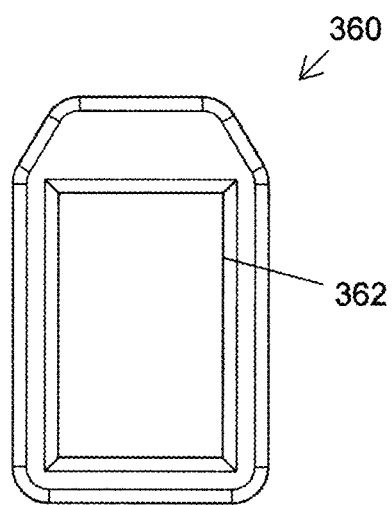
FIG. 63 is an axial view of the objects of FIG. 62.
Figure 64:
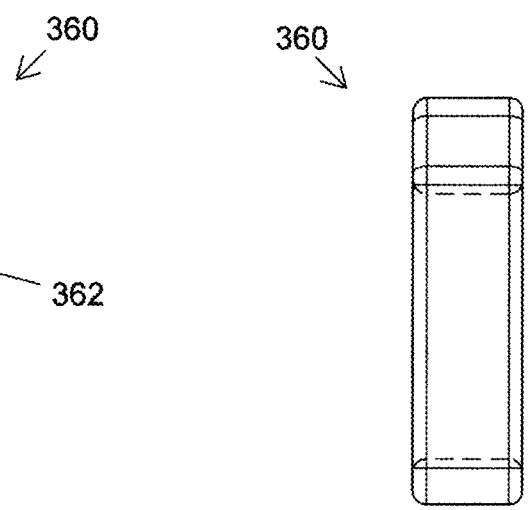
FIG. 64 is a side elevational view of the objects of FIG. 62.

Referring now to FIGS. 62 through 64 depicting a control ring 360 for an excising clamp of the present invention, ring 360 has a central opening 362 configured to be slidably received on the proximal parallel portions 306 of distally extending portions 304 of body 300.

Excising clamp body 301 and ring 360 are formed of a suitable dielectric material. In a preferred embodiment body 100 and ring 200 are formed of a polymeric material by injection molding or other suitable process.

Figure 67:
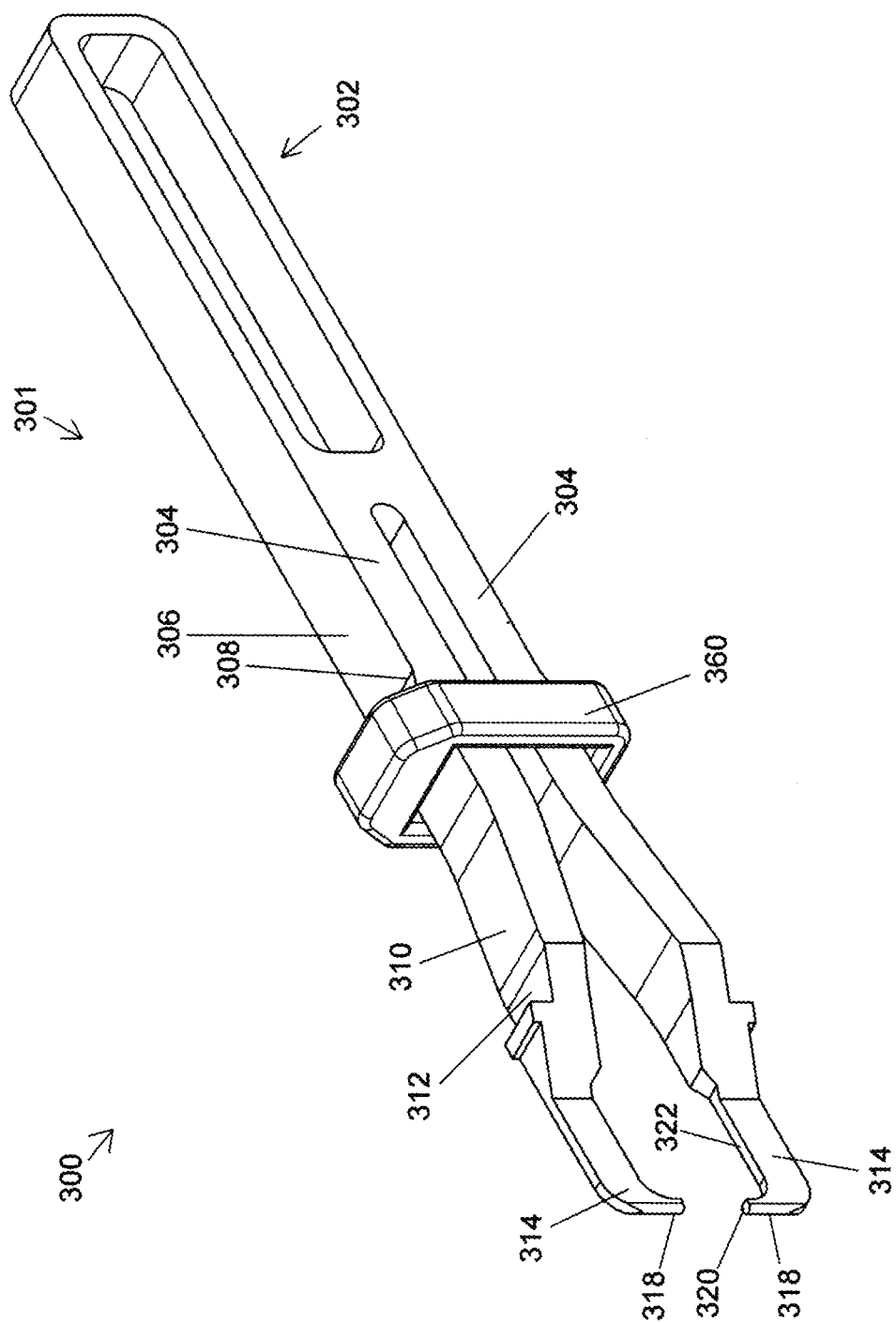
FIG. 67 is a perspective view of the objects of FIG. 65.
Figure 70:
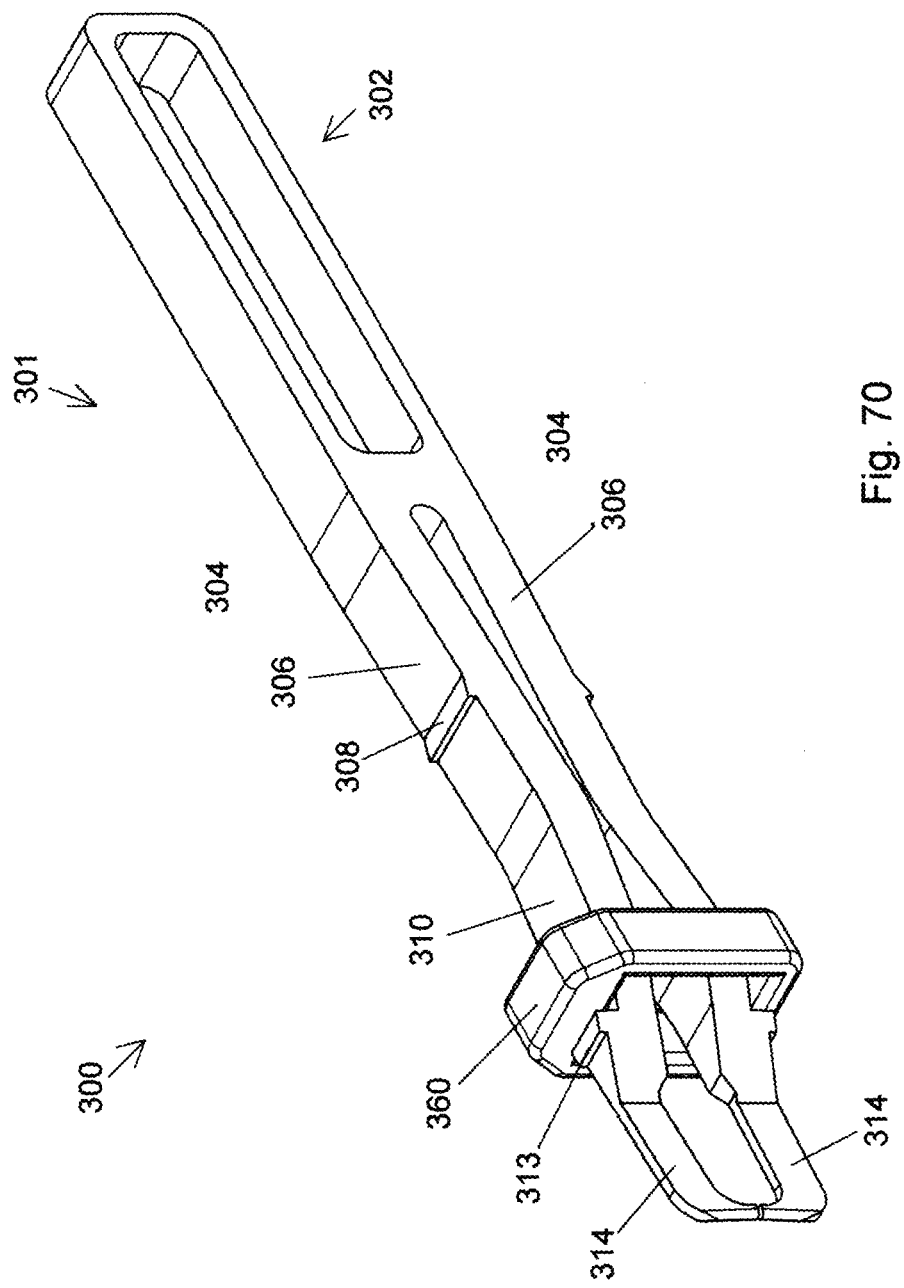
FIG. 70 is a perspective view of the objects of FIG. 68.
Figure 71:
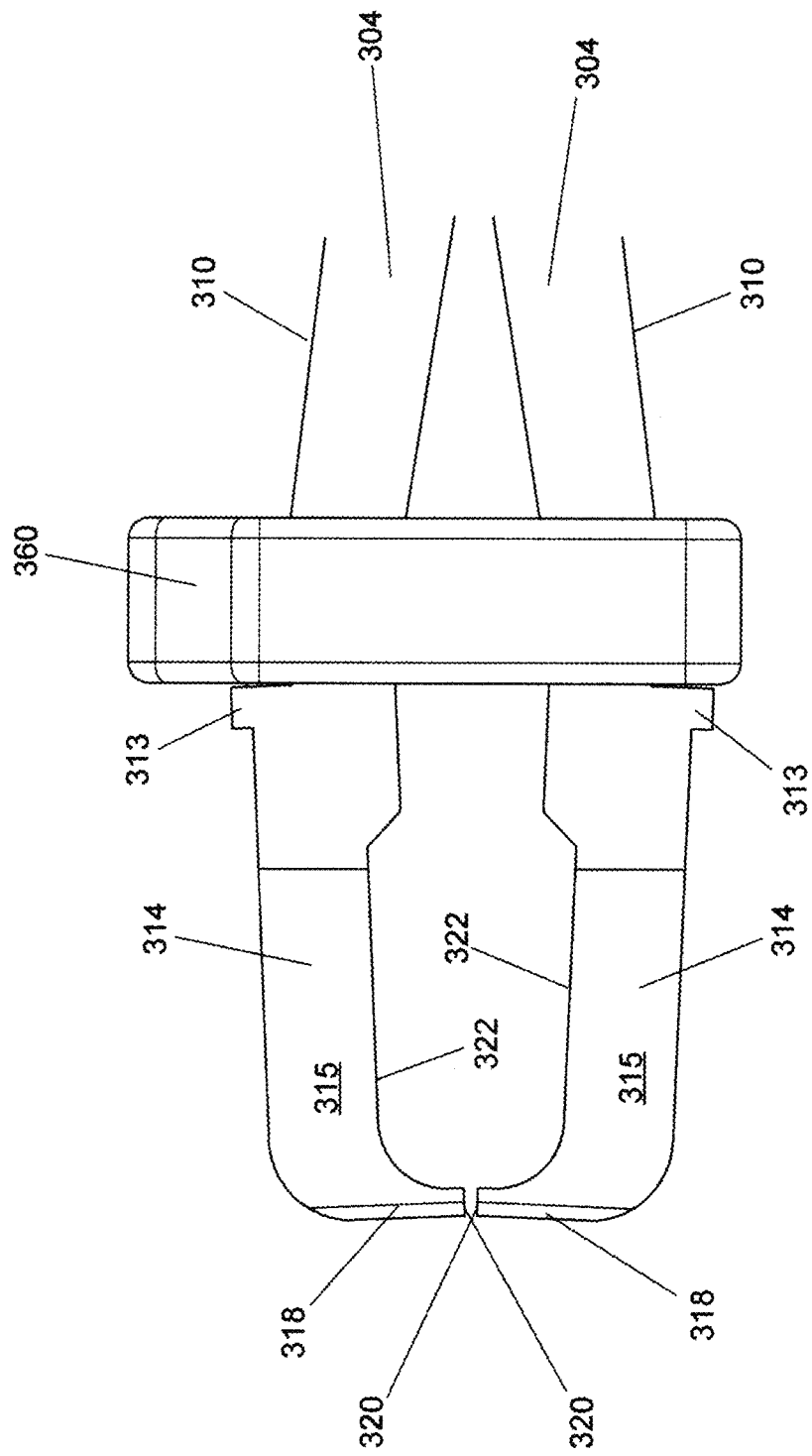
FIG. 71 is an expanded view of the objects of FIG. 69 at location A.

Excising clamp 300 of the present invention is depicted in its open (unclamped) position in FIGS. 65 through 67. Ring 360 is positioned on proximal parallel portions 306 of distally extending portions 304 of body 301, distal to proximal stops 308. In an unconstrained condition, stops 308 protrude beyond the upper and lower surfaces of opening 362 in ring 360, ring 360 being moved distal to stops 308 by deflecting distally extending portions 304 inward. Surfaces 320 of jaws 318 are separated by distance 324 in the unclamped condition depicted.

Figure 73:
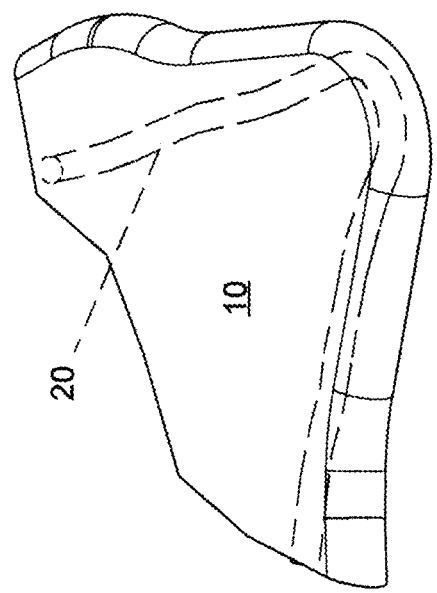
FIG. 73 is a perspective view of the objects of FIG. 72.
Figure 72:
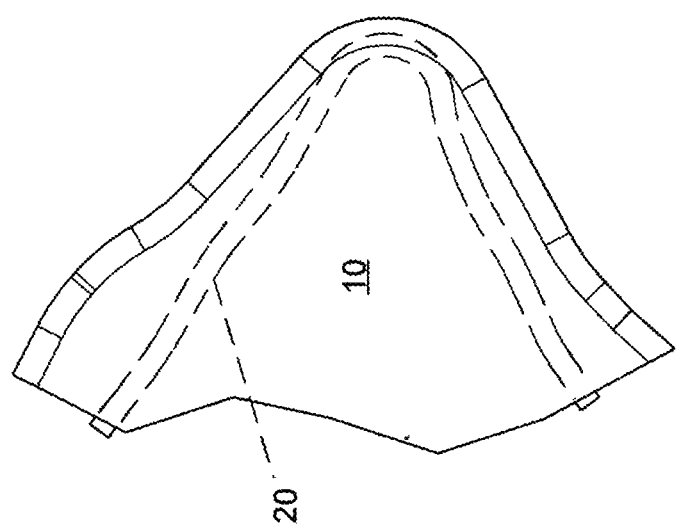
FIG. 72 is a plan view of a portion of a scrotum with a vas duct located in a fold thereof.
Figure 74:
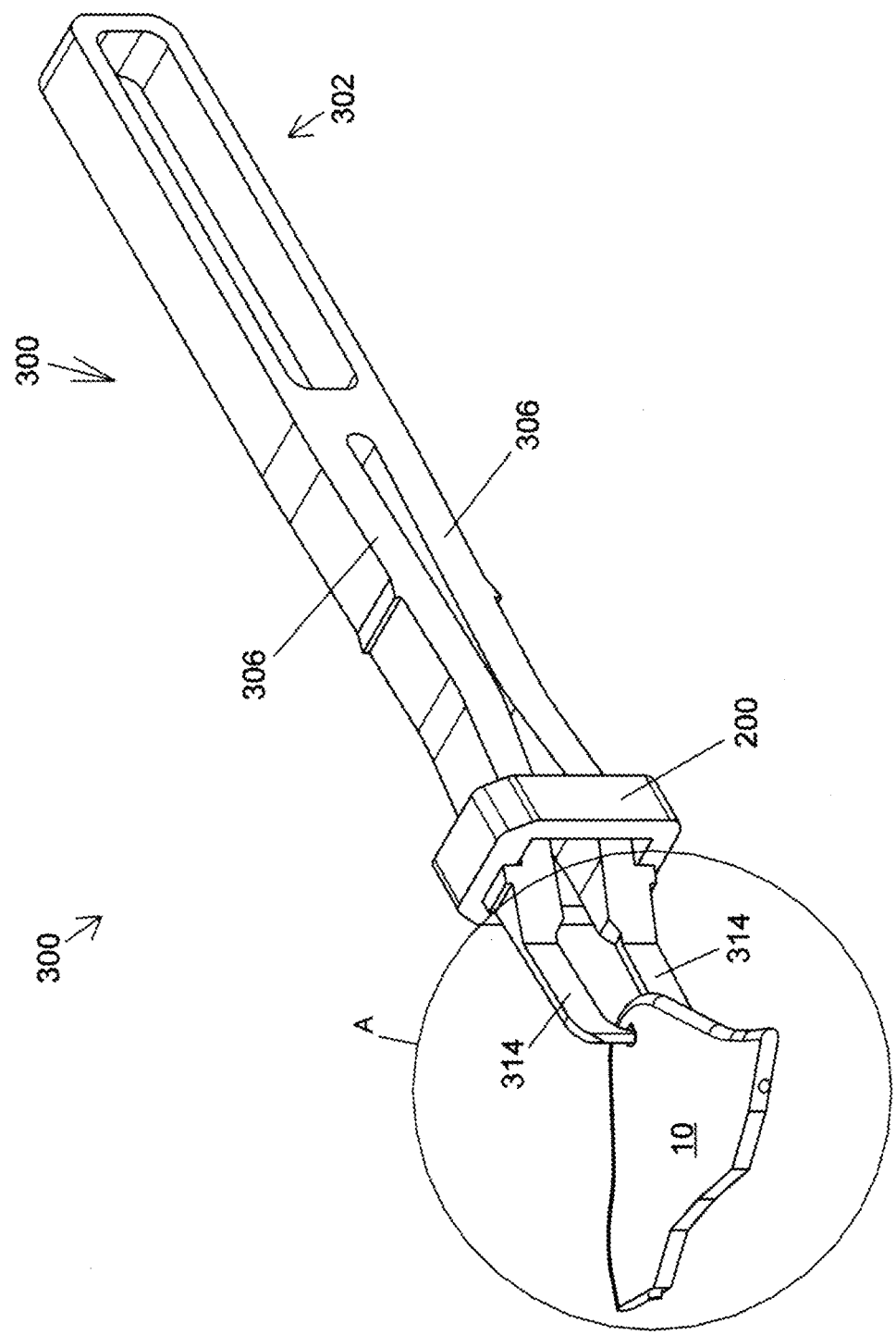
FIG. 74 is a perspective view of the alternate excising clamp of FIG. 65 applied to the objects of FIG. 72 so as to maintain the position of the vas duct in the fold of scrotal tissue.
Figure 75:
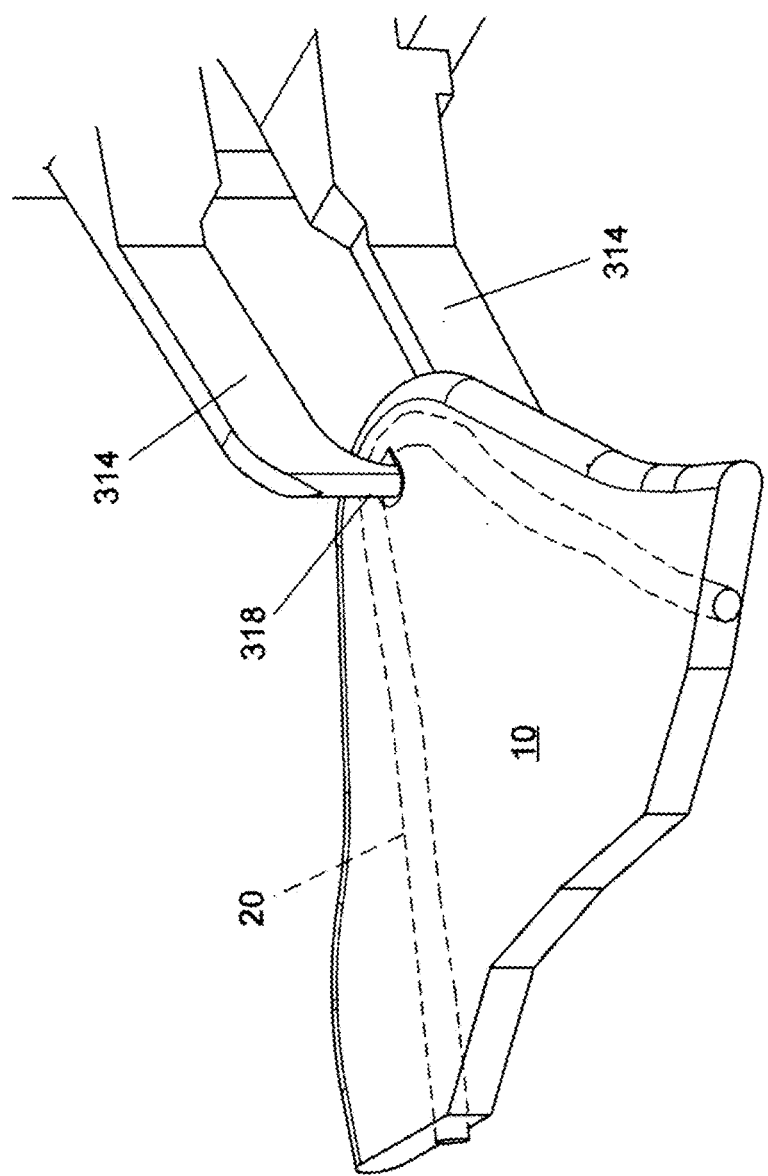
FIG. 75 is an expanded view of the objects of FIG. 74 at location A.
Figure 76:
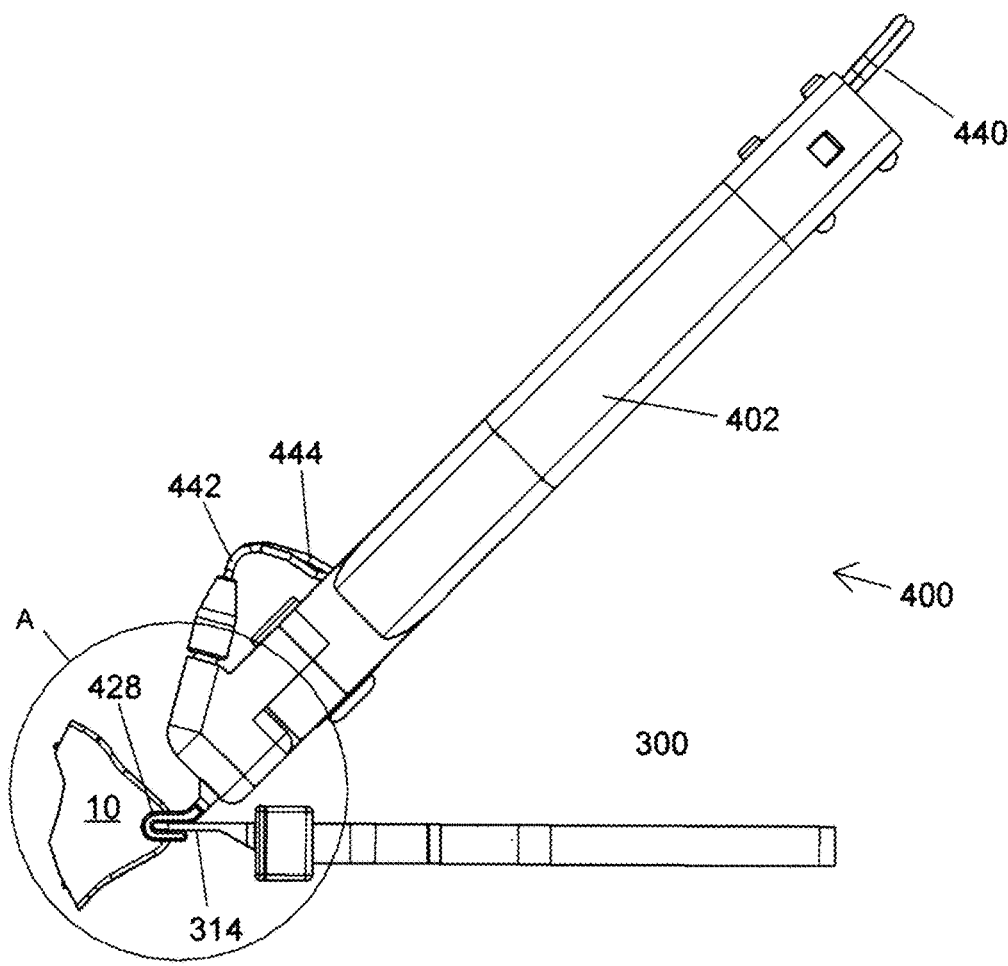
FIG. 76 is a plan view of the scrotum and clamp of FIG. 75 positioned within the jaws of the electrosurgical device of FIG. 16.
Figure 77:
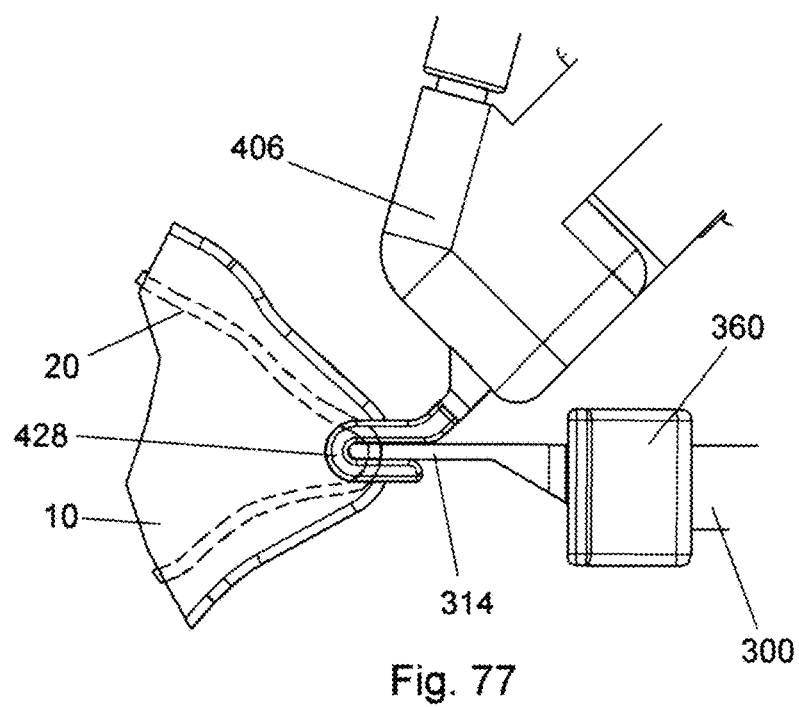
FIG. 77 is an expanded view of the objects of FIG. 76 at location A.
Figure 78:
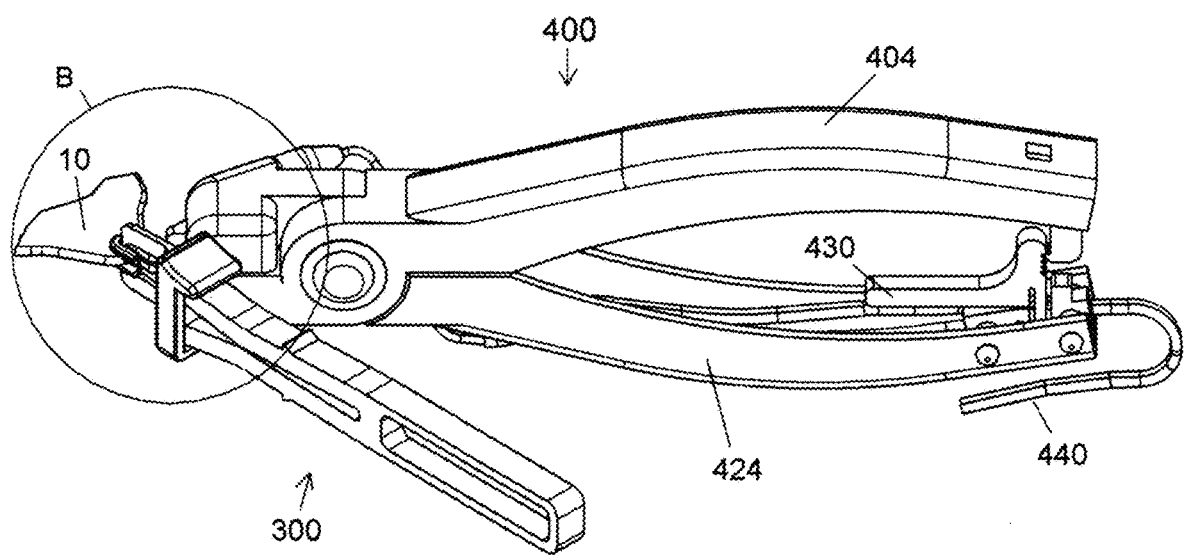
FIG. 78 is a perspective view of the objects of FIG. 76.
Figure 79:
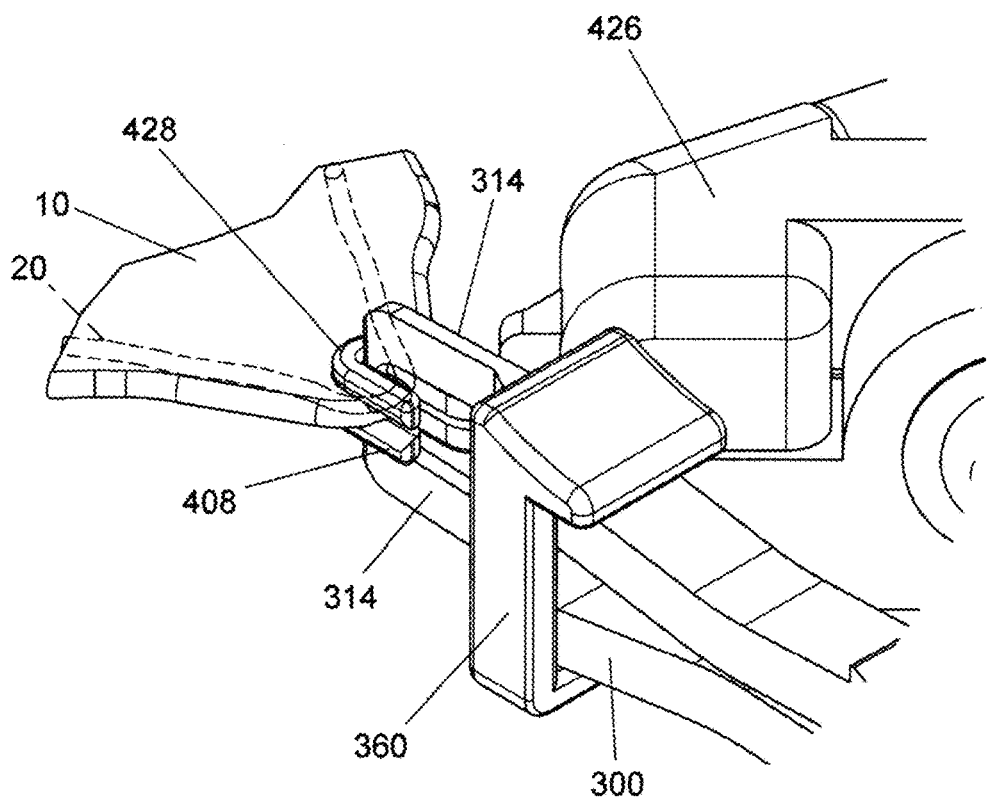
FIG. 79 is an expanded view of the objects of FIG. 78 at location B.
Figure 80:
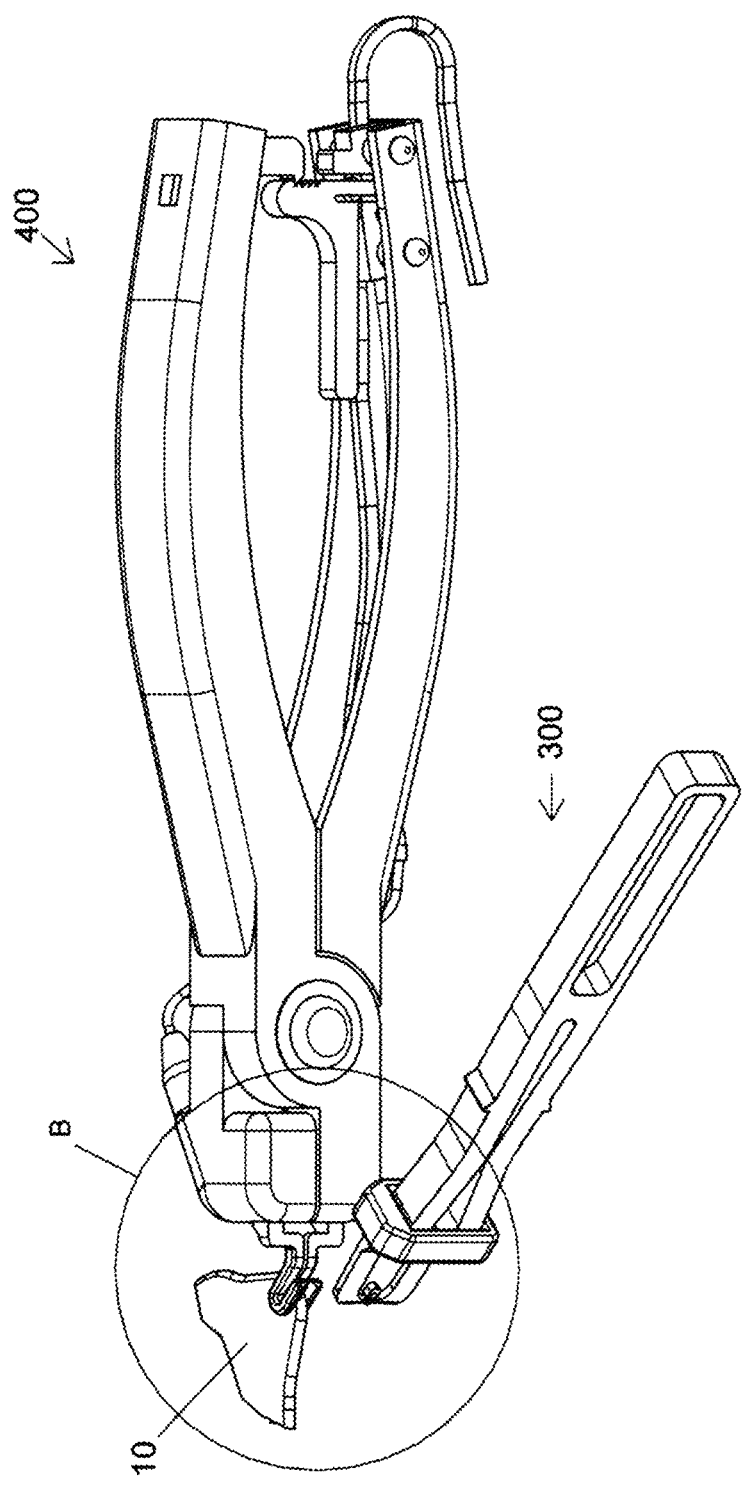
FIG. 80 is a perspective view of the objects of FIG. 76 wherein the excising clamp has been displaced downward so as to excise a portion of the vas duct.
Figure 81:
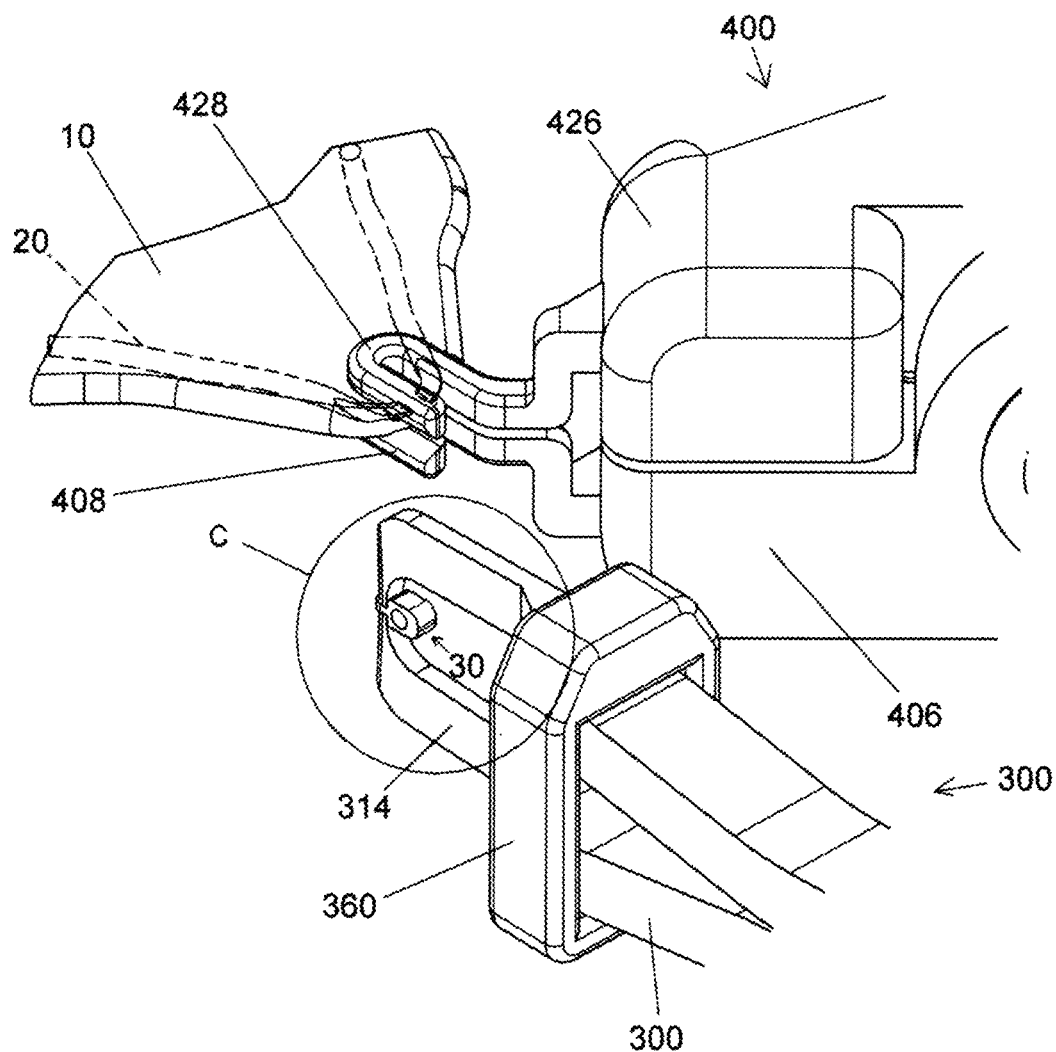
FIG. 81 is an expanded view of the objects of FIG. 80 at location B.

Clamping tissue between opposed surfaces 320 of clamp body 301 is accomplished by moving ring 360 distally over angled portions 310 of clamp body 301 so as to deflect distally extending portions 304 toward each other as depicted in FIG. 68 to 71. Ring 360 is moved distally until it reaches distal parallel portions 312 encountering distal stop 313. In this closed position, opposed faces 320 are in close proximity to each other, or optionally may be in contact. In a first step of a vasectomy procedure according to methods of the present invention, a first vas duct is isolated in a fold of scrotal skin as depicted in FIGS. 72 and 73 wherein duct 20 is located in a fold of scrotal skin 10. In FIGS. 74 and 75, clamp 300 is applied to the fold of scrotal skin 10 with jaws 318 medial to duct 20 so as to maintain the position of duct 20 in the fold, and ring 360 is advanced to its distal position so as to close jaws 318 on the tissue. Thereafter, upper and lower jaws 408 and 428 of handpiece 400 are positioned around distal portion 314 of clamp body 301 of clamp 300 and handpiece 400 is closed so as to apply compressive force to the tissue between jaws 408 and 428 as shown in FIGS. 76 through 79. The clamping force may be maintained by ratchet element 430 of lower handle assembly 422. Subsequently RF energy from electrosurgical generator 13 (FIG. 26) is supplied to jaws 408 and 428 by wires 442 and 444 and cable 440 so as to coagulate portions of scrotal skin 10 and vas duct 20 that are compressed between jaws 408 and 428. When coagulation is complete, clamp 300 is moved relative to jaws 408 and 428 so that the central uncoagulated tissue portion 30 containing scrotal skin 10 and a portion of vas duct 20 is removed as depicted in FIGS. 80 and 81. Tissue portion 30 is removed by cooperative cutting action between an edge of clamp 300 and an edge of lower jaw 408. Specifically, the clamp cutting edge is formed by the intersection of surfaces 320 and 322 with lateral surfaces 315 of the upper distal portion 314 of clamp body 301. The handpiece jaw cutting edge is edge 411 of lower jaw 404. As clamp 300 is moved downward relative to coagulating device or "handpiece" 400 as depicted in FIGS. 80 and 81, initially tissue trapped between surfaces 320 is cut by the portion of edge 411 of jaw 404 in the distal radius of edge 411 adjacent to surface 320 of clamp body 300. Thereafter, as downward motion of clamp 300 continues, tissue trapped between the clamp cutting edge formed by the intersection of surface 322 with lateral surfaces 315 of upper distal portion 314 of clamp 300 and the linear portions of edge 411 of lower jaw 404 is cut. FIGS. 80 and 81 depict handpiece 400 and clamp 300 with the uncoagulated tissue portion 30 after removal of portion 30.

Optionally the surgeon may excise uncoagulated tissue portion 30 after coagulation using a third conventional cutting instrument such as, for instance, a scalpel, dissecting forceps, scissors, biopsy punch, or other surgical device.

Figure 82:
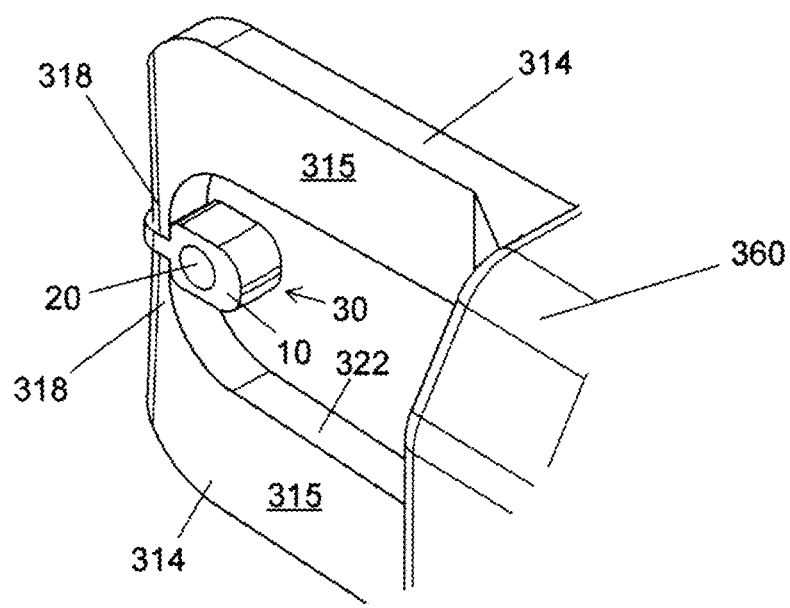
FIG. 82 is an expanded view of the objects of FIG. 81 at location C.
Figure 83:
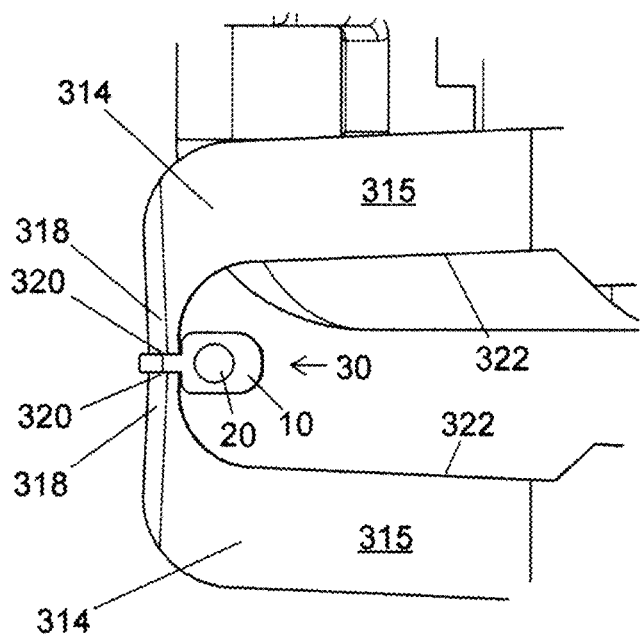
FIG. 83 is a side elevational view of the objects of FIG. 82.

Referring now to FIGS. 82 and 83, tissue portion 30 contains a segment of vas duct 20 comprising the duct and sheath wrapped in a portion of scrotal tissue 10. By examining removed tissue portion 30 under magnification, the clinician can verify that the procedure was successful through visualization of vas duct segment 20 within removed tissue portion 30.

Figure 84:
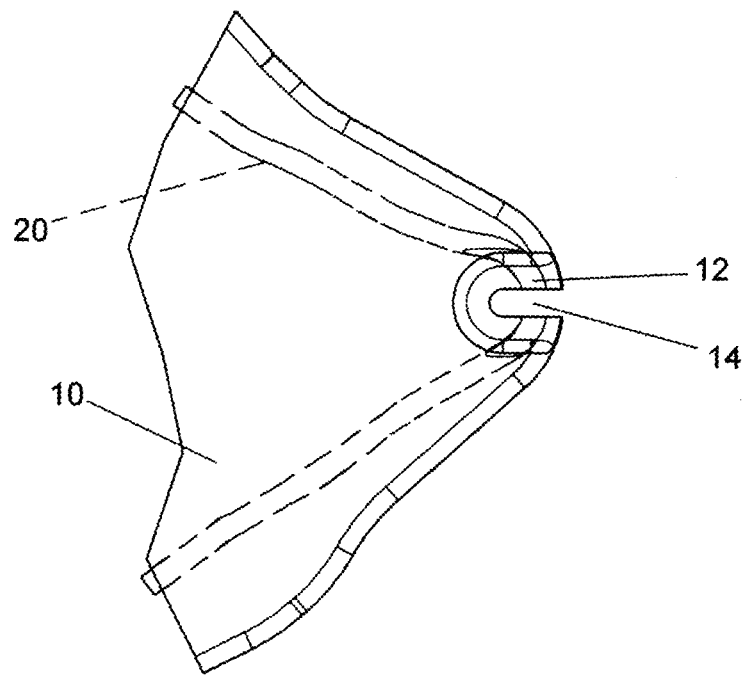
FIG. 84 is a plan view of the treatment site containing the occluded divided vas duct contained in a region of coagulated scrotal tissue.
Figure 85:
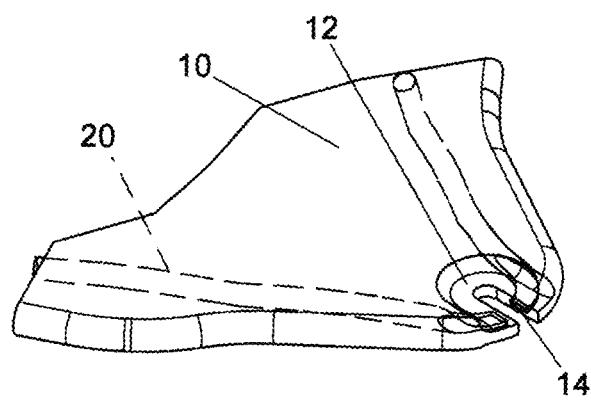
FIG. 85 is a perspective view of the objects of FIG. 84.
Figure 86:
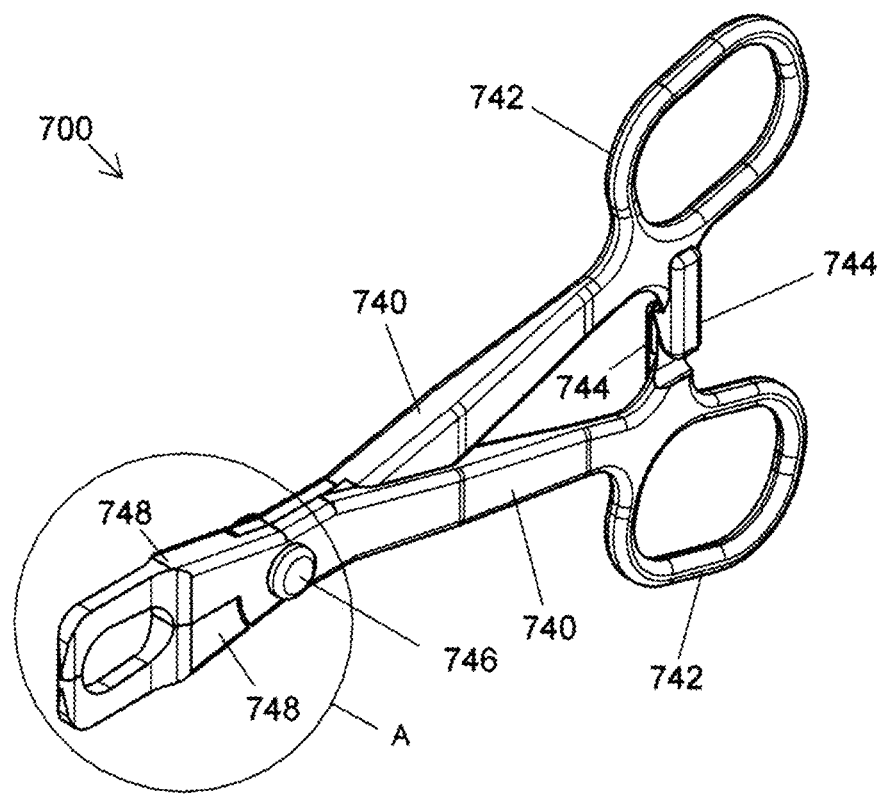
FIG. 86 is a perspective view of yet another alternate embodiment for an excising clamp in accordance with the present invention in a closed (clamped) condition.
Figure 87:
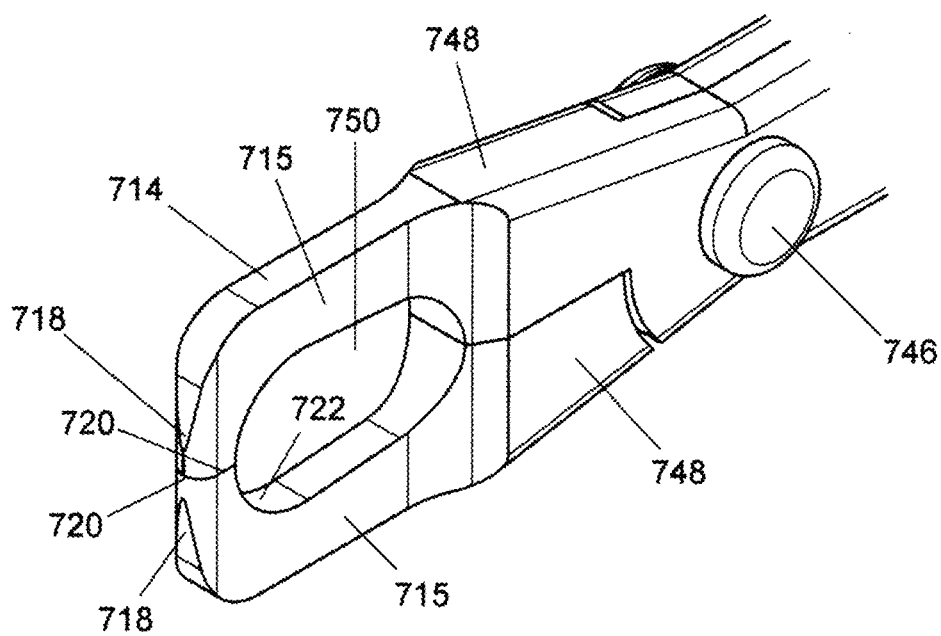
FIG. 87 is an expanded view of the objects of FIG. 86 at location A.
Figure 88:
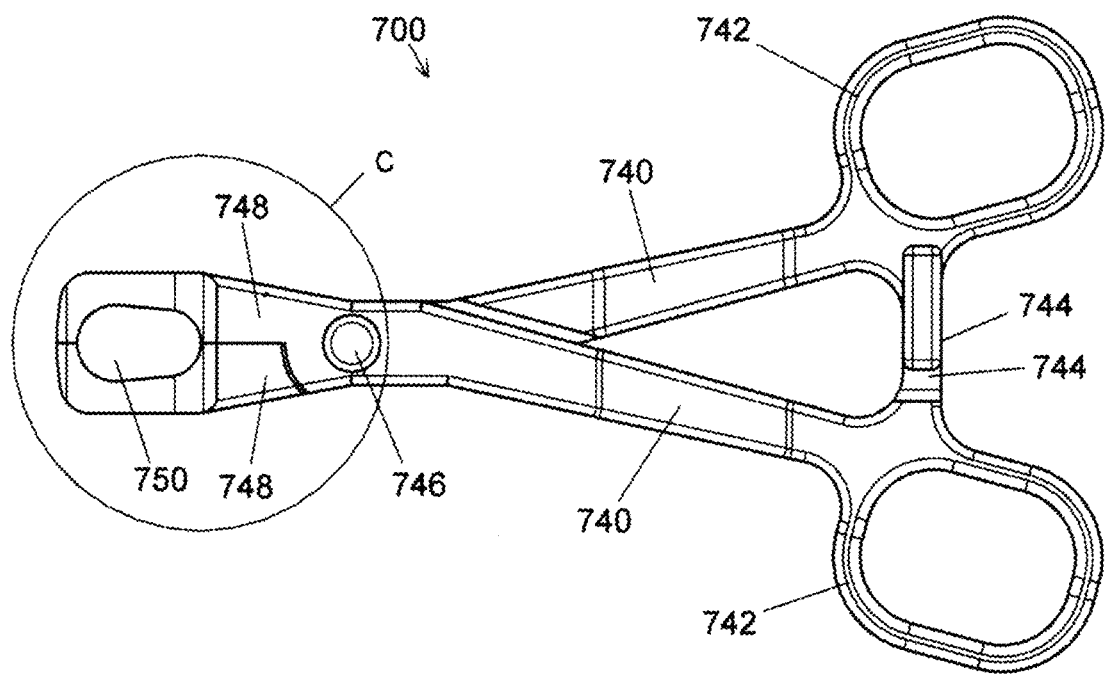
FIG. 88 is a side elevational view of the objects of FIG. 86.
Figure 89:
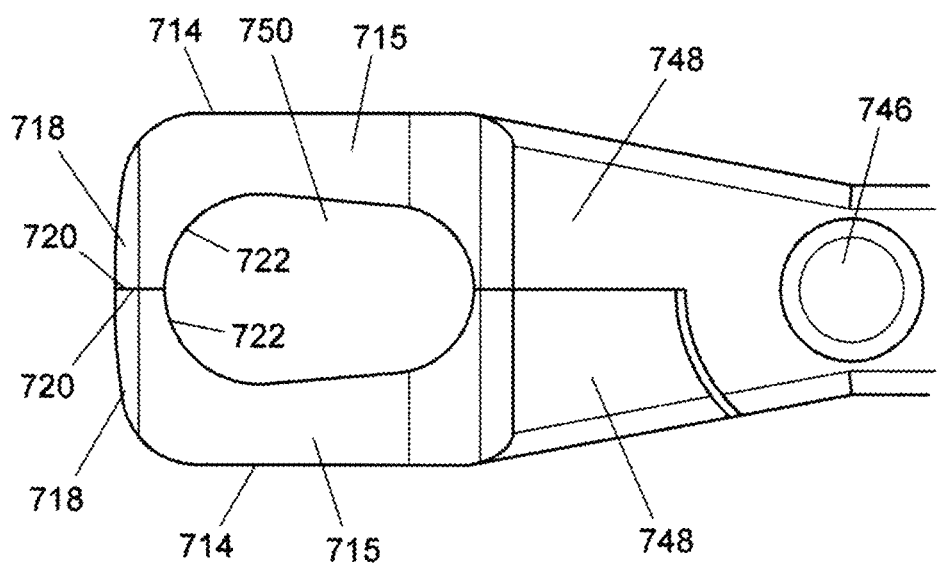
FIG. 89 is an expanded view of the objects of FIG. 88 at location C.
Figure 90:
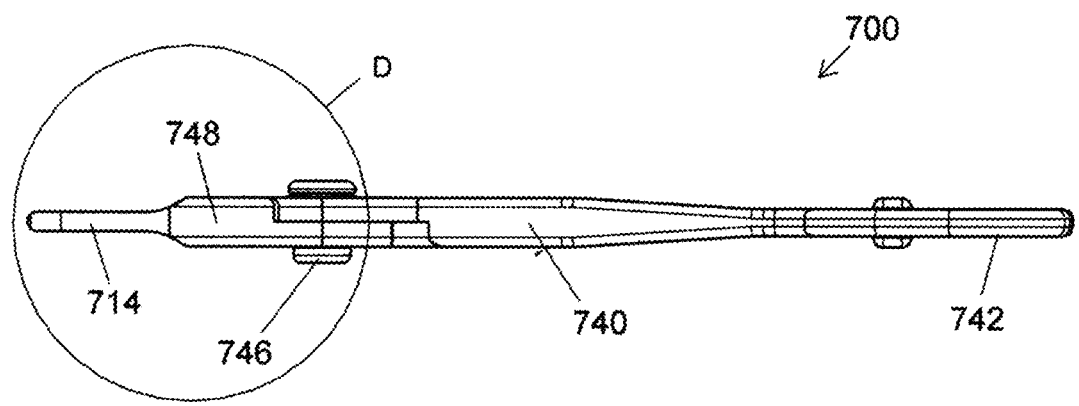
FIG. 90 is a plan view of the objects of FIG. 86.
Figure 91:
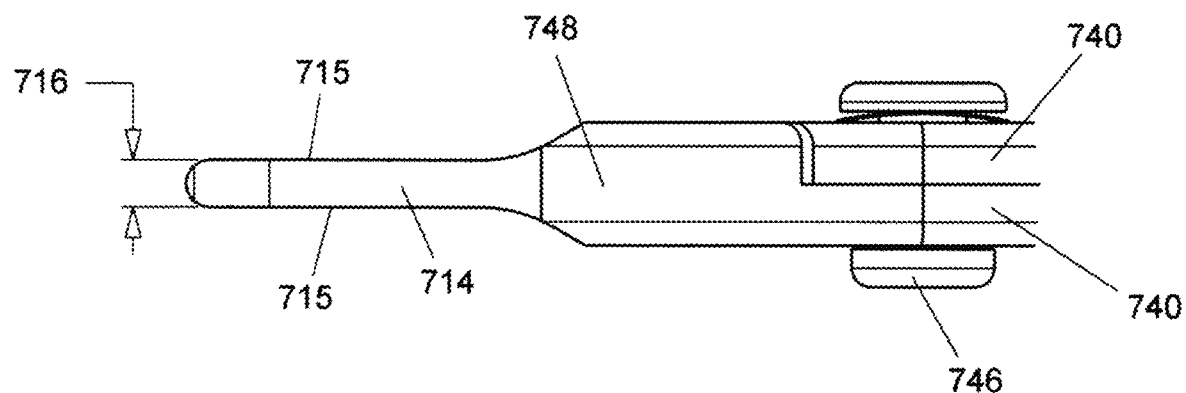
FIG. 91 is an expanded view of the objects of FIG. 90 at location D.
Figure 92:
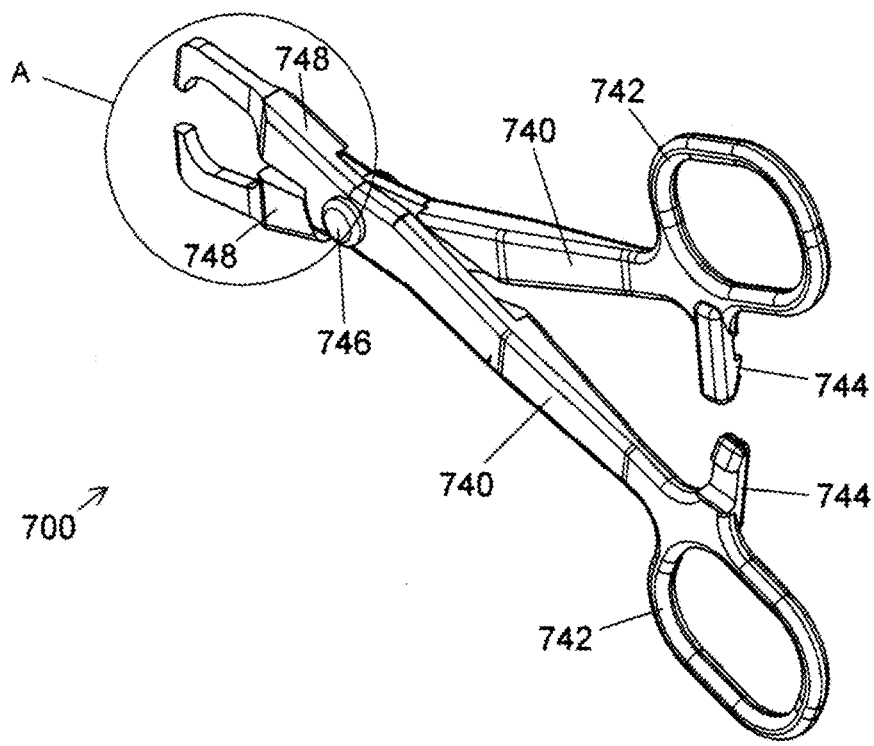
FIG. 92 is a perspective view of the alternate excising clamp of FIG. 86 in the open (unclamped) condition.
Figure 93:
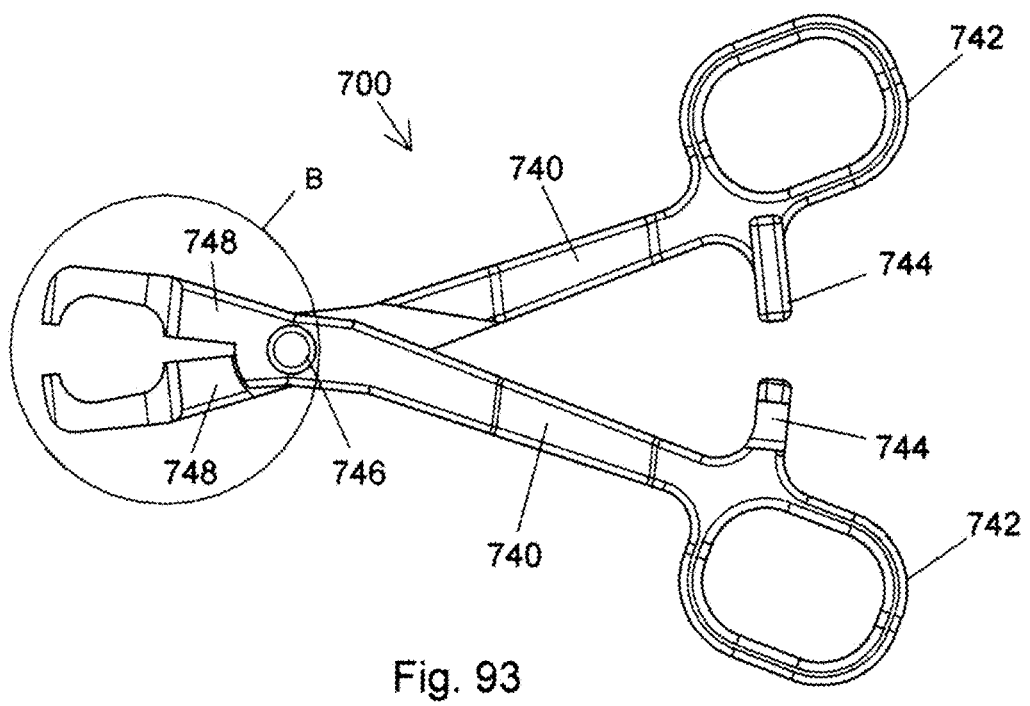
FIG. 93 is a side elevational view of the objects of FIG. 92.
Figure 94:
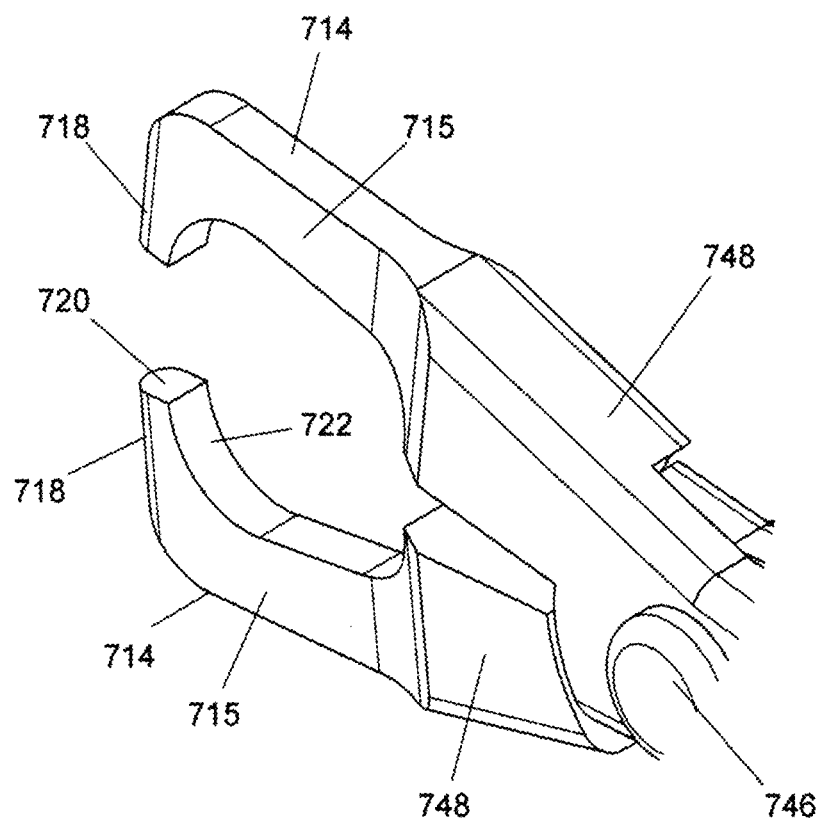
FIG. 94 is an expanded view of the objects of FIG. 92 at location A.
Figure 95:
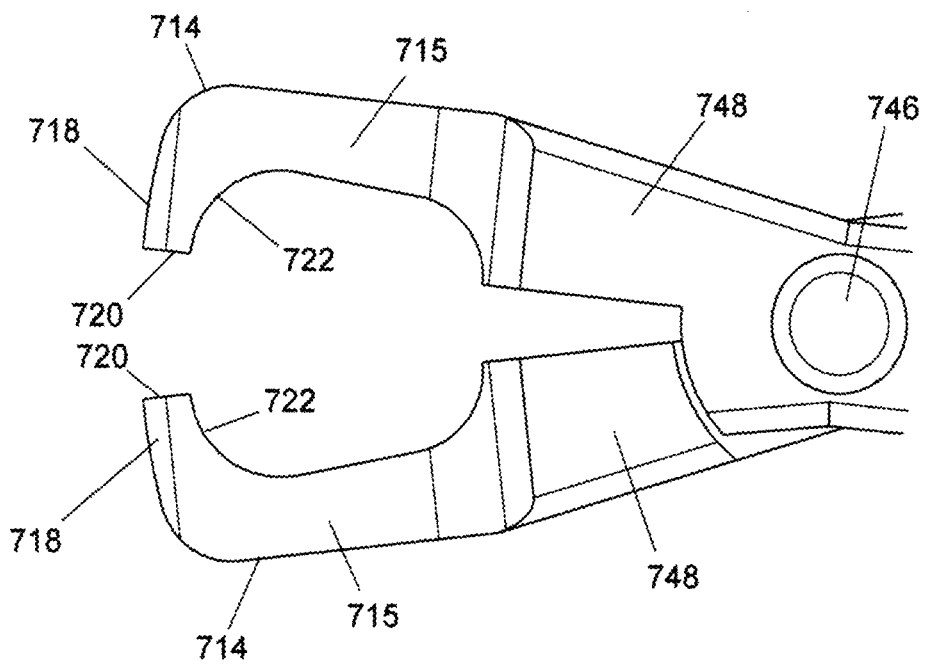
FIG. 95 is an expanded view of the objects of FIG. 93 at location B.

After coagulation of the site and removal of tissue portion 30, ratchet 430 is disengaged so as to remove the clamping pressure from jaws 408 and 428 of handpiece 400. The handpiece 400 is then opened and removed. Thereafter the site is as depicted in FIGS. 84 and 85. Region 12 contains coagulated scrotal tissue 10 and coagulated vas duct 20. Coagulated region 12 surrounds slot 14 wherein uncoagulated portion 30 was previously excised.

Vas duct 20 is coagulated along with its surrounding sheath so to provide fascial interposition sealing of duct 20 during healing.

In the above described embodiment, excising clamp 300 is moved into a clamped (closed) position by advancing control ring 360 to a distal position, clamp body 301 having a unitary construction with resilient distally extending portions 306. However, in other embodiments of excising clamps of the present invention, the clamp may be formed of two pivotably joined elements in the manner of clamp 100 (FIGS. 12 through 15). Such an alternate embodiment is depicted in FIGS. 86 through 95, wherein excising clamp 700 is formed of elements 740 having proximal portions that form finger holes 742, and whereon are formed ratchet portions 744. Elements 740 are pivotably joined by element 746. Distal to element 746, distal portions 748 of elements 740 have a distal-most portion 714 of width 716 (FIG. 91) that is slightly less than width 480 of slots 429 and 409 of jaws 428 and 408 respectively (see FIGS. 19A and 19B). Distal-most portions 714 have at their distal ends jaw portions 718 with vertically opposed, planar jaw faces 720. Distal-most portions 714 have laterally opposed surfaces 715, and surfaces 722 that are perpendicular to surfaces 715, and that together define distal opening 750 of clamp 700. The juncture of laterally opposed surfaces 715 and the distal surface joining them with vertically opposed surfaces 720 and surfaces 722 of elements 740 form a cutting edge in the same manner as the corresponding features of clamp 300. Clamp 700 is used in the same manner as clamp 300 and performs the same functions.

In use, clamp 700 maintains the position of duct 20 within fold of scrotal tissue 10 as depicted in FIGS. 74 and 75, with closure of clamp 700 being maintained by cooperative action of ratchet features 744 of elements 740. Thereafter, jaws 408 and 428 of device 400 are positioned around distal portions 714 of clamp 700 in the same manner as depicted with portions 314 of clamp 300 in FIGS. 76 through 79. When coagulation is complete, tissue portion 30 (FIGS. 80 and 81) is removed by clamp 700 in the same manner as depicted using clamp 300. Cutting edges of distal portions 714 in cooperation with cutting edges of jaws 408 and 428 of coagulating device 400 separate tissue portion 30 from the surrounding coagulated tissue trapped between jaws 408 and 428.

Figure 96:
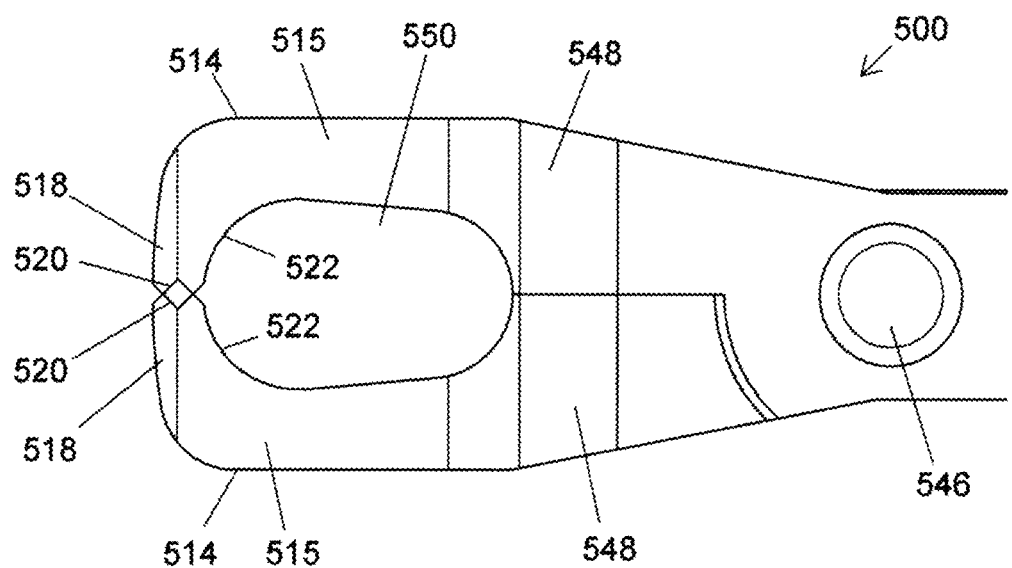
FIG. 96 is a side elevational view of an excising clamp of the present invention analogous to that depicted in FIG. 86 in which the jaws of the distal clamping portion (depicted in the closed (clamped) condition) are modified to include mirror-image serrations.
Figure 97:
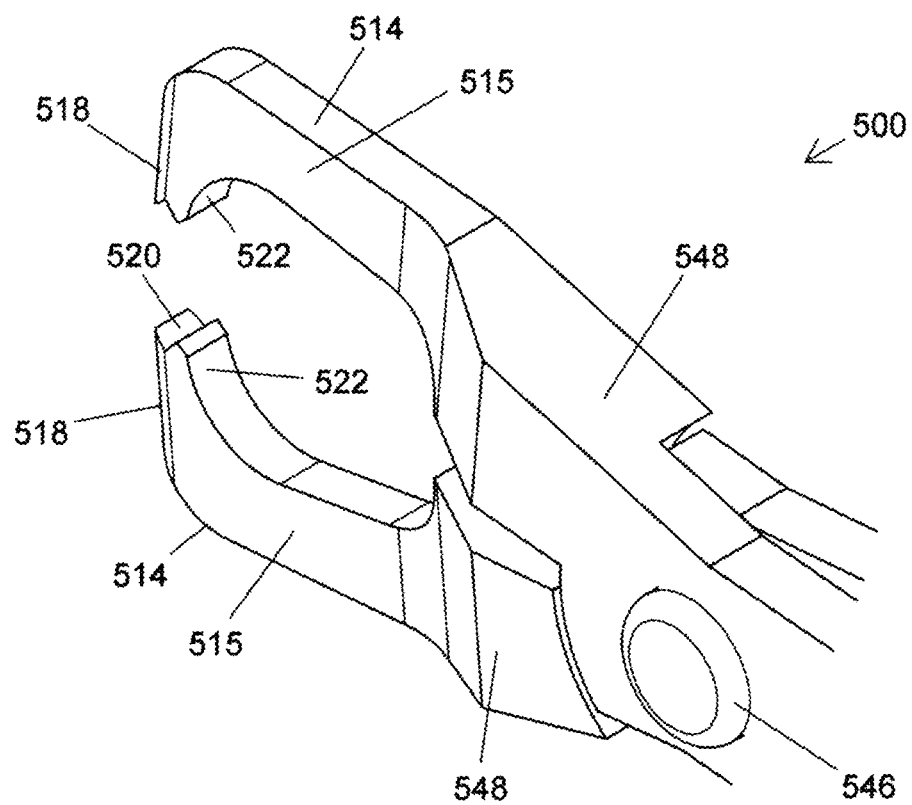
FIG. 97 is a perspective view of the alternative excising clamp of FIG. 96 in which the modified jaws are depicted in the open (unclamped) condition.

While vertically opposed surfaces 720 of distal portions 714 of clamp 700 are depicted as planar, in other alternate embodiments of the present invention serrations may be formed on surface to aid in maintaining the location of jaws 718 when clamping scrotal tissue, and to aid in cutting tissue portion 30 from the surrounding coagulating tissue. For instance, excising clamp 500, the distal portion of which is depicted in FIGS. 96 and 97, is identical in all aspects of form and function to excising clamp 700 except as specifically subsequently herein described. Vertically opposed surfaces 520 of clamp 500 have formed thereon serrations, the serrations on a first surface 520 being a mirror of the serrations on the opposing, second surface 520.

Figure 98:
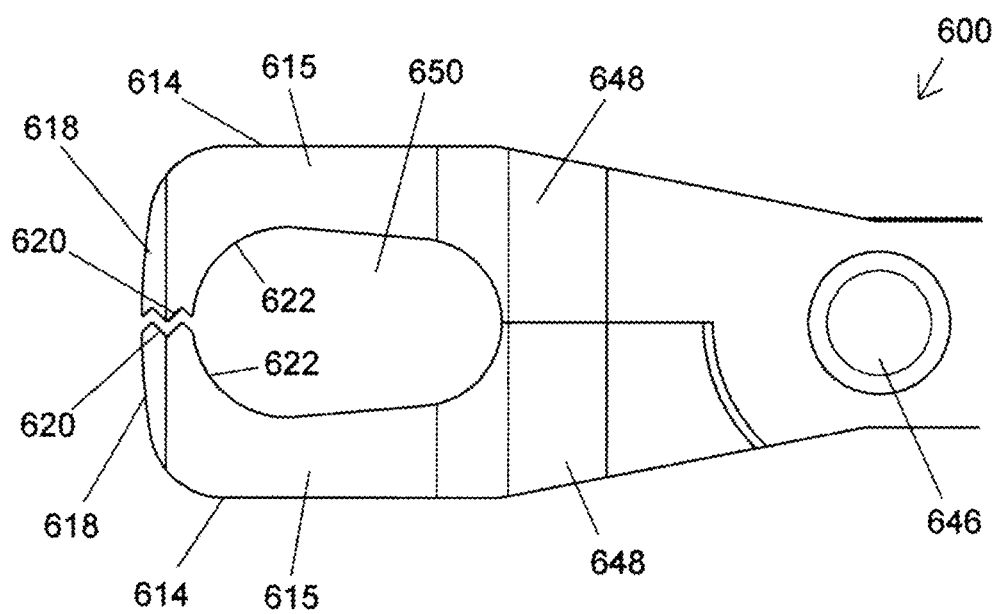
FIG. 98 is a side elevational view of another excising clamp of the present invention analogous to that depicted in FIG. 86 in which the jaws of the distal clamping portion (depicted in the closed (clamped) condition) are modified to include complementary serrations.
Figure 99:
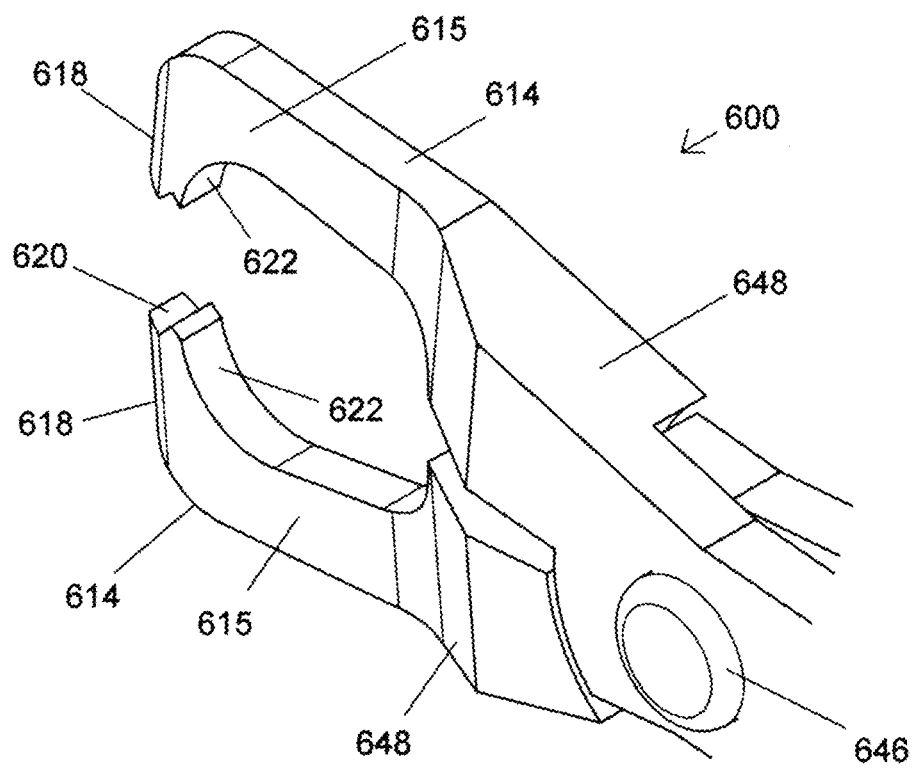
Figure 100:
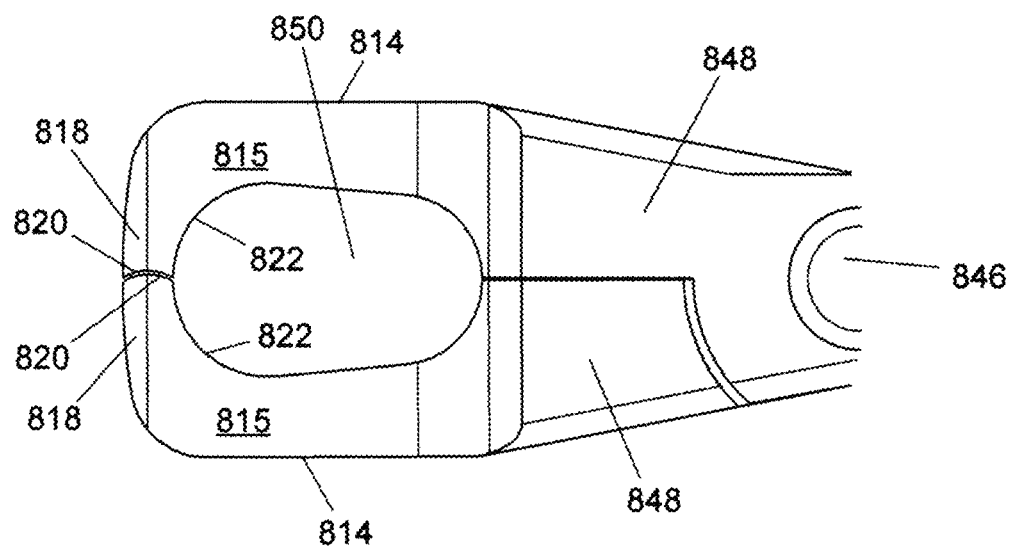
Figure 101:
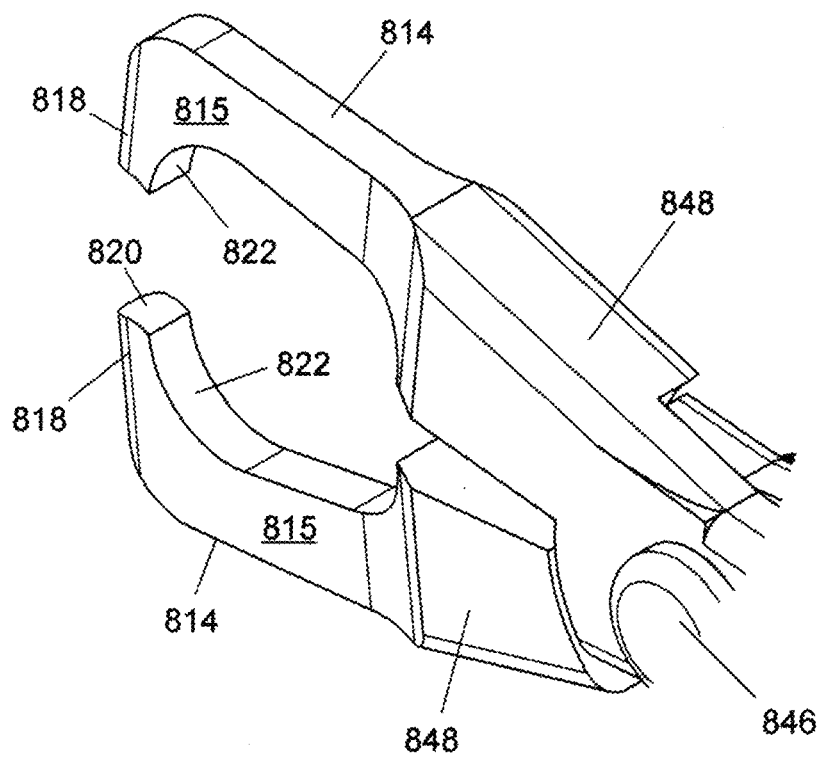
Figure 105:
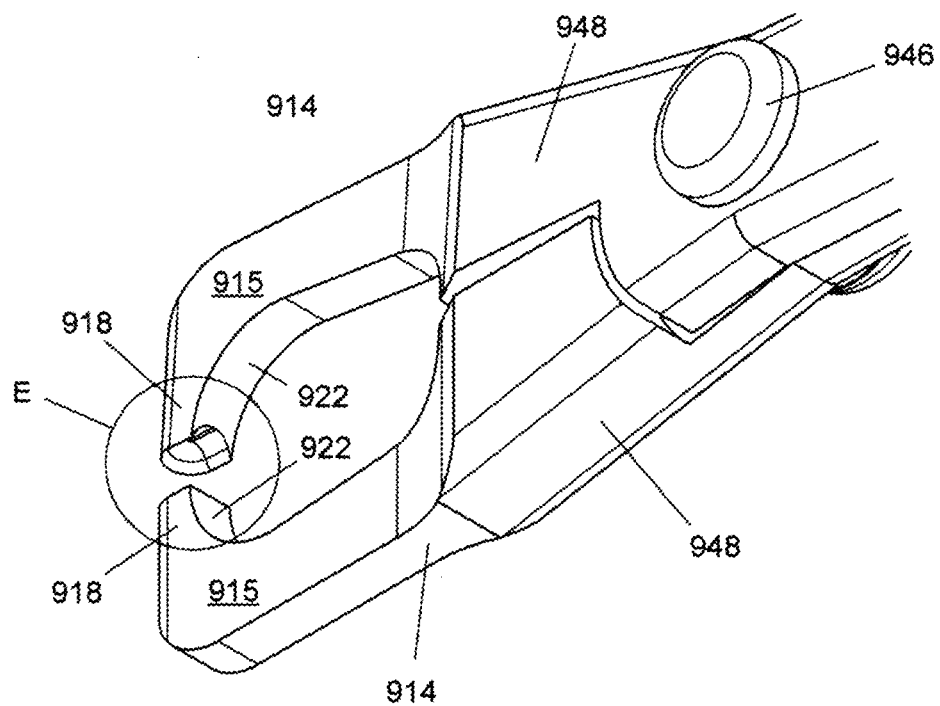
Figure 106:
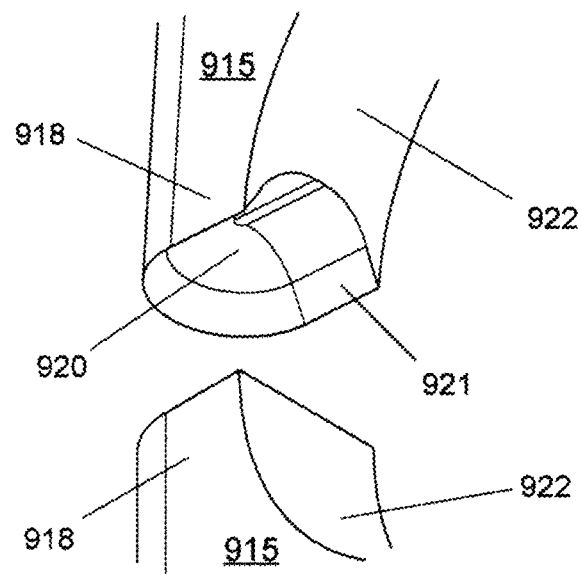

Another embodiment of an excising clamp 600 in accordance with the present invention is depicted in FIGS. 98 and 99 and is identical in all aspects of form and function to clamp 700 except as specifically subsequently described. Vertically opposed surfaces 620 of clamp 600 have formed thereon serrations, the serrations on a first surface 520 being complementary to the serrations on the opposing, second surface 520. Another alternate embodiment excising clamp 800 is identical in all aspects to previously described clamp 700 in form and function except that vertically opposed surfaces 820 are configured as complementary cylindrical surfaces. Indeed, the vertically opposed clamping surfaces of excising clamps of the present invention may be optimized for the dual functions of clamping tissue so as to maintain the position of a vas duct in a fold of scrotal skin, and of subsequently excising a tissue portion that is confined within the jaws of a coagulating device. These clamping surfaces may be planar, may have serrations formed thereon, may have a cylindrical surface formed thereon, or may have a combination of these features. Cross-sections of these surfaces may include linear, radial or curvilinear shapes. All fall within the scope of the present invention.

Figure 107:
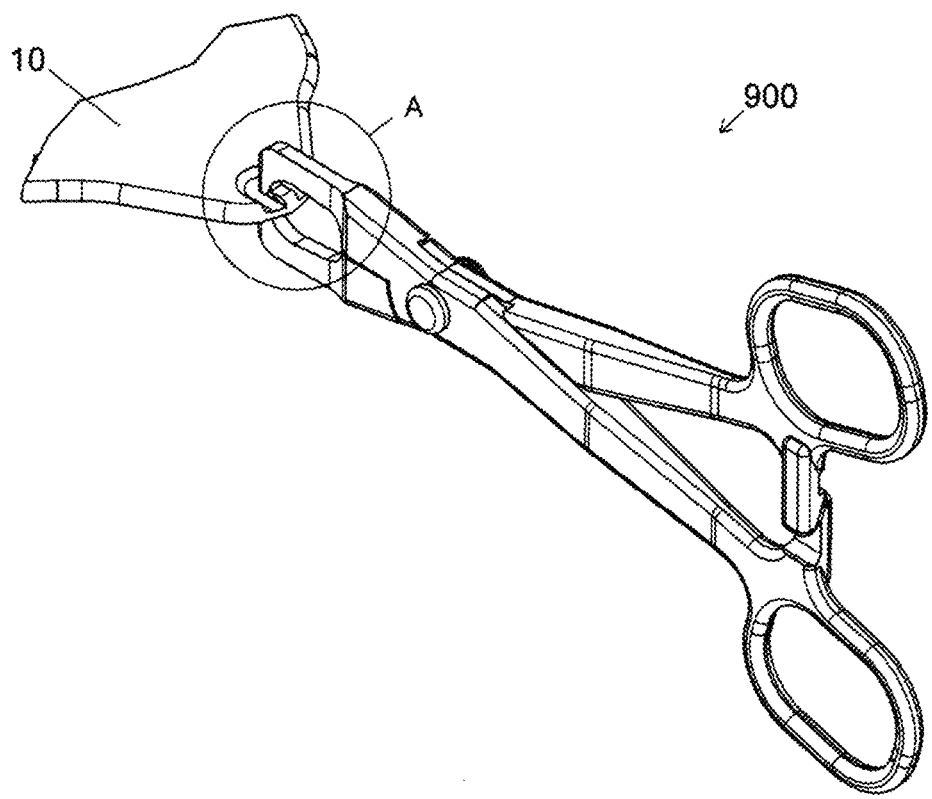
Figure 108:
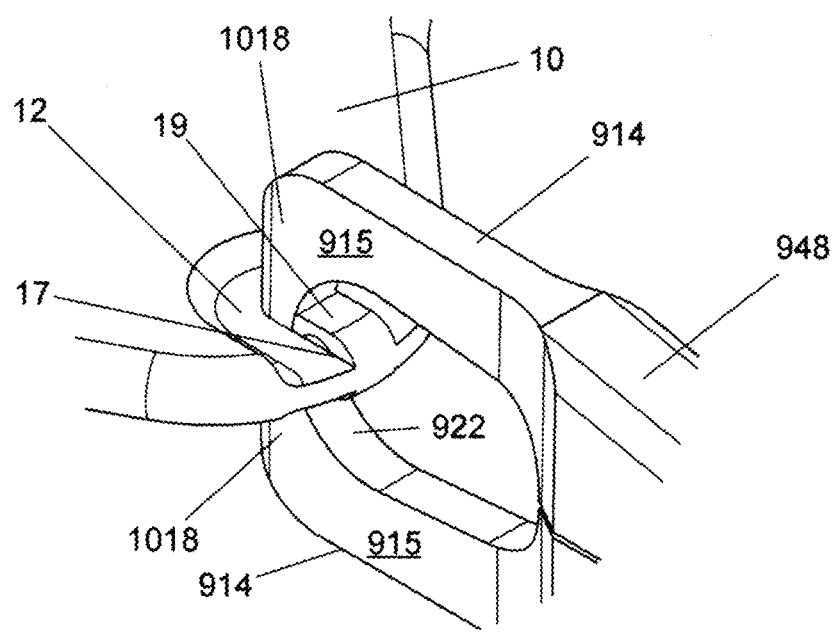

In excising clamps of the present invention previously described herein, opposed surfaces 820 of clamp 800 are indicated as perpendicular to lateral surfaces 815, with surfaces 720 of clamp 700 being perpendicular to lateral surfaces 715, and surfaces 620 of clamp 600 being perpendicular to lateral surfaces 615. However, in an alternate embodiment of the present invention, low included angle cutting edges may be formed on the upper opposed clamping surface to aid in tissue dissection. Referring now to FIGS. 102 through 106 depicting the distal portion of such an alternate excising clamp 900, upper opposed surface 920 is not planar like lower opposed surface 920, but rather has formed thereon beveled edges 921 with included angle 919. Beveled edges 921 extend around the distal radius of upper opposed surface 920 so that a continuous cutting edge is formed. Angle 919 is preferably between 10 and 80 degrees, and more preferably between 20 and 60 degrees. Excising clamp 900 may be used in the same manner as those previously herein described, that is, to maintain the position of the vas duct in a fold of scrotal tissue, to provide a guide for positioning of the jaws of handpiece 400, and to excise the uncoagulated tissue portion from the site when coagulation is complete. Because low included angle edges 921 are formed on upper opposed surface 920, clamp 900 may optionally be used to excise the uncoagulated tissue portion from the site when coagulation is complete without cooperative interaction with jaws 408 and 428 of device 400. That is, jaws 408 and 428 may be unclamped and device 400 may be removed from the site when coagulation is complete. Thereafter, the site is as depicted in FIGS. 107 and 108 wherein clamp jaws 1018 are positioned on scrotum portion 10. Uncoagulated tissue portion 19 is surrounded by arcuate coagulated region 12, the opposing sharp inner edges of jaws 408 and 428 creating a sharp margin 17 between uncoagulated tissue portion 19 and surrounding coagulated region 12. When clamp 900 is moved downward and proximally edges 921 of upper opposed clamping surface 920 initiate dividing of the tissue along margin 17 so that uncoagulated portion 19 is removed from the site. Thereafter the site is as previously depicted in FIGS. 84 and 85.

Figure 109:
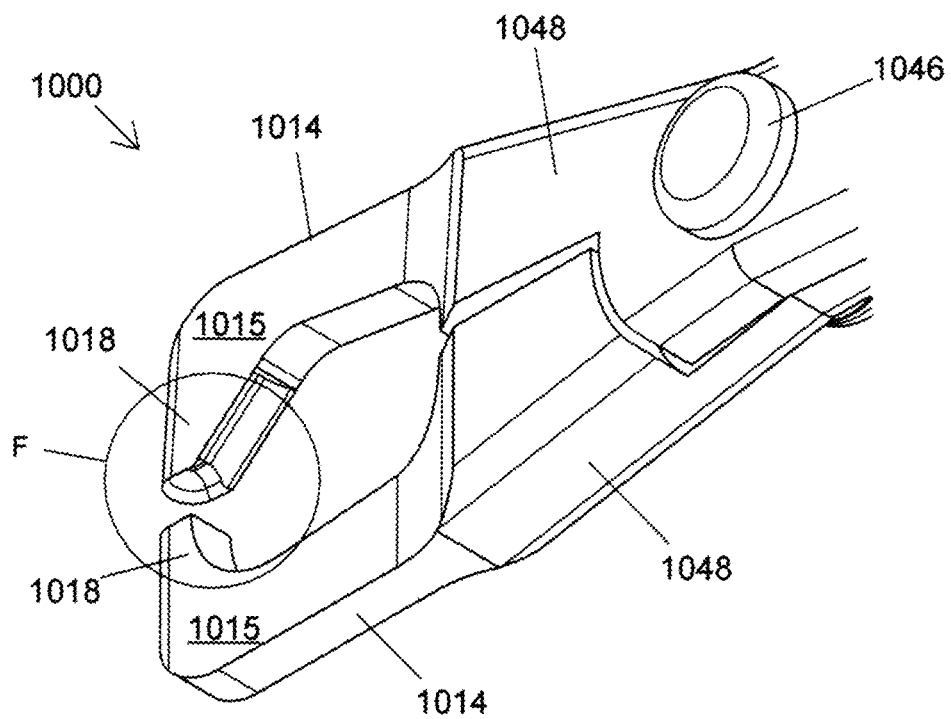
Figure 110:
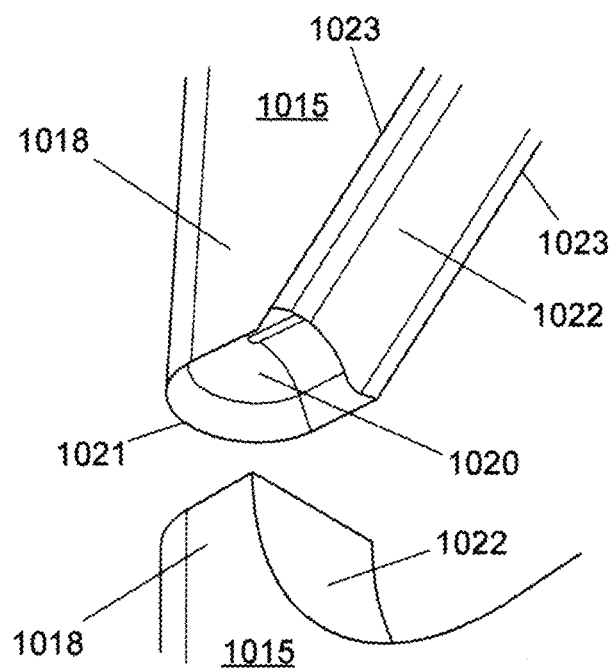

In an alternate embodiment, shown in FIGS. 109 and 110, low included angle edges 1023 are formed on a distal portion of surface 1022 of the upper jaw 1014 of clamp 1000 to aid in excising portion 19 from coagulated region 12.

INDUSTRIAL APPLICABILITY

All publications mentioned herein are incorporated herein by reference in their entirety. However, nothing herein should be construed as an admission that the invention is not entitled to antedate such disclosure by virtue of prior invention.

As noted previously herein, the vasectomy device, kit and method for performing vasectomies of the present invention overcome disadvantages and deficiencies of conventional vasectomy materials and methods by providing a rapid, reliable, less invasive male sterilization procedure that reduces or eliminates negative side effects, including swelling and spontaneous regeneration, and minimizes recovery time and recovery restrictions. It further avoids or minimizes the potential for exposure to patient bodily fluids, thereby minimizing the potential for transmission of blood-borne diseases such as HIV and Hepatitis.

Due to the complications associated with traditional vasectomies but eliminated by the techniques and devices herein disclosed, successful procedures have, in the past, required the utilization of skilled experienced surgeons. However, the vasectomy device and method of the instant invention minimizes the number of steps and duration of the procedure, thereby allowing the procedure to be quickly completed by clinicians with minimal training. Moreover, given its simplicity, less skilled heath care workers can master the procedure in a relatively short period of time. This will extend the feasibility of male sterilization to areas of the world where doctors, more particularly skilled surgeons, are in short supply. For example, the instruments, kit and method of the instant invention may be advantageously used for family planning in developing countries.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A method for performing a vasectomy comprising the steps of:
   (a) locating a length of a vas deferens within a scrotum, wherein said vas deferens is characterized by an outer vas sheath disposed about an inner vas duct, further wherein said inner vas duct is characterized by curved proximal and distal walls that meet at a midline to form an integral tubular channel;
   (b) placing a tissue-capturing distal portion of a surgical clamp approximately about said midline of said inner vas duct contained within said length of vas deferens so as to temporarily isolate a portion of vas tissue that includes both proximal and distal walls of said inner vas duct but excludes at least part of a distal region of said outer vas sheath;
   (c) providing a bipolar device having a proximal handle portion that defines a longitudinal axis of said device and a distal clamping portion characterized by a pair of opposingly-faced, upper and lower coagulating jaws, wherein each of said jaws is (i) movable between open and closed positions, (ii) provided with mating distal tips and inner edges, whereby, when said jaws are in the closed position and viewed in a plan view, said mating distal tips are angularly offset from said longitudinal axis and said mating inner edges engage to define an interior perimeter comprised of (1) an open central slot that terminates in (2) a lateral opening sized to permit said distal clamping portion to be positioned around said tissue-capturing distal portion of said surgical clamp that retains said isolated portion of vas tissue;
   (d) tightly closing said coagulating jaws about the tissue-capturing distal portion of said surgical clamp to thereby define (i) a first area of clamped vas tissue disposed between said closed coagulating jaws and (ii)

a second area defined by said interior perimeter that includes said isolated portion of vas tissue retained by said tissue-capturing distal portion of said surgical clamp; and (e) activating said coagulating bipolar device so as to coagulate said first area of clamped vas tissue.

2. The vasectomy method according to claim 1, wherein said inner vas duct is retained within said outer vas sheath for the duration of the procedure.

3. The method according to claim 1, wherein said locating step (a) further includes the step of manipulating said inner vas duct into a fold of scrotal tissue in a high lateral position.

4. The method according to claim 1, wherein said surgical clamp is placed medially adjacent to the vas duct.

5. The method according to claim 1, wherein said surgical clamp is a ring forceps.

6. The method according to claim 5, wherein a distal end of said ring forceps is placed at said midline of said inner vas duct so as to compress said vas duct between opposed clamping faces of said ring forceps.

7. The method according to claim 1, wherein said mating inner edges are sharpened so as to enable direct excision of said second area that includes said isolated portion of vas tissue that includes both proximal and distal walls of said inner vas duct but excludes at least part of said distal region of said outer vas sheath.

8. The vasectomy method according to claim 1, wherein said coagulation of said first area of clamped vas tissue serves to both bisect the vas duct into separated abdominal and testicular legs and deaden sensory nerves located in the distal region of said outer vas sheath.

9. The vasectomy method according to claim 1, wherein said upper and lower jaws as well as said first area of clamped tissue are arcuate in shape such that said second area comprises a convex region.

\* \* \* \* \*